United States Patent
Terliuc et al.

(10) Patent No.: US 9,596,979 B2
(45) Date of Patent: Mar. 21, 2017

(54) ANCHORING ASSEMBLIES FOR ENDOSCOPES

(75) Inventors: Gad Terliuc, Ra'anana (IL); Gilad Luria, Givataim (IL); Maxim Musheev, Ramla (IL)

(73) Assignee: SMART MEDICAL SYSTEMS LTD., Ra'anana (IL)

( * ) Notice: Subject to any disclaimer, the term of this patent is extended or adjusted under 35 U.S.C. 154(b) by 0 days.

(21) Appl. No.: 13/322,996

(22) PCT Filed: May 30, 2010

(86) PCT No.: PCT/IL2010/000425
§ 371 (c)(1),
(2), (4) Date: Feb. 9, 2012

(87) PCT Pub. No.: WO2010/137025
PCT Pub. Date: Dec. 2, 2010

(65) Prior Publication Data
US 2012/0130170 A1     May 24, 2012

Related U.S. Application Data

(60) Provisional application No. 61/282,621, filed on Mar. 9, 2010, provisional application No. 61/213,320, filed
(Continued)

(51) Int. Cl.
*A61B 1/00*     (2006.01)
*A61B 1/012*     (2006.01)
(Continued)

(52) U.S. Cl.
CPC .......... *A61B 1/012* (2013.01); *A61B 1/00082* (2013.01); *A61B 1/01* (2013.01)

(58) Field of Classification Search
CPC ....... A61B 1/00082; A61B 1/012; A61B 1/01; A61B 5/6853; A61B 2017/22048
(Continued)

(56) References Cited

U.S. PATENT DOCUMENTS

| 3,387,347 A | 6/1968 | John |
| 4,040,413 A | 8/1977 | Ohshiro |

(Continued)

FOREIGN PATENT DOCUMENTS

| EP | 0047465 A1 | 3/1982 |
| JP | 2003-250896 A | 9/2003 |

(Continued)

OTHER PUBLICATIONS

Double Balloon Endoscope product, including EC-450BI5 colonoscope, TS-13101 overtube and BS-2 front balloon, which interface with balloon pump controller BP-20 and EPX-4400HD video system, all commercially available from Fojinon Inc. of 10 High Point Drive, Wayne New Jersey, USA, 5 pages www.fujinonla.com/inc/class/descargar.php?url=/archivos/.../dbe brought to applicant's attention on Nov. 17, 2005.
(Continued)

*Primary Examiner* — Timothy J Neal
(74) *Attorney, Agent, or Firm* — Ladas & Parry LLP

(57) ABSTRACT an endoscope system including an endoscope having an instrument channel and an anchoring assembly including an inflatable/deflatable balloon assembly, the inflatable/deflatable balloon assembly being deflatable to a cross-sectional size sufficiently small to enable it to pass through the instrument channel and being positionable and inflatable without substantial stretching to have a dimension sufficiently large to enable it to anchor in the large intestine.

16 Claims, 59 Drawing Sheets

Related U.S. Application Data on May 29, 2009, provisional application No. 61/282,501, filed on Feb. 22, 2010.

(51) Int. Cl.
 *A61B 1/01* (2006.01)
 *A61B 1/04* (2006.01)

(58) Field of Classification Search
 USPC .......... 600/115, 116, 114, 121–125; 604/509
 See application file for complete search history.

(56) References Cited

U.S. PATENT DOCUMENTS

| | | | |
|---|---|---|---|
| 4,148,307 A | | 4/1979 | Utsugi |
| 4,176,662 A | | 12/1979 | Frazer |
| 4,195,637 A | | 4/1980 | Grüntzig et al. |
| 4,261,339 A | | 4/1981 | Hanson et al. |
| 4,292,974 A | | 10/1981 | Fogarty et al. |
| 4,346,698 A | * | 8/1982 | Hanson et al. .................. 600/18 |
| 4,453,545 A | | 6/1984 | Inoue |
| 4,616,652 A | | 10/1986 | Simpson |
| 4,676,228 A | | 6/1987 | Krasner et al. |
| 4,862,874 A | | 9/1989 | Kellner |
| 4,917,088 A | | 4/1990 | Crittenden |
| 5,135,487 A | | 8/1992 | Morrill et al. |
| 5,167,239 A | | 12/1992 | Cohen et al. |
| 5,259,366 A | | 11/1993 | Reydel et al. |
| 5,593,419 A | | 1/1997 | Segar |
| 6,007,482 A | | 12/1999 | Madni et al. |
| 6,461,294 B1 | | 10/2002 | Oneda et al. |
| 6,585,639 B1 | | 7/2003 | Kotmel et al. |
| 6,663,589 B1 | | 12/2003 | Halevy |
| 6,702,735 B2 | | 3/2004 | Kelly |
| 6,951,554 B2 | * | 10/2005 | Johansen et al. .............. 604/509 |
| 2004/0102681 A1 | | 5/2004 | Gross |
| 2004/0147811 A1 | | 7/2004 | Diederich et al. |
| 2004/0186349 A1 | * | 9/2004 | Ewers et al. .................. 600/114 |
| 2005/0124856 A1 | | 6/2005 | Fujikura et al. |
| 2005/0125005 A1 | | 6/2005 | Fujikura |
| 2005/0133453 A1 | | 6/2005 | Woodruff et al. |
| 2005/0137457 A1 | | 6/2005 | Machida |
| 2005/0165233 A1 | | 7/2005 | Hamedi et al. |
| 2005/0165273 A1 | | 7/2005 | Takano |
| 2006/0111610 A1 | | 5/2006 | Machida |
| 2006/0161044 A1 | | 7/2006 | Oneda et al. |
| 2007/0083158 A1 | | 4/2007 | Hirszowicz et al. |
| 2007/0244361 A1 | | 10/2007 | Ikeda et al. |
| 2008/0119693 A1 | * | 5/2008 | Makower et al. ............ 600/114 |

FOREIGN PATENT DOCUMENTS

| | | |
|---|---|---|
| WO | 2005/074377 A2 | 8/2005 |
| WO | 2007/017854 A2 | 2/2007 |
| WO | 2007/135665 A2 | 11/2007 |
| WO | 2008/004228 A2 | 1/2008 |
| WO | 2008/142685 A2 | 11/2008 |
| WO | 2009/122395 A2 | 10/2009 |
| WO | 2009/140213 A1 | 11/2009 |
| WO | 2010/046891 A2 | 4/2010 |
| WO | 2010/137025 A2 | 12/2010 |

OTHER PUBLICATIONS

International Search Report and Written Opinion dated Dec. 13, 2010 issued during prosecution of PCT/IL2010/000425.
International Preliminary Report on Patentability dated Nov. 29, 2011 issued during prosecution of PCT/IL2010/000425.
An English Translation of the Prior Art issues only in an Office Action dated Sep. 1, 2013, which issued during the prosecution of Israel Patent Application No. 216630.
Extended European Search Report dated May 26, 2014; Appln No. 10780156.5-1660/ 2434938 PCT/IL2010000425.

* cited by examiner

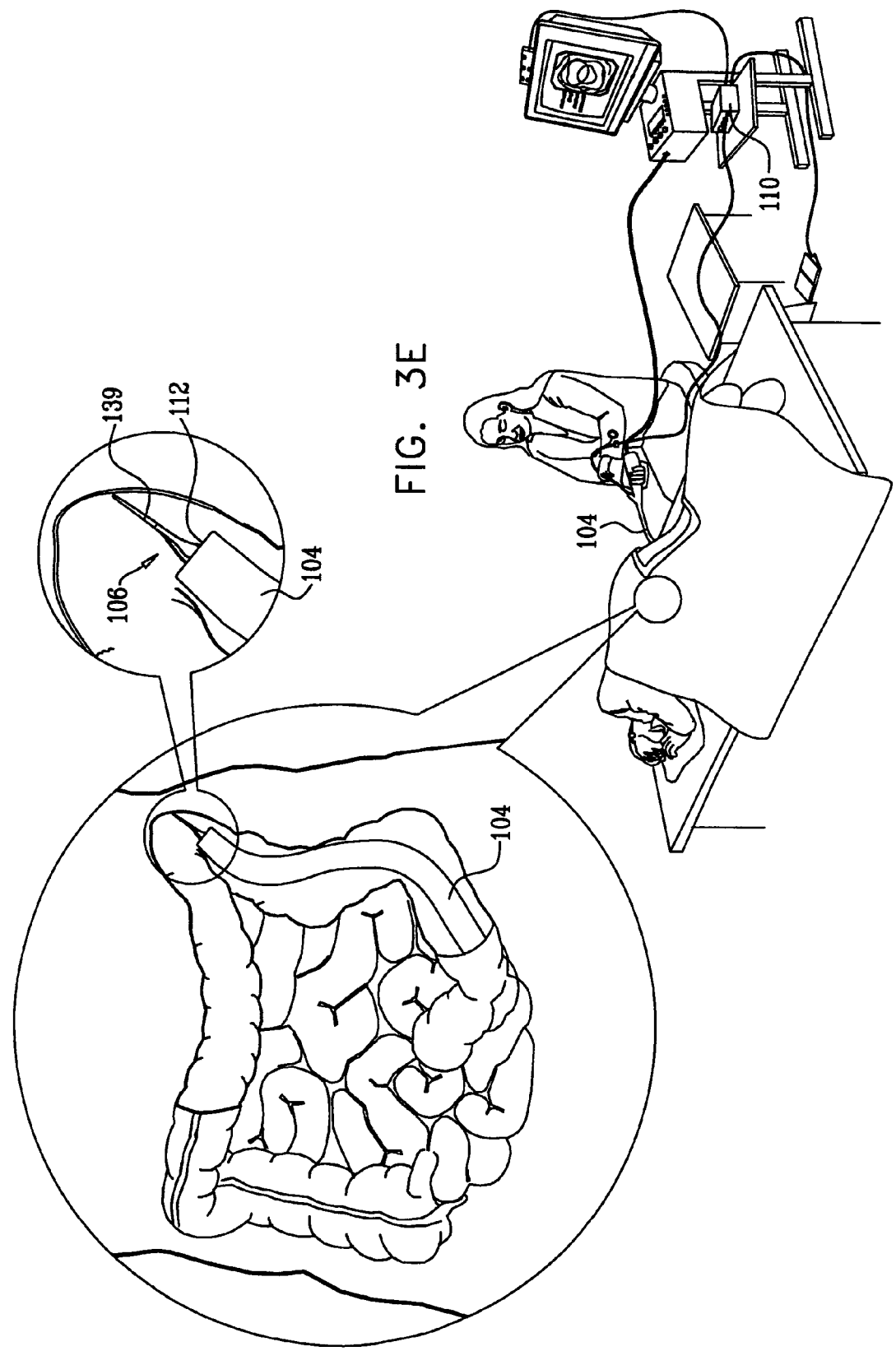

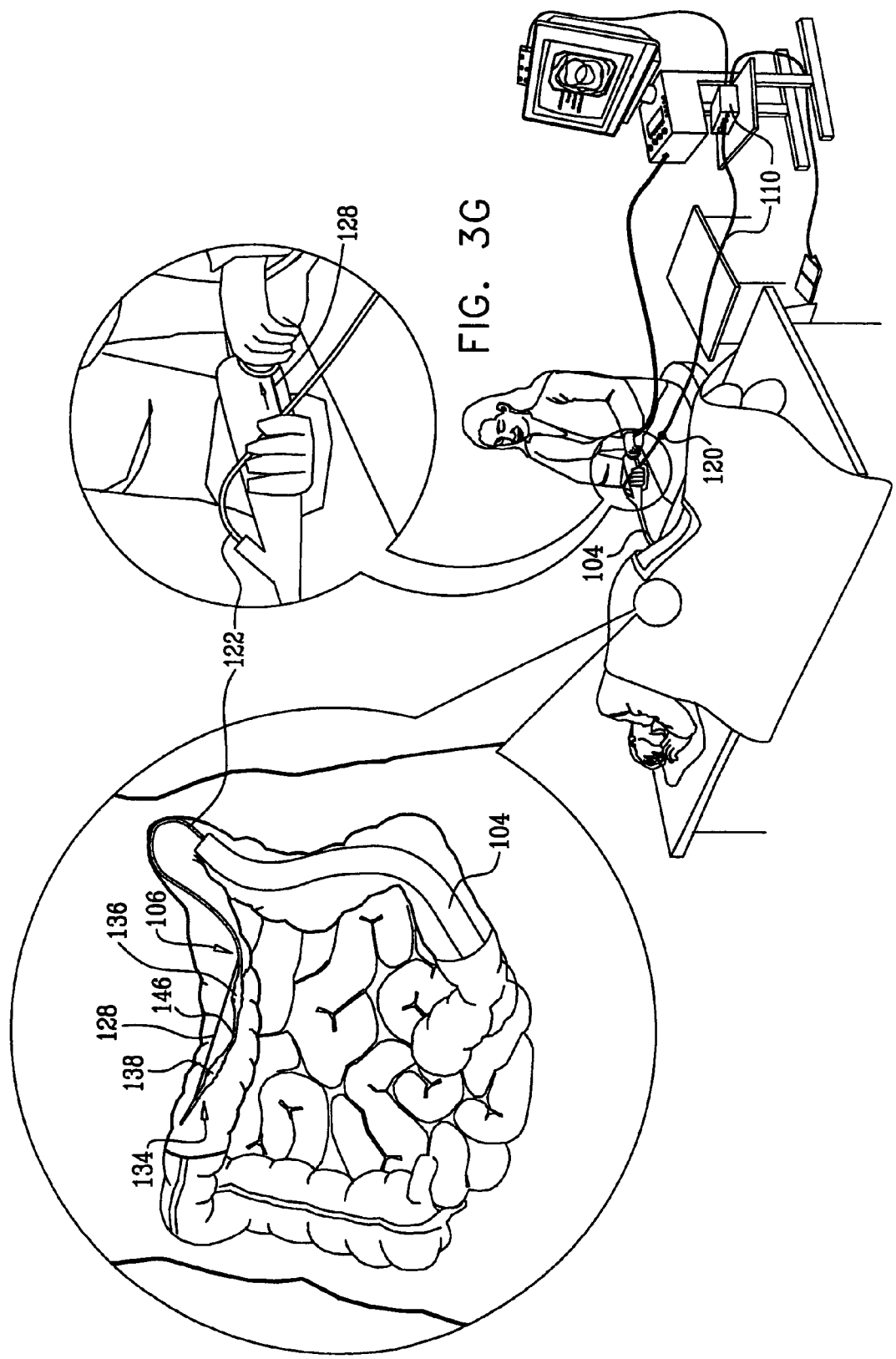

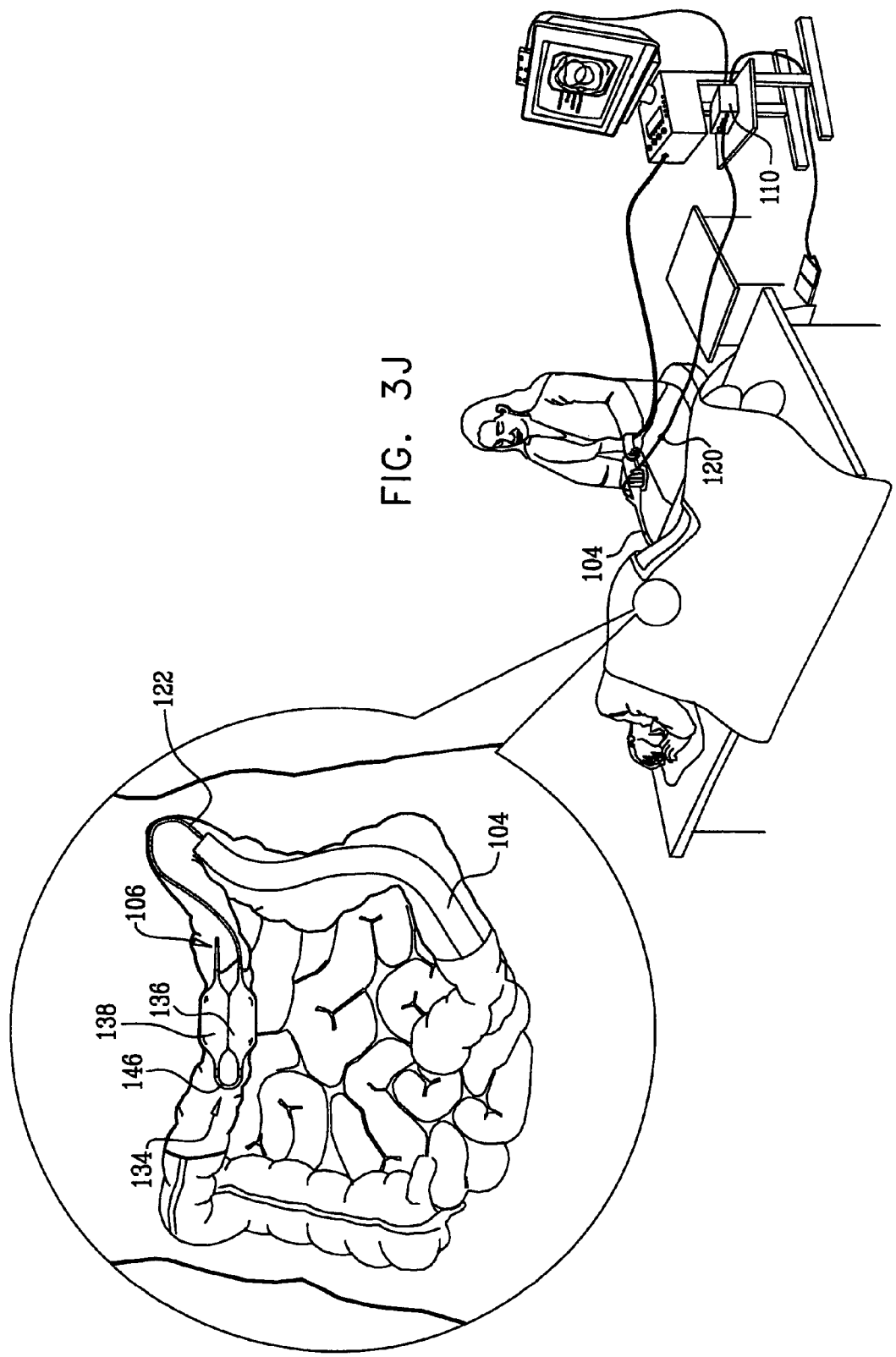

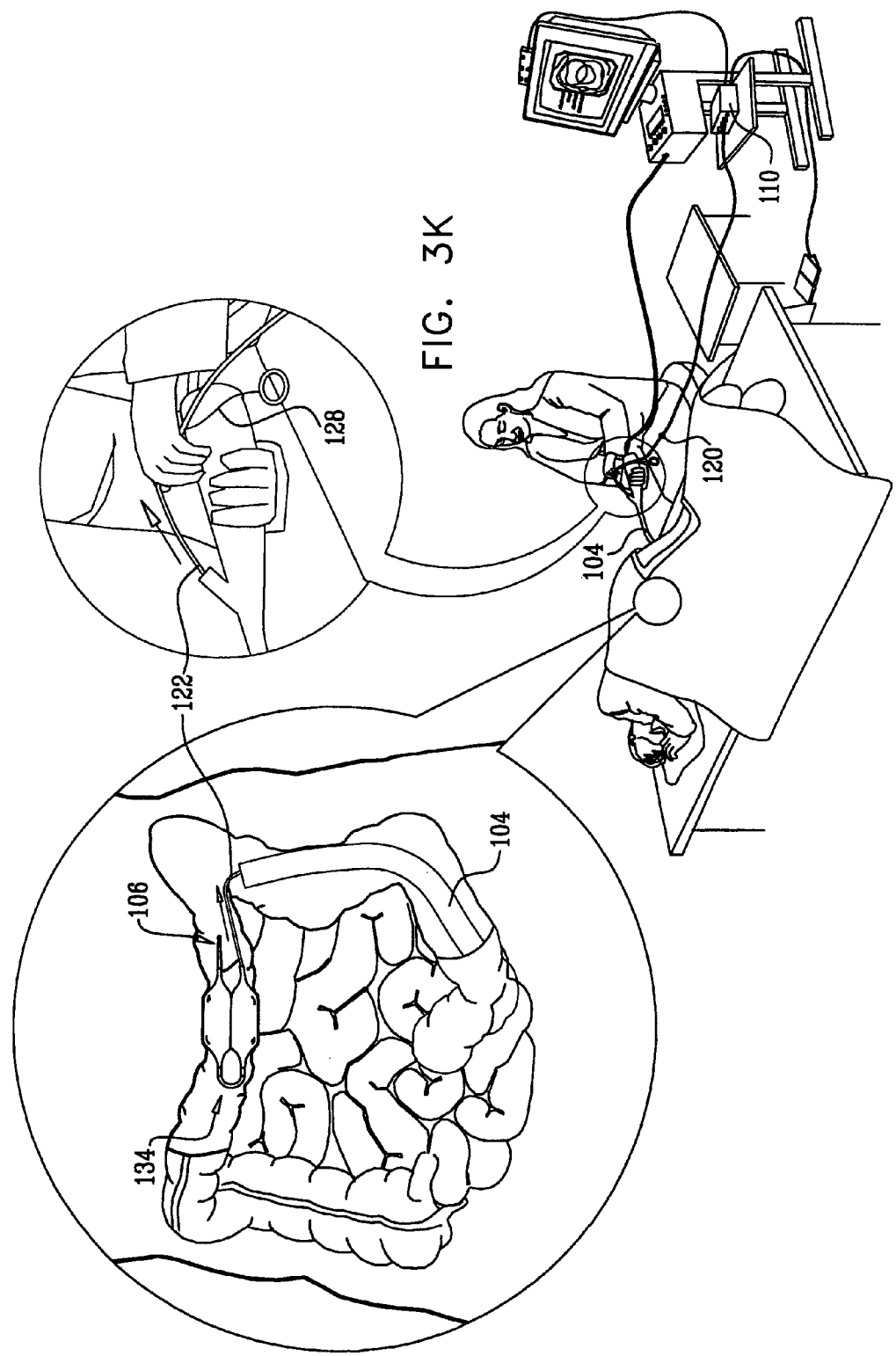

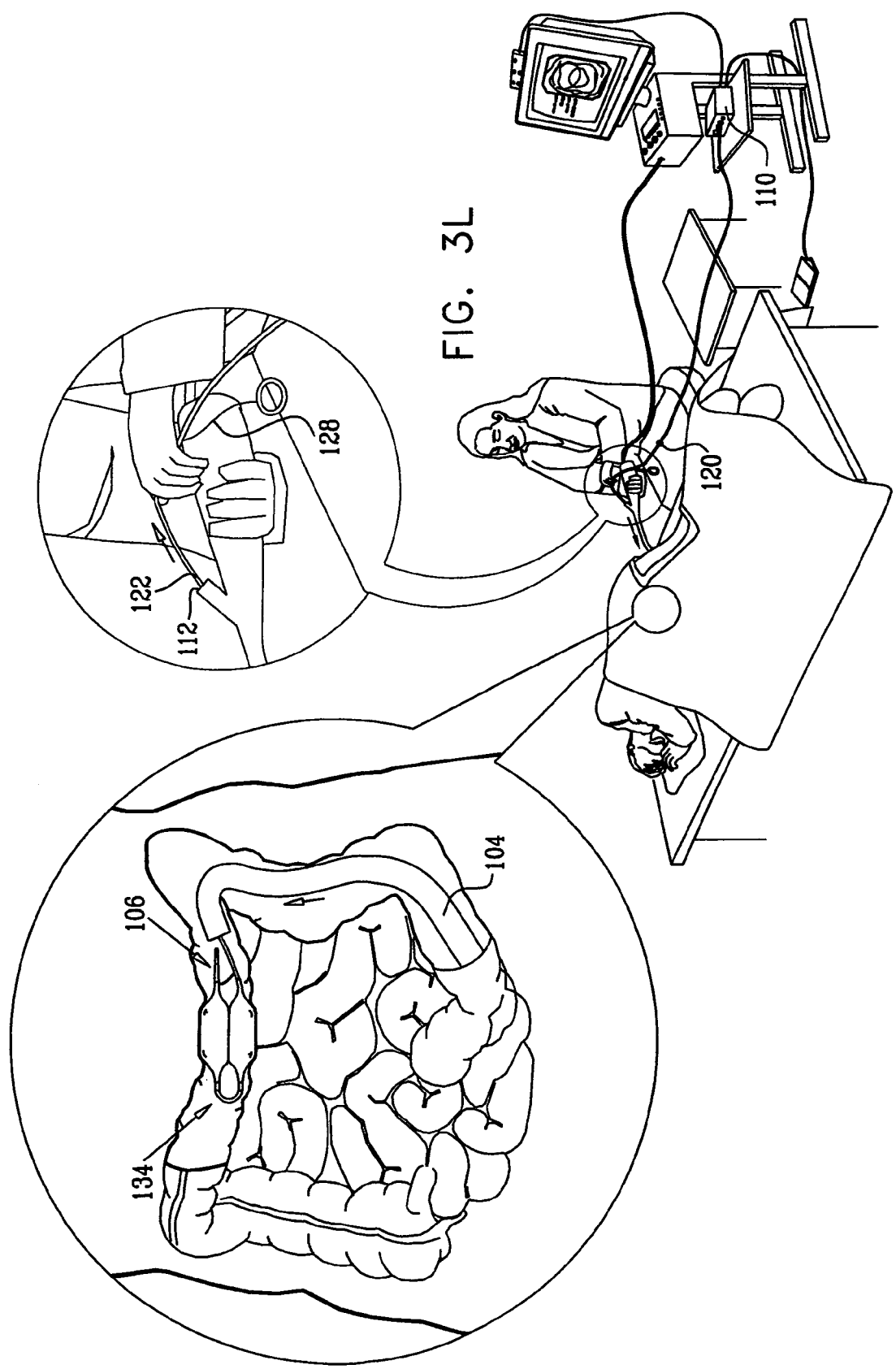

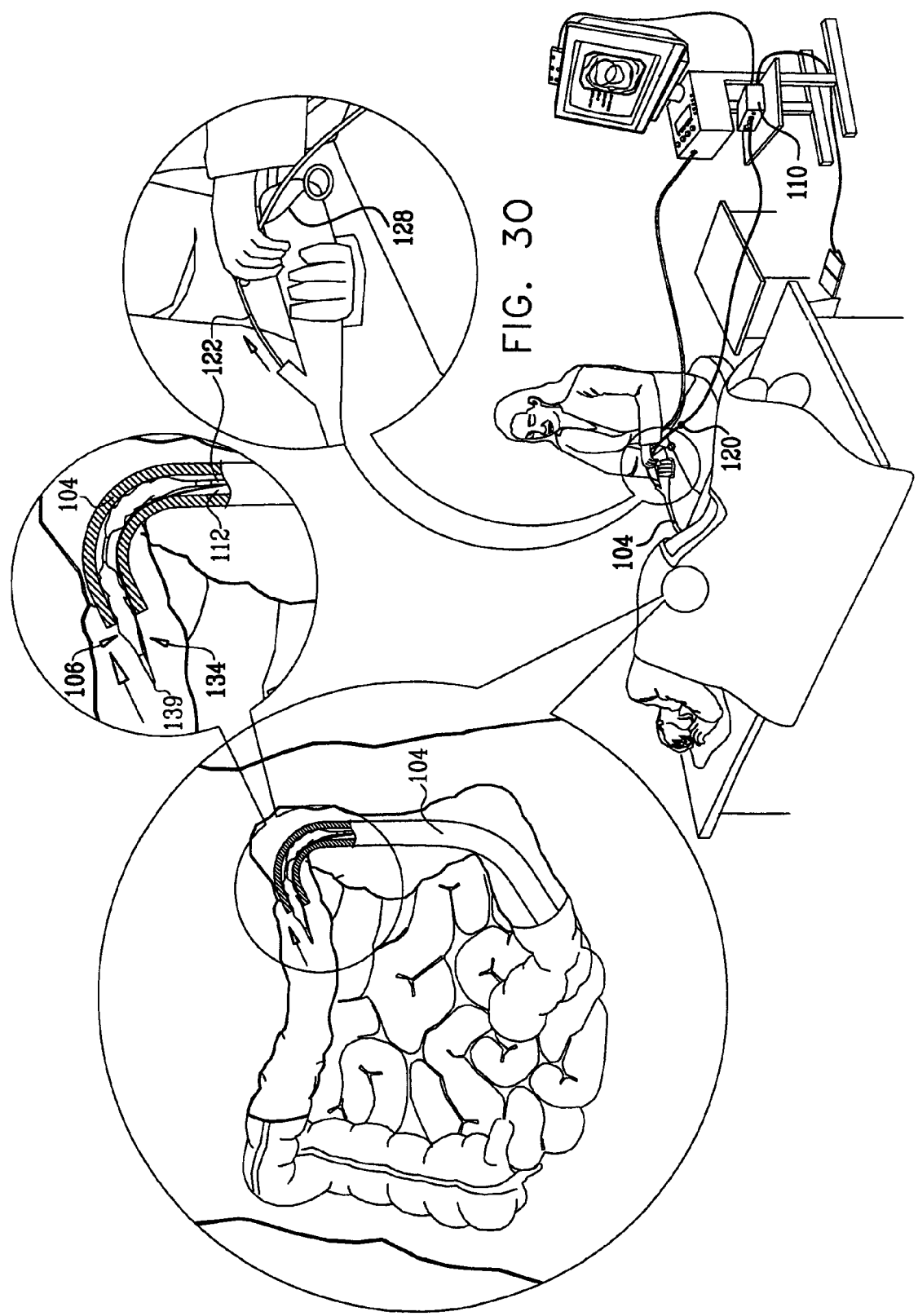

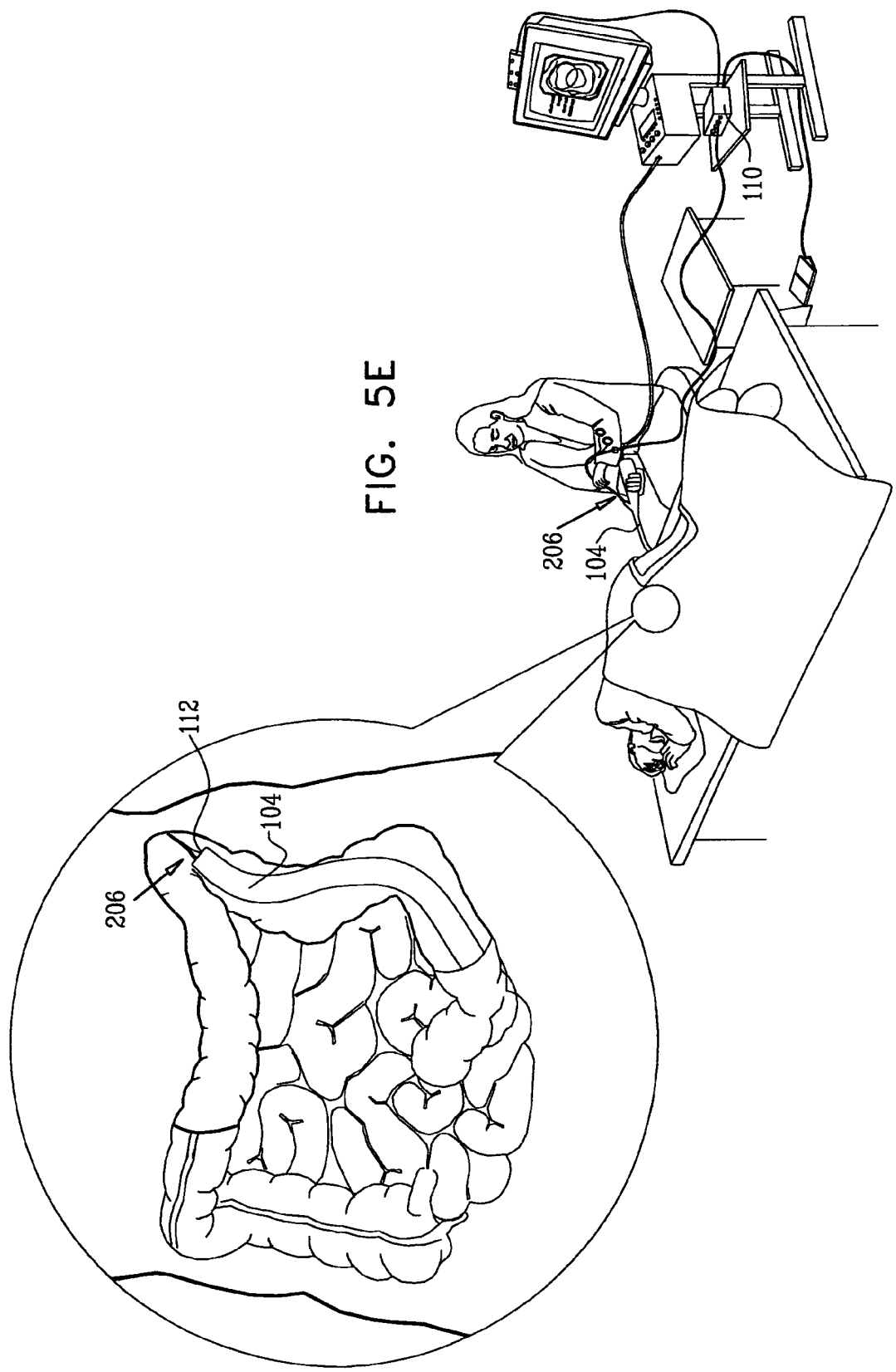

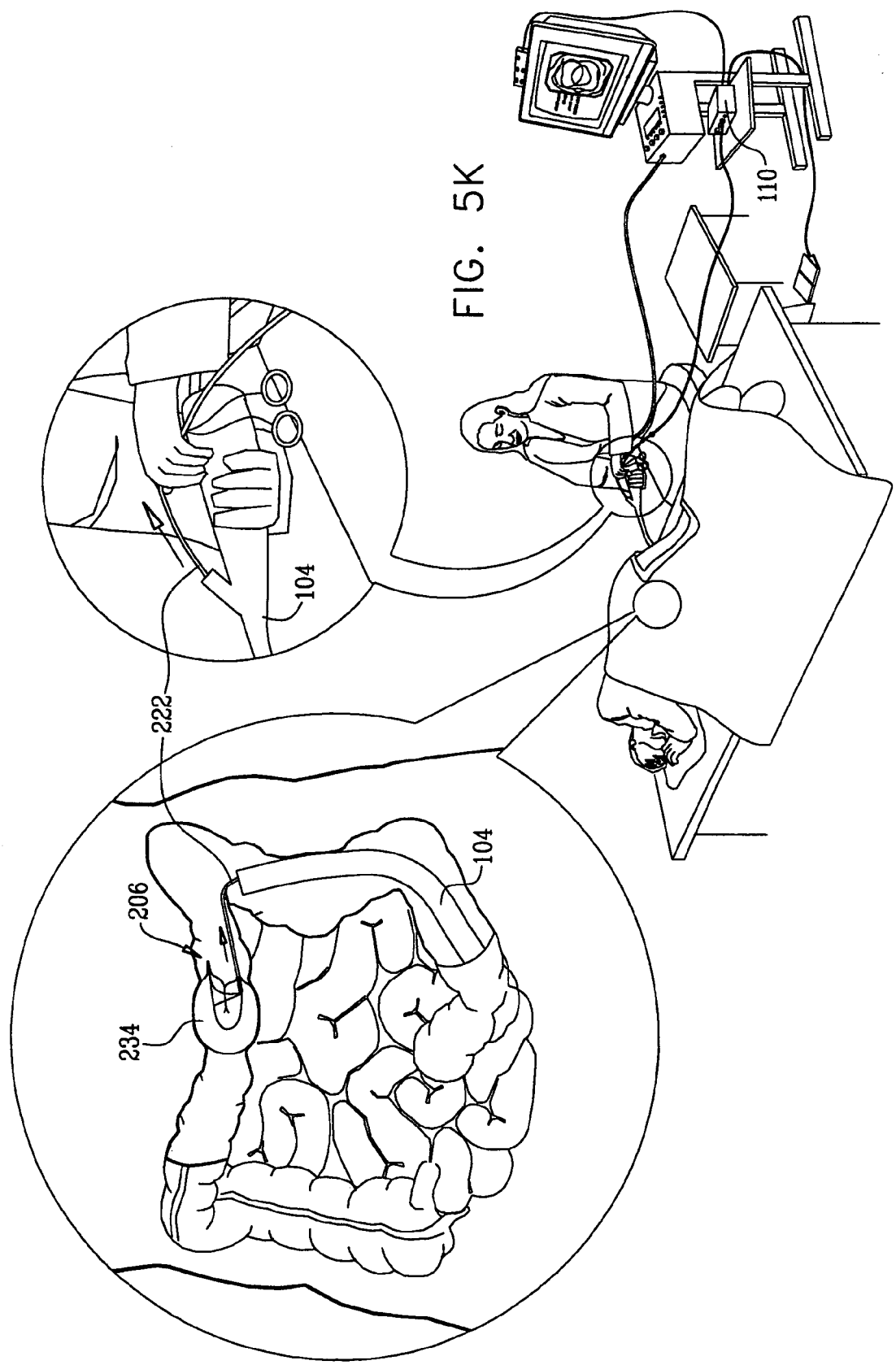

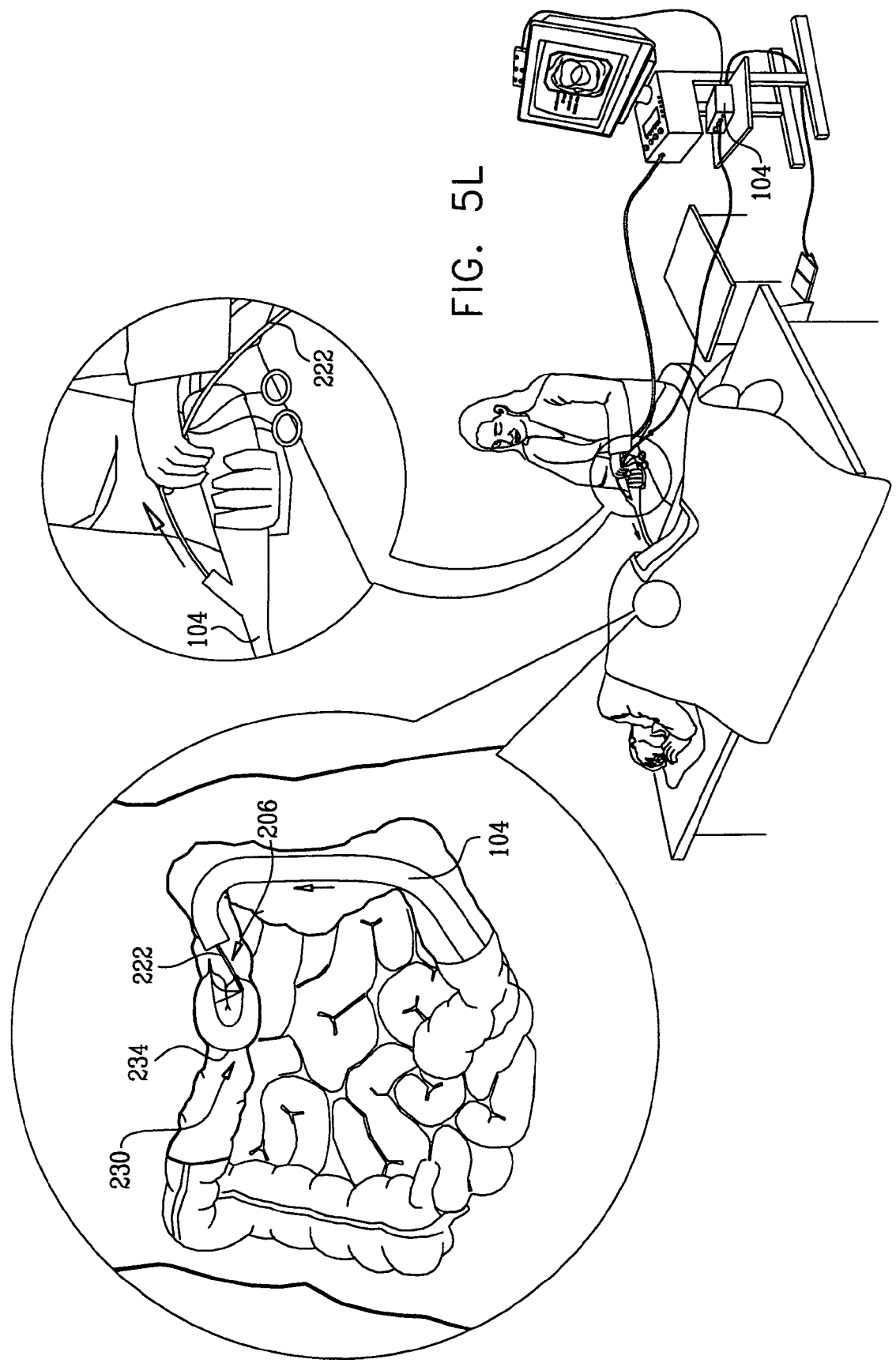

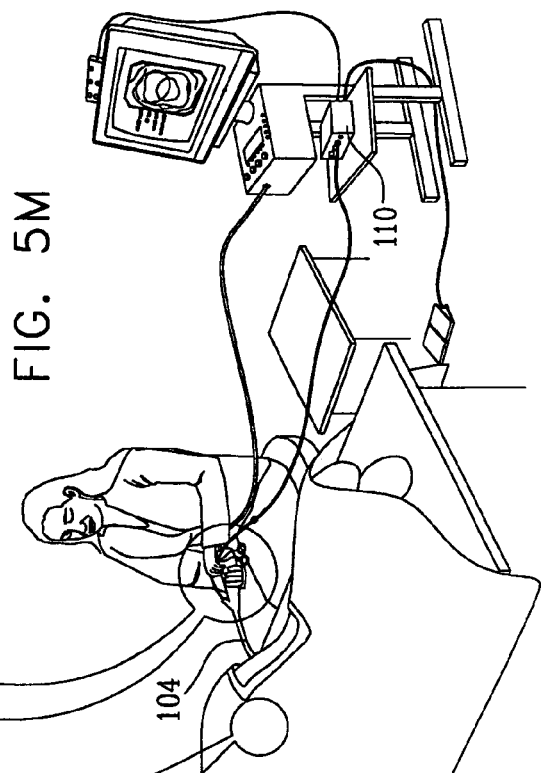
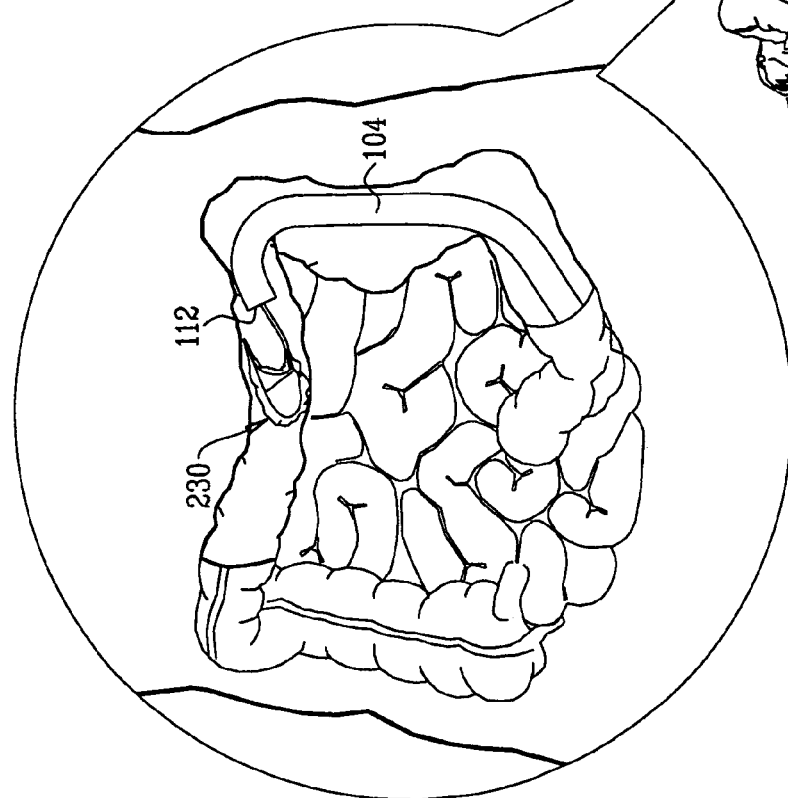
FIG. 5M

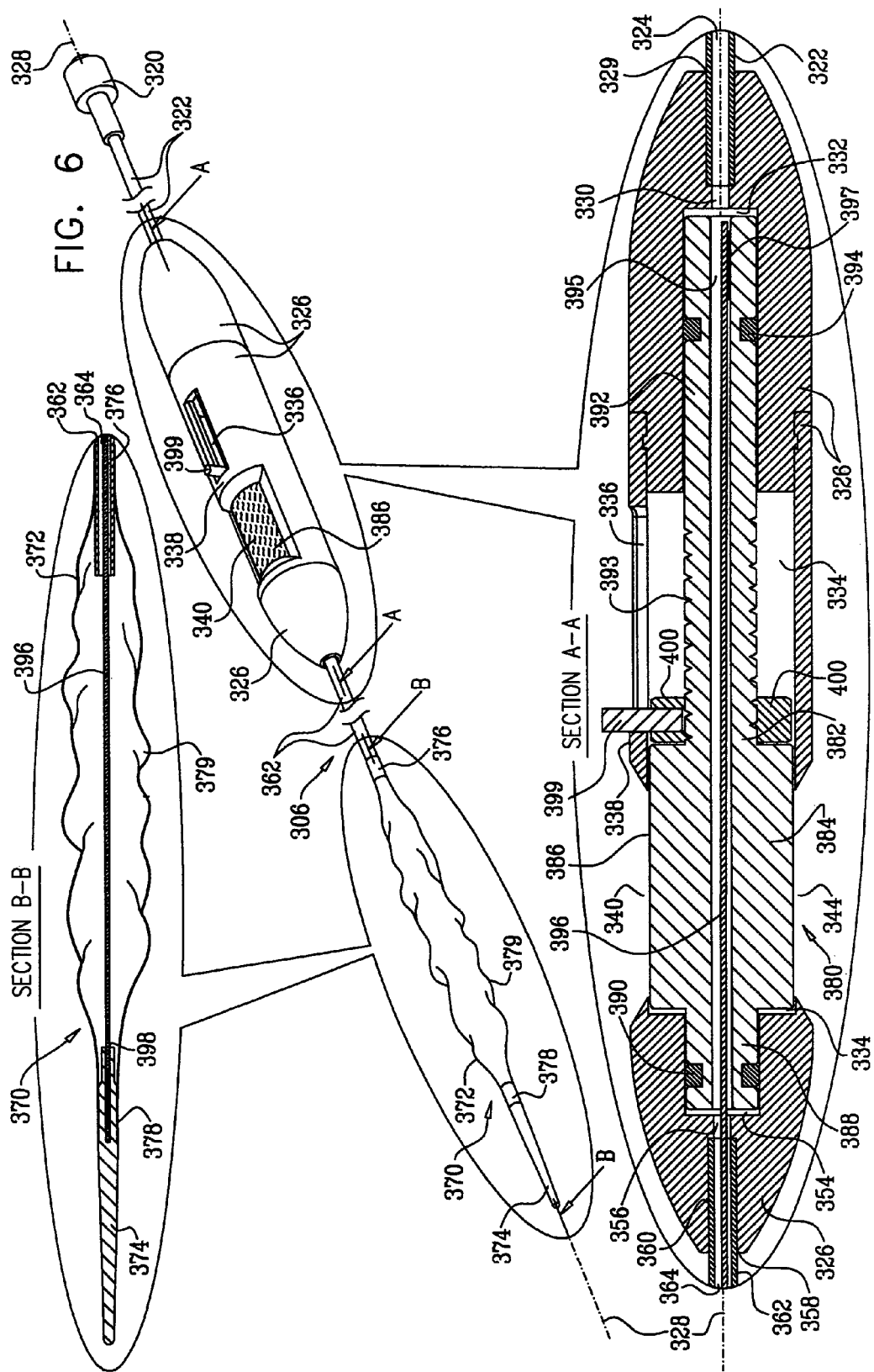

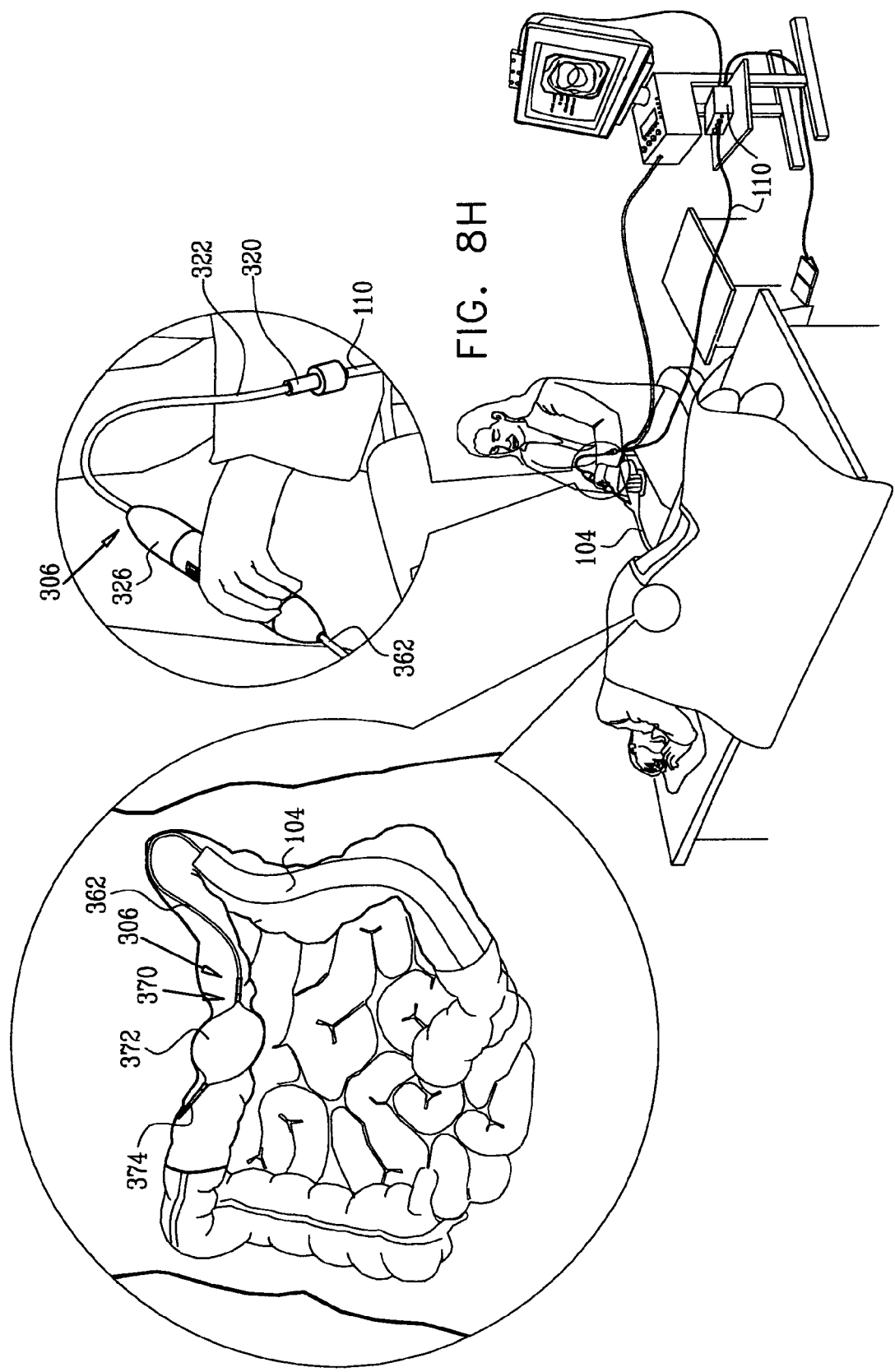

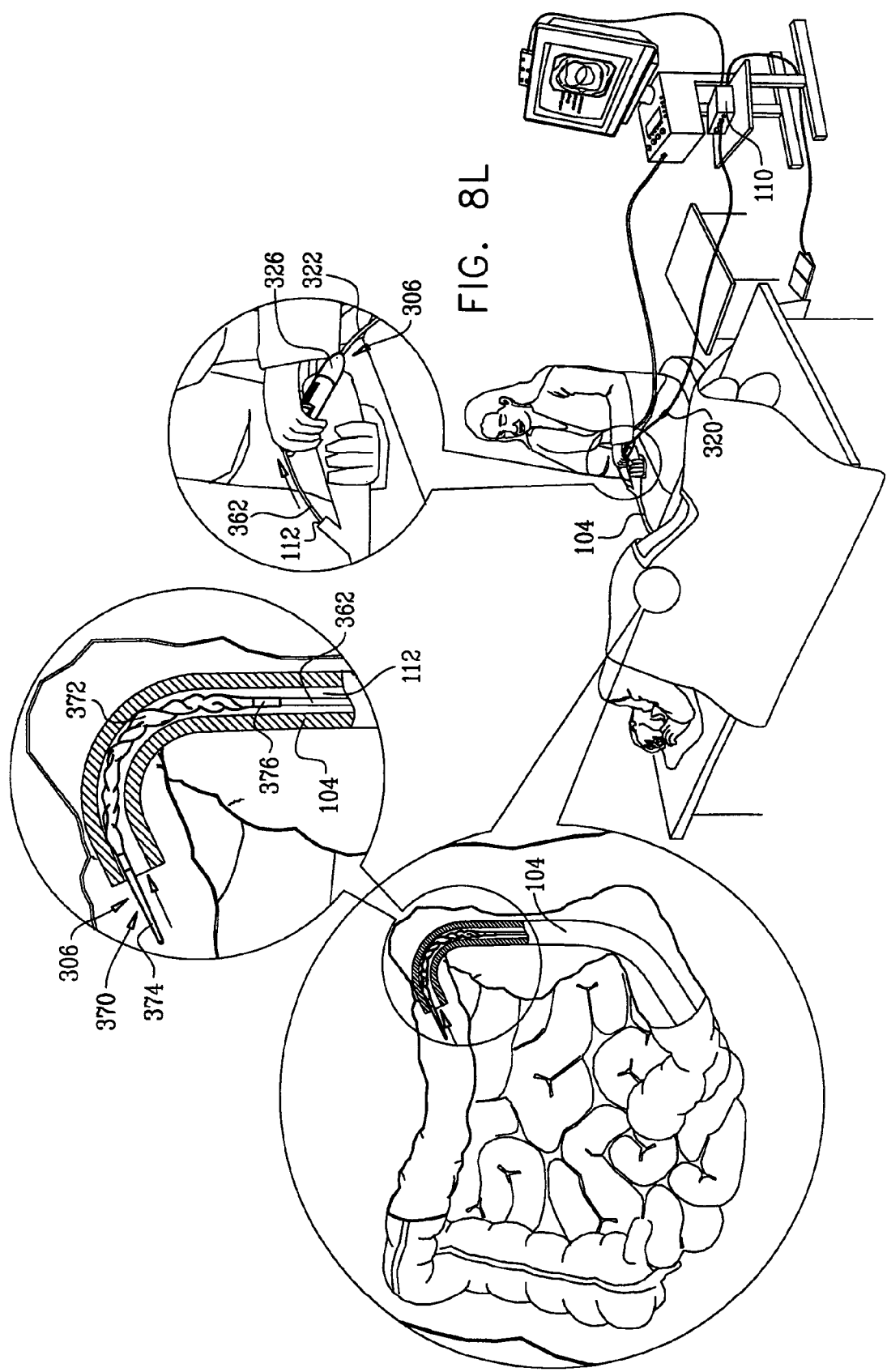

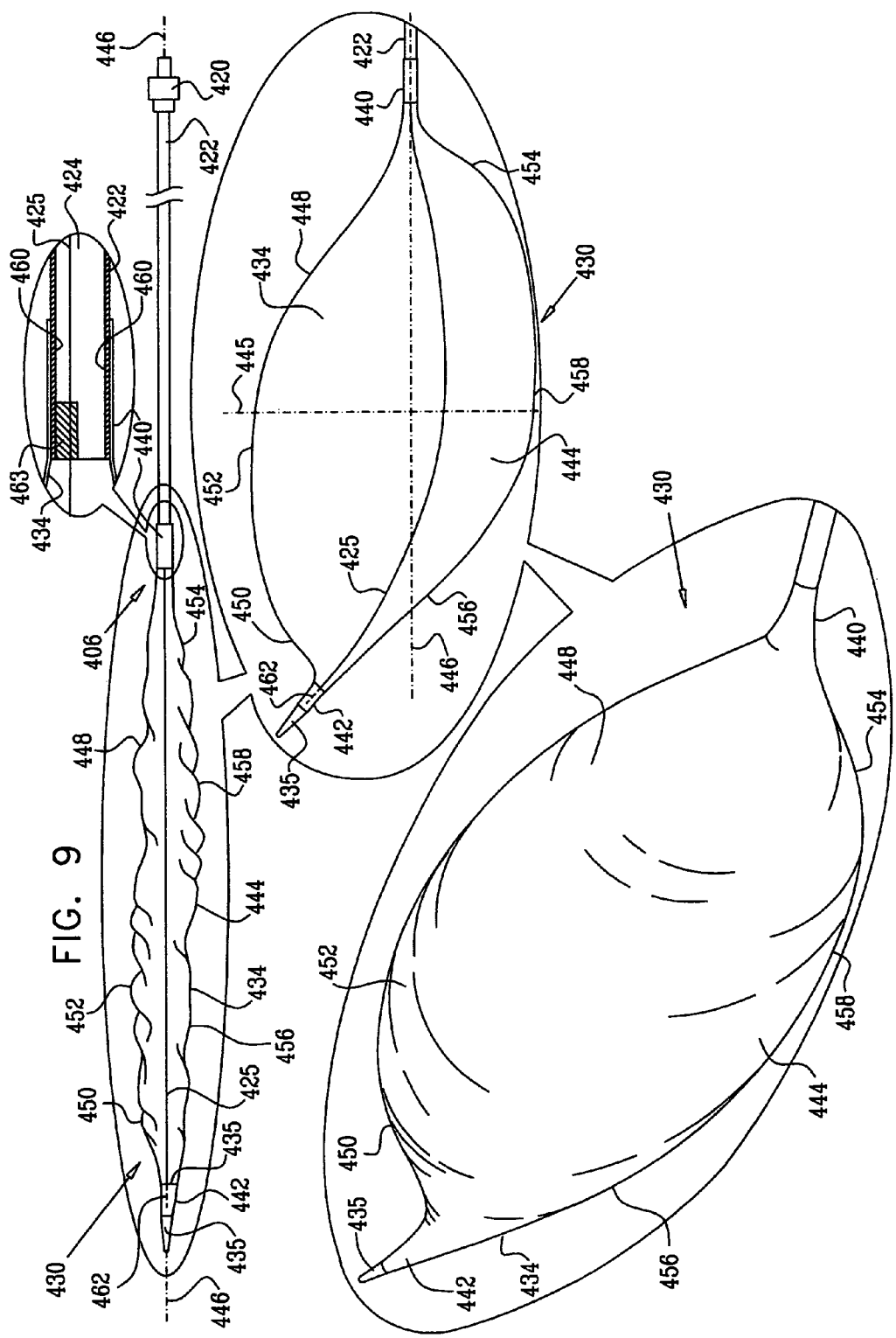

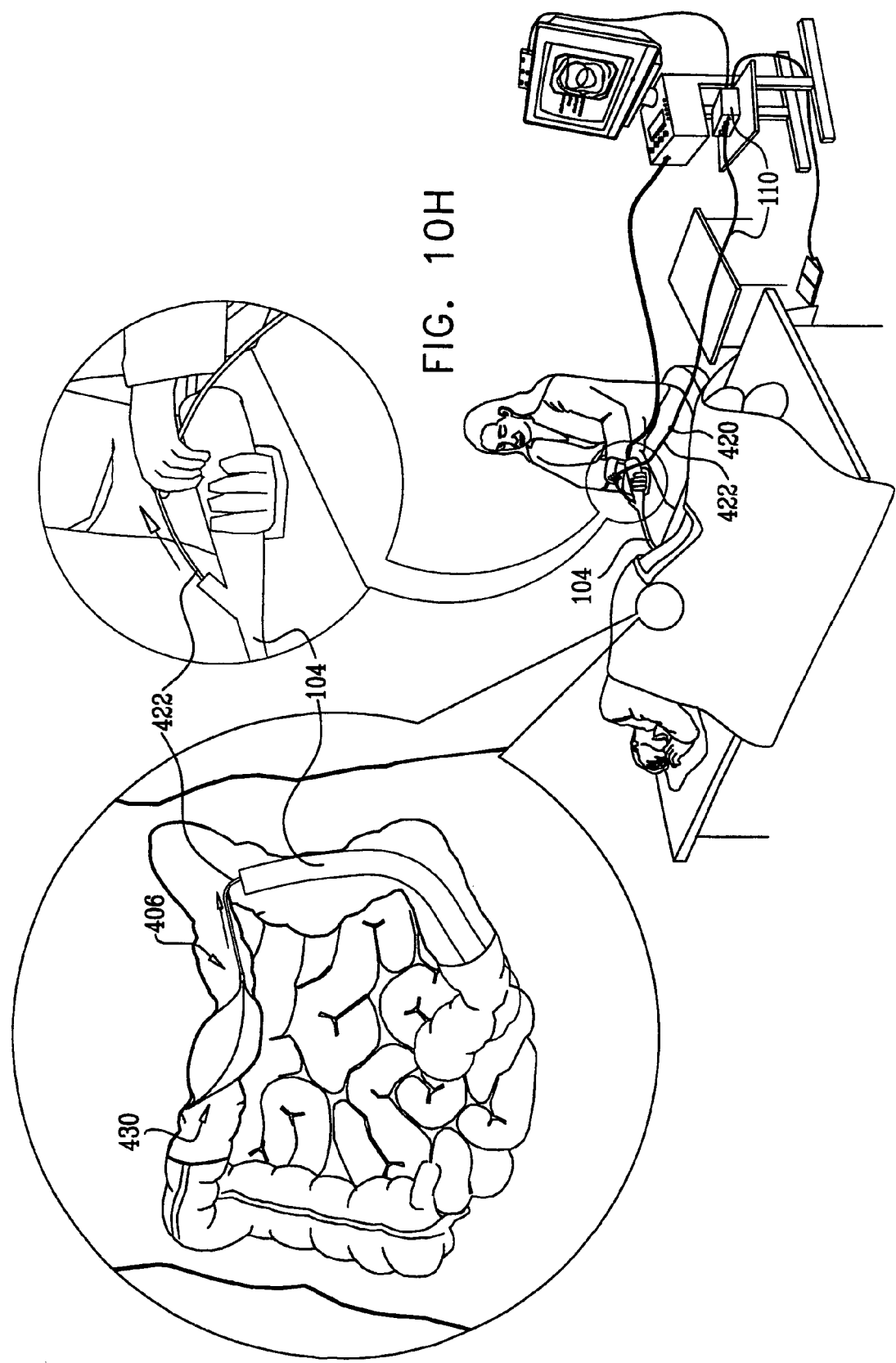

ANCHORING ASSEMBLIES FOR ENDOSCOPES

REFERENCE TO RELATED APPLICATIONS

Reference is made to U.S. Provisional Patent Application Ser. No. 61/213,320, filed May 29, 2009 and entitled "Variable Shape Balloon Accessory," U.S. Provisional Patent Application Ser. No. 61/282,501, filed Feb. 22, 2010 and entitled "A Variable-Stiffness Balloon Catheter Having A High Inflated/Deflated Diameter Ratio," and U.S. Provisional Patent Application Ser. No. 61/282,621, filed Mar. 9, 2010 and entitled "Complex Balloon Catheter With External Manipulation," the disclosures of which are hereby incorporated by reference and priorities of which are hereby claimed pursuant to 35 U.S.C. 33 CFR 1.38(a) (4) and (5)(i).

Reference is also made to applicant's copending PCT Application No. PCT/IL2005/000152, filed Feb. 7, 2005; PCT Application No. PCT/IL2005/000849, filed Aug. 8, 2005; PCT Application No. PCT/IL2007/000600, filed May 17, 2007; PCT Application No. PCT/IL2007/000832, filed Jul. 4, 2007; PCT Application No. PCT/IL2008/000687, filed May 20, 2008; PCT Application No. PCT/IL2009/000322, filed Mar. 23, 2009; and PCT Application No. PCT/IL2009/000940, filed Oct. 1, 2009, the disclosures of which are hereby incorporated by reference.

FIELD OF THE INVENTION

The present invention relates to endoscope systems generally.

BACKGROUND OF THE INVENTION

The following patent publications and commercially available products are believed to represent the current state of the art:

U.S. Pat. Nos. 3,837,347; 4,040,413; 4,148,307; 4,176,662; 4,195,637; 4,261,339; 4,453,545; 4,616,652; 4,676,228; 4,862,874; 4,917,088; 5,135,487; 5,259,366; 5,593,419; 6,007,482; 6,461,294; 6,585,639; 6,663,589; and 6,702,735;

U.S. Patent Application publication Nos. 2003/0244361; 2004/0102681; 2005/0124856; 2005/0125005; 2005/0133453; 2005/0137457; 2005/0165233; 2005/0165273; 2006/0111610; and 2006/0161044;

Japanese Patent Application publication No. JP2003-250896; and

Double Balloon Endoscope product, including EC-450BI5 colonoscope, TS-13101 overtube and BS-2 front balloon, which interface with balloon pump controller BP-20 and EPX-4400HD video system, all commercially available from Fujinon Inc., of 10 High Point Drive, Wayne, N.J., USA; and,

SUMMARY OF THE INVENTION

The present invention seeks to provide improved anchoring assemblies for operation with elongate articles such as endoscopes.

There is thus provided in accordance with a preferred embodiment of the present invention an endoscope system including an endoscope having an instrument channel and an anchoring assembly including an inflatable/deflatable balloon assembly, the inflatable/deflatable balloon assembly being deflatable to a cross-sectional size sufficiently small to enable it to pass through the instrument channel and being positionable and inflatable without substantial stretching to have a dimension sufficiently large to enable it to anchor in the large intestine.

In accordance with a preferred embodiment of the present invention the instrument channel has an inner diameter which does not exceed 5.5 mm. Preferably, the instrument channel has an inner diameter which does not exceed 4.5 mm. Yet preferably, the instrument channel has an inner diameter which does not exceed 3.2 mm. Additionally or alternatively, the inflatable/deflatable balloon assembly is inflatable to a cross sectional dimension of at least 70 mm. Preferably, the inflatable/deflatable balloon assembly is inflatable to a cross sectional dimension of at least 60 mm. Yet preferably, the inflatable/deflatable balloon assembly is inflatable to a cross sectional dimension of at least 50 mm.

Additionally or alternatively, the dimension sufficiently large to enable it to anchor in the large intestine has a diameter at least 13 times greater than the inner diameter of the instrument channel. Additionally or alternatively, the inflatable/deflatable balloon assembly is positionable by placement thereof at an appropriate location in the large intestine. Preferably, the inflatable/deflatable balloon assembly is positionable by orientation thereof within the large intestine so as to realize an overall dimension which is sufficient for anchoring in the large intestine. Yet preferably, the inflatable/deflatable balloon assembly is positionable by being manipulated into a folded-over orientation within the large intestine for anchoring. Preferably, the inflatable/deflatable balloon assembly includes at least one inflatable/deflatable balloon formed of polyurethane.

Preferably, the inflatable/deflatable balloon assembly includes at least one balloon arrangeable, when deflated, in a first orientation along a deflated balloon axis and arrangeable by virtue of its being inflated, in a second asymmetrically shaped orientation along an inflated balloon axis, tilted with respect to the deflated balloon axis.

Additionally or alternatively, the anchoring assembly also includes a catheter and an operator controllable balloon assembly manipulator and the inflatable/deflatable balloon assembly includes at least one balloon arrangeable, when deflated, in a first orientation relative to a deflated balloon axis which extends generally parallel to the catheter and arrangeable by the manipulator and when inflated, in a second orientation different from the first orientation, thereby being positionable and inflatable without substantial stretching to have a dimension sufficiently large to enable it to anchor in the large intestine. Preferably, the second orientation is a folded-over orientation. Yet preferably, the at least one balloon includes a single balloon. Alternatively, the at least one balloon includes plural balloons joined by at least one flexible element.

Preferably, the anchoring assembly includes a flexible elongate element traversing the catheter and the inflatable/deflatable balloon assembly, and at least one manipulation element associated at a forward portion of the catheter with a forward portion of the flexible elongate element and at a rearward portion of the catheter with the balloon assembly manipulator. Preferably, the at least one manipulation element includes plural manipulation elements adapted for sequential orientation of the inflatable/deflatable balloon assembly in the second orientation. Yet preferably, at least one of the flexible elongate element and the at least one manipulation element includes an elongate wire. Additionally or alternatively, the at least one balloon includes at a rearward end thereof a rearward-most neck portion, and the inflatable/deflatable balloon assembly includes, forwardly of the at least one balloon, a tip element, and wherein the tip element is positioned rearwardly of the rearward-most neck portion when the at least one balloon is arranged in the second orientation.

Additionally or alternatively, the inflatable/deflatable balloon assembly includes a catheter and at least one balloon and wherein the anchoring assembly also includes an operator controllable balloon assembly manipulator, the operator controllable balloon assembly manipulator enabling selectable furling and unfurling of the at least one balloon, whereby the at least one balloon may be furled to a cross sectional size sufficiently small to enable it to pass through the instrument channel and the balloon may be unfurled and inflated to a cross sectional size sufficiently large to enable it to anchor in the large intestine, thereby being positionable and inflatable without substantial stretching to have a dimension sufficiently large to enable it to anchor in the large intestine. Preferably, the anchoring assembly also includes a catheter and an operator controllable balloon assembly manipulator operative for manipulating the inflatable/deflatable balloon assembly to assume a selectable stiffness.

There is also provided in accordance with another preferred embodiment of the present invention, for use with an endoscope having an instrument channel, an anchoring assembly including an inflatable/deflatable balloon assembly, the inflatable/deflatable balloon assembly being deflatable to a cross-sectional size sufficiently small to enable it to pass through the instrument channel and being positionable and inflatable without substantial stretching to have a dimension sufficiently large to enable it to anchor in the large intestine.

In accordance with a preferred embodiment of the present invention, the instrument channel has an inner diameter which does not exceed 5.5 mm. Preferably, the instrument channel has an inner diameter which does not exceed 3.2 mm. Yet preferably, the inflatable/deflatable balloon assembly is inflatable to a cross sectional dimension of at least 70 mm. Alternatively, the inflatable/deflatable balloon assembly is inflatable to a cross sectional dimension of at least 60 mm. Yet alternatively, the inflatable/deflatable balloon assembly is inflatable to a cross sectional dimension of at least 50 mm. Additionally or alternatively, the dimension sufficiently large to enable it to anchor in the large intestine has a diameter at least 13 times greater than the inner diameter of the instrument channel.

Preferably, the inflatable/deflatable balloon assembly is positionable by placement thereof at an appropriate location in the large intestine. Yet preferably, the inflatable/deflatable balloon assembly is positionable by orientation thereof within the large intestine so as to realize an overall dimension which is sufficient for anchoring in the large intestine. Preferably, the inflatable/deflatable balloon assembly is positionable by being manipulated into a folded-over orientation within the large intestine for anchoring. Yet preferably, the inflatable/deflatable balloon assembly includes at least one inflatable/deflatable balloon formed of polyurethane.

Additionally or alternatively, the inflatable/deflatable balloon assembly includes at least one balloon arrangeable, when deflated, in a first orientation along a deflated balloon axis and arrangeable by virtue of its being inflated, in a second asymmetrically shaped orientation along an inflated balloon axis, tilted with respect to the deflated balloon axis. Preferably, the anchoring assembly also includes a catheter and an operator controllable balloon assembly manipulator and the inflatable/deflatable balloon assembly includes at least one balloon arrangeable, when deflated, in a first orientation relative to a deflated balloon axis which extends generally parallel to the catheter and arrangeable by the manipulator and when inflated, in a second orientation different from the first orientation, thereby being positionable and inflatable without substantial stretching to have a dimension sufficiently large to enable it to anchor in the large intestine. Preferably, the second orientation is a folded-over orientation. Yet preferably, the at least one balloon includes a single balloon. Alternatively, the at least one balloon includes plural balloons joined by at least one flexible element.

Preferably, the anchoring assembly includes a flexible elongate element traversing the catheter and the inflatable/deflatable balloon assembly, and at least one manipulation element associated at a forward portion of the catheter with a forward portion of the flexible elongate element and at a rearward portion of the catheter with the balloon assembly manipulator. Preferably, the at least one manipulation element includes plural manipulation elements adapted for sequential orientation of the inflatable/deflatable balloon assembly in the second orientation. Yet preferably, at least one of the flexible elongate element and the at least one manipulation element includes an elongate wire. Additionally or alternatively, the at least one balloon includes at a rearward end thereof a rearward-most neck portion, and the inflatable/deflatable balloon assembly includes, forwardly of the at least one balloon, a tip element, and wherein the tip element is positioned rearwardly of the rearward-most neck portion when the at least one balloon is arranged in the second orientation.

Preferably, the inflatable/deflatable balloon assembly includes a catheter and at least one balloon and wherein the anchoring assembly also includes an operator controllable balloon assembly manipulator, the operator controllable balloon assembly manipulator enabling selectable furling and unfurling of the at least one balloon, whereby the at least one balloon may be furled to a cross sectional size sufficiently small to enable it to pass through the instrument channel and the balloon may be unfurled and inflated to a cross sectional size sufficiently large to enable it to anchor in the large intestine, thereby being positionable and inflatable without substantial stretching to have a dimension sufficiently large to enable it to anchor in the large intestine. Yet preferably, the anchoring assembly also includes a catheter and an operator controllable balloon assembly manipulator operative for manipulating the inflatable/deflatable balloon assembly to assume a selectable stiffness.

There is further provided in accordance with yet another preferred embodiment of the present invention an endoscope system including an endoscope having an instrument channel having an inner diameter and an anchoring assembly including an inflatable/deflatable balloon assembly including a catheter and at least one balloon, the anchoring assembly also including an operator controllable balloon assembly manipulator, the operator controllable balloon assembly manipulator enabling selectable furling and unfurling of the at least one balloon, whereby the at least one balloon may be furled to a cross sectional size sufficiently small to enable it to pass through the instrument channel and the balloon may be unfurled and inflated for anchoring in a location within a patient's body portion.

In accordance with a preferred embodiment of the present invention the at least one balloon when unfurled is inflatable without substantial stretching to have a dimension sufficiently large to enable it to anchor in a location within a patient's body portion having a diameter at least 13 times greater than the inner diameter of the instrument channel. Preferably, the instrument channel has an inner diameter which does not exceed 5.5 mm. Additionally or alternatively, the inflatable/deflatable balloon assembly is inflatable to a cross sectional dimension of at least 50 mm. Additionally or alternatively, the operator controllable balloon assembly manipulator is operative for manipulating the inflatable/deflatable balloon assembly to assume a selectable stiffness.

Preferably, the inflatable/deflatable balloon assembly, when in unfurled and inflated state, is deflatable and furlable to a cross sectional size sufficiently small to enable it to pass through the instrument channel. Additionally or alternatively, the inflatable/deflatable balloon assembly is positionable by orientation thereof within the large intestine so as to realize an overall dimension which is sufficient for anchoring in the large intestine. Preferably, the inflatable/deflatable balloon assembly is positionable by being manipulated into a folded-over orientation within the large intestine for anchoring. Yet preferably, the at least one balloon is arrangeable, when deflated, in a first orientation along a deflated balloon axis and arrangeable by virtue of its being inflated, in a second asymmetrically shaped orientation along an inflated balloon axis, tilted with respect to the deflated balloon axis.

There is also provided in accordance with still another preferred embodiment of the present invention, for use with an endoscope system including an endoscope having an instrument channel having an inner diameter, an anchoring assembly including an inflatable/deflatable balloon assembly including a catheter and at least one balloon, and an operator controllable balloon assembly manipulator, the operator controllable balloon assembly manipulator enabling selectable furling and unfurling of the at least one balloon, whereby the at least one balloon may be furled to a cross sectional size sufficiently small to enable it to pass through the instrument channel and the balloon may be unfurled and inflated for anchoring in a location within a patient's body portion.

In accordance with a preferred embodiment of the present invention, the at least one balloon when unfurled is inflatable without substantial stretching to have a dimension sufficiently large to enable it to anchor in a location within a patient's body portion having a diameter at least 13 times greater than the inner diameter of the instrument channel. Preferably, the instrument channel has an inner diameter which does not exceed 5.5 mm. Yet preferably, the inflatable/deflatable balloon assembly is inflatable to a cross sectional dimension of at least 50 mm. Additionally or alternatively, the operator controllable balloon assembly manipulator is operative for manipulating the inflatable/deflatable balloon assembly to assume a selectable stiffness. Additionally or alternatively, the inflatable/deflatable balloon assembly, when in unfurled and inflated state, is deflatable and furlable to a cross sectional size sufficiently small to enable it to pass through the instrument channel.

Preferably, the inflatable/deflatable balloon assembly is positionable by orientation thereof within the large intestine so as to realize an overall dimension which is sufficient for anchoring in the large intestine. Preferably, the inflatable/deflatable balloon assembly is positionable by being manipulated into a folded-over orientation within the large intestine for anchoring. Additionally or alternatively, the at least one balloon is arrangeable, when deflated, in a first orientation along a deflated balloon axis and arrangeable by virtue of its being inflated, in a second asymmetrically shaped orientation along an inflated balloon axis, tilted with respect to the deflated balloon axis.

There is also provided in accordance with yet another preferred embodiment of the present invention an endoscope system including an endoscope having an instrument channel having an inner diameter, and an anchoring assembly including an inflatable/deflatable balloon assembly including at least one balloon, the anchoring assembly also including a catheter and an operator controllable balloon assembly manipulator, and the inflatable/deflatable balloon assembly including at least one balloon arrangeable, when deflated, in a first orientation relative to a deflated balloon axis which extends generally parallel to the catheter and arrangeable by the manipulator and when inflated, in a second orientation different from the first orientation, thereby being positionable and inflatable without substantial stretching to have a dimension sufficiently large to enable it to anchor in a location within a patient's body portion.

In accordance with a preferred embodiment of the present invention, the second orientation is a folded-over orientation. Preferably, the at least one balloon includes a single balloon. Alternatively, the at least one balloon includes plural balloons joined by at least one flexible element. Additionally or alternatively, the at least one balloon is manipulatable and inflatable without substantial stretching to have a dimension sufficiently large to enable it to anchor in a location within a patient's body portion having a diameter at least 13 times greater than the inner diameter of the instrument channel. Preferably, the instrument channel has an inner diameter which does not exceed 5.5 mm. Yet preferably, the inflatable/deflatable balloon assembly is inflatable to a cross sectional dimension of at least 60 mm.

Preferably, the anchoring assembly includes a flexible elongate element traversing the catheter and the inflatable/deflatable balloon assembly, and at least one manipulation element associated at a forward portion of the catheter with a forward portion of the flexible elongate element and at a rearward portion of the catheter with the balloon assembly manipulator.

Additionally or alternatively, the operator controllable balloon assembly manipulator enabling selectable furling and unfurling of the at least one balloon, whereby the at least one balloon may be furled to a cross sectional size sufficiently small to enable it to pass through the instrument channel and the balloon may be unfurled and inflated for anchoring in a location within a patient's body portion. Preferably, the operator controllable balloon assembly manipulator is operative for manipulating the inflatable/deflatable balloon assembly to assume a selectable stiffness.

There is further provided in accordance with still another preferred embodiment of the present invention, for use with an endoscope system including an endoscope having an instrument channel having an inner diameter, an anchoring assembly including an inflatable/deflatable balloon assembly including a catheter and an operator controllable balloon assembly manipulator, the inflatable/deflatable balloon assembly including at least one balloon arrangeable, when deflated, in a first orientation relative to a deflated balloon axis which extends generally parallel to the catheter and arrangeable by the manipulator and when inflated, in a second orientation different from the first orientation, thereby being positionable and inflatable without substantial stretching to have a dimension sufficiently large to enable it to anchor in a location within a patient's body portion.

In accordance with a preferred embodiment of the present invention, the second orientation is a folded-over orientation. Preferably, the at least one balloon includes a single balloon. Alternatively, the at least one balloon includes plural balloons joined by at least one flexible element. Additionally or alternatively, the at least one balloon is manipulatable and inflatable without substantial stretching to have a dimension sufficiently large to enable it to anchor in a location within a patient's body portion having a diameter at least 13 times greater than the inner diameter of the instrument channel. Preferably, the instrument channel has an inner diameter which does not exceed 5.5 mm. Yet preferably, the inflatable/deflatable balloon assembly is inflatable to a cross sectional dimension of at least 60 mm.

Preferably, the anchoring assembly includes a flexible elongate element traversing the catheter and the inflatable/deflatable balloon assembly, and at least one manipulation element associated at a forward portion of the catheter with a forward portion of the flexible elongate element and at a rearward portion of the catheter with the balloon assembly manipulator.

Additionally or alternatively, the operator controllable balloon assembly manipulator enabling selectable furling and unfurling of the at least one balloon, whereby the at least one balloon may be furled to a cross sectional size sufficiently small to enable it to pass through the instrument channel and the balloon may be unfurled and inflated for anchoring in a location within a patient's body portion. Preferably, the operator controllable balloon assembly manipulator is operative for manipulating the inflatable/deflatable balloon assembly to assume a selectable stiffness.

There is further provided in accordance with yet another preferred embodiment of the present invention an endoscope system including an endoscope having an instrument channel having an inner diameter, and an anchoring assembly including an inflatable/deflatable balloon assembly including a catheter and at least one balloon arrangeable, when deflated, in a first orientation along a deflated balloon axis and arrangeable by virtue of its being inflated, in a second asymmetrically shaped orientation along an inflated balloon axis, tilted with respect to the deflated balloon axis.

In accordance with a preferred embodiment of the present invention, the inflatable/deflatable balloon assembly being deflatable to a cross-sectional size sufficiently small to enable it to pass through the instrument channel. Preferably, the instrument channel has an inner diameter which does not exceed 5 mm. Preferably, the inflatable/deflatable balloon assembly is inflatable to a cross sectional dimension of at least 60 mm. Yet preferably, the at least one balloon is inflatable without substantial stretching to have a dimension sufficiently large to enable it to anchor in a location within a patient's body portion having a diameter at least 13 times greater than the inner diameter of the instrument channel.

There is further provided in accordance with still another preferred embodiment of the present invention, for use with an endoscope system including an endoscope having an instrument channel having an inner diameter, an anchoring assembly Including an inflatable/deflatable balloon assembly, the inflatable/deflatable balloon assembly including a catheter and at least one balloon arrangeable, when deflated, in a first orientation along a deflated balloon axis and arrangeable by virtue of its being inflated, in a second asymmetrically shaped orientation along an inflated balloon axis, tilted with respect to the deflated balloon axis.

In accordance with a preferred embodiment of the present invention, the inflatable/deflatable balloon assembly being deflatable to a cross-sectional size sufficiently small to enable it to pass through the instrument channel. Preferably, the instrument channel has an inner diameter which does not exceed 5 mm. Additionally or alternatively, the inflatable/deflatable balloon assembly is inflatable to a cross sectional dimension of at least 60 mm. Preferably, the at least one balloon is inflatable without substantial stretching to have a dimension sufficiently large to enable it to anchor in a location within a patient's body portion having a diameter at least 13 times greater than the inner diameter of the instrument channel.

There is also provided in accordance with another preferred embodiment of the present invention a method for anchoring of an anchoring assembly at a desired location within a patient's body, the method including the steps of inserting an endoscope including an instrument channel having an inner diameter into a patient's body, and inserting the anchoring assembly, including an inflatable/deflatable balloon assembly, through the instrument channel into a patient's body, the inserting including prior to passage of the anchoring assembly through the instrument channel, deflating the inflatable/deflatable balloon assembly to a cross-sectional size sufficiently small to enable it to pass through the instrument channel, and subsequent to passage of the inflatable/deflatable balloon assembly through the instrument channel, positioning and inflating the inflatable/deflatable balloon assembly substantially without stretching of the balloon assembly to have a dimension at least 13 times greater than the inner diameter of the instrument channel.

In accordance with a preferred embodiment of the present invention, the method for anchoring of an anchoring assembly at a desired location within a patient's body also includes, prior to the inflating the inflatable/deflatable balloon assembly, the step of manipulating the inflatable/deflatable balloon assembly within the patient's body by employing an operator controllable balloon assembly manipulator outside of the patient's body. Preferably, manipulating the inflatable/deflatable balloon assembly includes folding over the inflatable/deflatable balloon assembly. Additionally or alternatively, manipulating the inflatable/deflatable balloon assembly includes unfurling the inflatable/deflatable balloon assembly.

Preferably, the method also includes, following the inserting the anchoring assembly, the steps of deflating the inflatable/deflatable balloon assembly within the patient's body and removing the anchoring assembly from the patient's body through the instrument channel. Additionally or alternatively, the method also includes the step of furling the inflatable/deflatable balloon assembly by employing an operator controllable balloon assembly manipulator outside of the patient's body.

Preferably, inserting the anchoring assembly including an inflatable/deflatable balloon assembly through the instrument channel into a patient's body includes inserting the anchoring assembly into a large intestine of a patient.

BRIEF DESCRIPTION OF THE DRAWINGS

The present invention will be understood and appreciated more fully from the following detailed description, taken in conjunction with the drawings in which:

FIGS. 3A, 3B, 3C, 3D, 3E, 3F, 3G, 3H, 3I, 3J, 3K, 3L, 3M, 3N and 3O are simplified pictorial illustrations of operation of the endoscope system of FIG. 1 and the anchoring assembly of FIG. 2 in accordance with a preferred embodiment of the present invention;

FIGS. 5A, 5B, 5C, 5D, 5E, 5F, 5G, 5H, 5I, 5J, 5K, 5L, 5M, 5N and 5O are simplified pictorial illustrations of operation of the endoscope system of FIG. 1 and the anchoring assembly of FIG. 4 in accordance with a preferred embodiment of the present invention;

FIG. 6 is a simplified partially pictorial, partially sectional illustration of an anchoring assembly associatable with an endoscope in accordance with yet another preferred embodiment of the present invention;

FIGS. 8A, 8B, 8C, 8D, 8E, 8F, 8G, 8H, 8I, 8J, 8K and 8L are simplified pictorial illustrations of the endoscope system of FIG. 1 and the anchoring assembly of FIGS. 6 and 7A-7C in accordance with a preferred embodiment of the present invention;

FIG. 9 is a simplified partially pictorial, partially sectional illustration an anchoring assembly associatable with an endoscope in accordance with a preferred embodiment of the present invention; and FIGS. 10A, 10B, 10C, 10D, 10E, 10F, 10G, 10H, 10I, 10J and 10K are simplified pictorial illustrations of operation of the endoscope system of FIG. 1 and the anchoring assembly of FIG. 9 in accordance with a preferred embodiment of the present invention.

DETAILED DESCRIPTION OF PREFERRED EMBODIMENTS

The terms "endoscope" and "endoscopy" are used throughout in a manner somewhat broader than their customary meaning and refer to apparatus and methods which operate within body cavities, passageways and the like, such as, for example, the small intestine and the large intestine. Although these terms normally refer to visual inspection, as used herein they are not limited to applications which employ visual inspection and refer as well to apparatus, systems and methods which need not necessarily involve visual inspection.

The term "forward" refers to the remote end of an endoscope, accessory or tool furthest from the operator or to a direction facing such remote end.

The term "rearward" refers to the end portion of an endoscope, accessory or tool closest to the operator, typically outside an organ or body portion of interest or to a direction facing such end portion.

Figure 1:
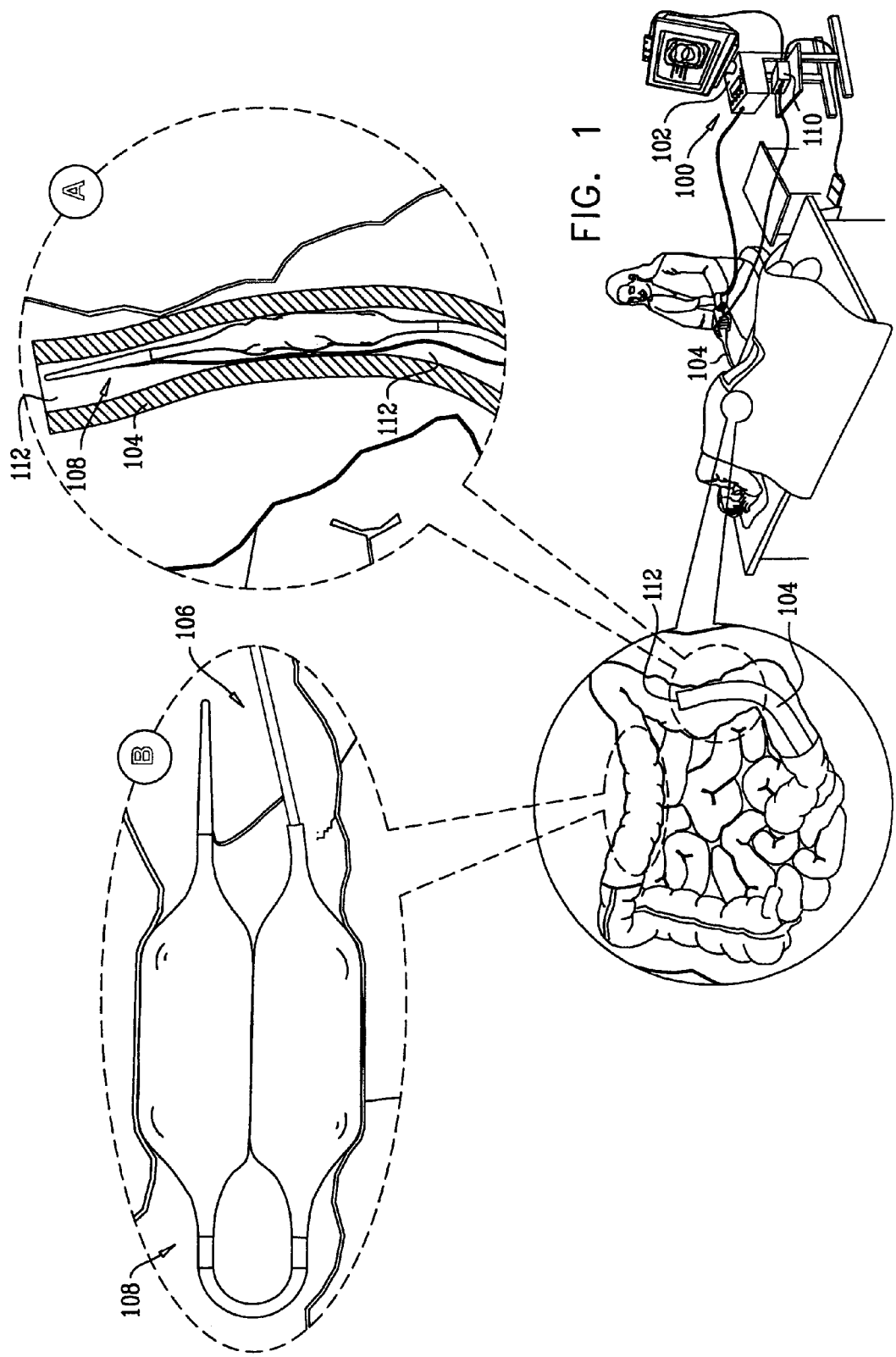
FIG. 1 is a simplified multi-stage mosaic illustration of an endoscope system constructed and operative in accordance with a preferred embodiment of the present invention.

Reference is now made to FIG. 1, which illustrate an endoscopy system 100 constructed and operative in accordance with a preferred embodiment of the present invention. The endoscopy system 100 preferably includes a console 102, such as a console including a EPK-1000 video processor and a SONY LMD-2140MD medical grade flat panel LCD monitor, all commercially available from Pentax Europe GmbH, 104 Julius-Vosseler St., 22527 Hamburg, Germany. The system 100 preferably includes a conventional flexible endoscope 104, such as an EC-3470LK video colonoscope or a VSB-3430K video enteroscope which are commercially available from Pentax Europe GmbH, 104 Julius-Vosseler St. 22527 Hamburg, Germany.

In accordance with a preferred embodiment of the invention, an anchoring assembly 106 comprising a catheter including an inflatable/deflatable balloon assembly 108 is operatively associated with endoscope 104 as shown generally in FIG. 1. Anchoring assembly 106 and inflatable/deflatable balloon assembly 108 may have various configurations, preferred examples of which are described hereinbelow. The configuration of inflatable/deflatable balloon assembly 108 shown in FIG. 1 is one example of the various configurations.

An inflation/deflation control assembly 110, preferably a model NAVIAID ASU commercially available from Smart Medical Systems Ltd. of Raanana, Israel, is preferably operatively associated with the inflatable/deflatable balloon assembly 108 and is preferably employed by an operator in the operation of the inflatable/deflatable balloon assembly 108.

As illustrated pictorially in FIG. 1, it is a particular feature of the present invention that the inflatable/deflatable balloon assembly 108 is deflatable to a cross sectional size sufficiently small to enable it to pass through an instrument channel 112 of a conventional endoscope such as endoscope 104 as shown at A in FIG. 1 and is positionable in the large intestine and inflatable without substantial stretching to have a dimension sufficiently large to enable it to anchor in the large intestine, typically as shown at B in FIG. 1. Preferably, the inflatable/deflatable balloon assembly is deflatable both prior to and subsequent to anchoring for passage through the instrument channel 112. Positioning of the inflatable/deflatable balloon assembly 108 may include placement of the balloon assembly 108 at an appropriate location in the large intestine and may optionally also include orientation of the balloon assembly within the large intestine so as to realize an overall dimension which is sufficient for anchoring in the large intestine. For example, in the embodiments of FIGS. 1-5O, the balloon assembly is in a folded-over orientation for anchoring, while in the embodiments of FIGS. 6-10K this is not the case.

In a preferred embodiment of the present invention, the balloon assembly 108 is deflatable to a cross sectional diameter of between 2.5 and 3.8 mm which can pass through a correspondingly sized instrument channel of inner diameter between 3.0 and 4.5 mm and is positionable and inflatable without substantial stretching to a cross sectional diameter of between 55 and 90 mm, which allows anchoring in the large intestine at a location having an inner diameter of up to 75 mm, and typically between 30 and 60 mm.

According to another embodiment of the present invention, the balloon assembly 108 is deflatable to a cross sectional diameter of between 4.0 and 5.3 mm which can pass through a correspondingly sized instrument channel of inner diameter between 4.5 and 6.0 mm and is positionable and inflatable without substantial stretching to a cross sectional diameter of between 65 and 110 mm, which allows anchoring in the large intestine at a location having an inner diameter of up to 85 mm, and typically between 30 and 70 mm.

In accordance with a preferred embodiment of the present invention, the anchoring cross sectional dimension of the balloon assembly 108, when inflated and anchoring in the large intestine, is typically 13-17 times larger than the cross sectional diameter of balloon assembly 108 when deflated and inserted through the instrument channel 112 of endoscope 104.

It is appreciated that the inflatable/deflatable balloon assembly 108 may be formed of suitable well-known non-substantially-stretchable materials such as nylon or polyurethane.

Figure 2:
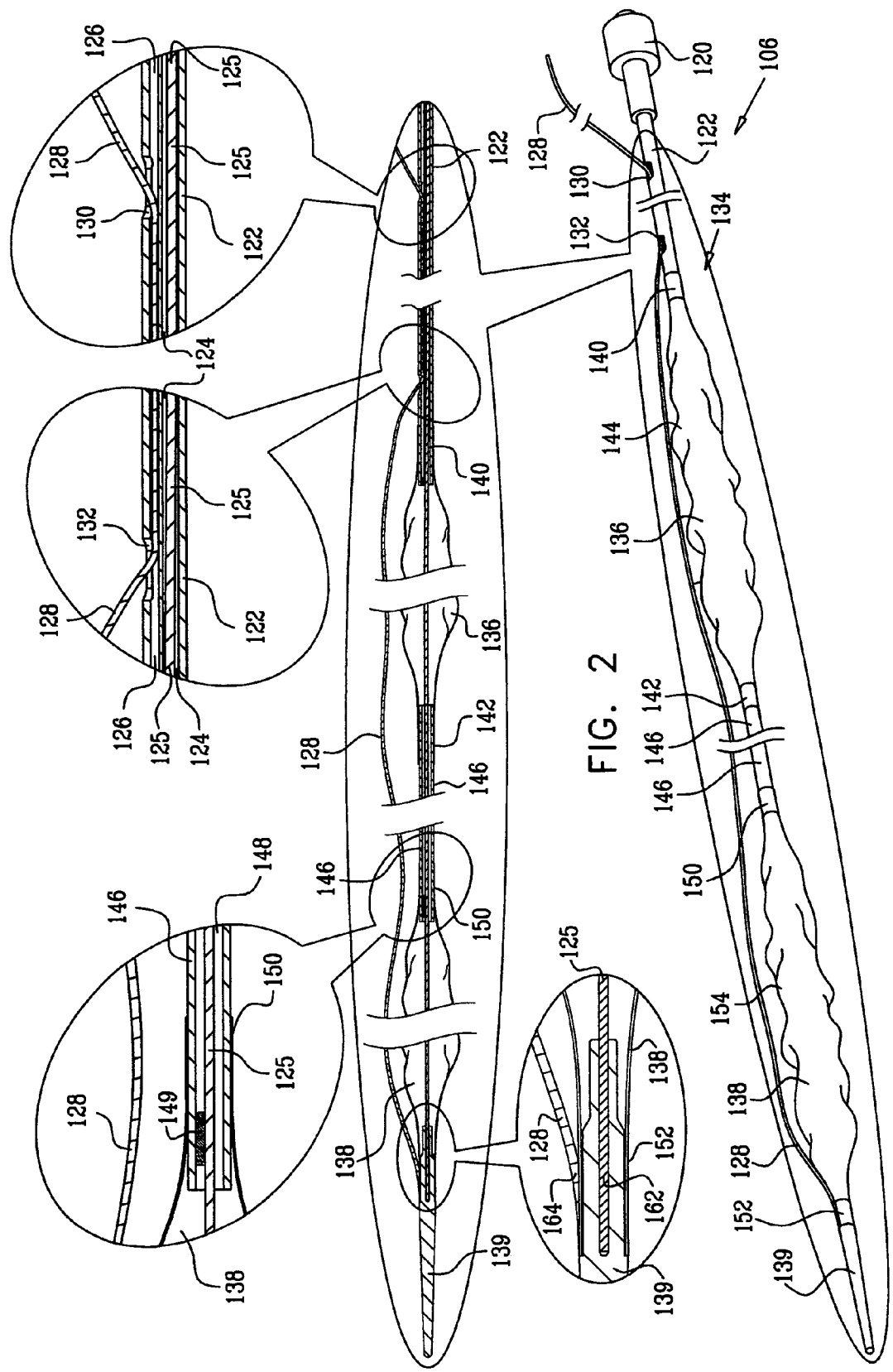
FIG. 2 is a simplified partially pictorial, partially sectional illustration of an anchoring assembly associatable with an endoscope in accordance with a preferred embodiment of the present invention.

Reference is now made to FIG. 2, which is a simplified partially pictorial, partially sectional illustration of an anchoring assembly associatable with an endoscope in accordance with a preferred embodiment of the present invention.

As seen in FIG. 2, the anchoring assembly 106 preferably comprises a connector 120 which is suitable for operative engagement with inflation/deflation control assembly 110 (FIG. 1). A multi-lumen tube 122 is preferably fixedly mounted on connector 120 and includes at least one lumen 124 for inflation/deflation, through which extends a flexible elongate element such as an elongate wire 125, and at least one lumen 126 for accommodating an elongate manipulation element, such as a manipulation wire 128. Elongate wire 125 is attached to connector 120 and thus is fixed with respect to multi-lumen tube 122.

Elongate wire 125 preferably is formed of a flexible metal, such as Nitinol or stainless steel. Manipulation wire 128 is preferably formed of a highly flexible, non-stretchable material such as nylon. Alternatively, manipulation wire 128 may be formed of a suitable metal, such as Nitinol.

Multi-lumen tube 122 preferably has an outer diameter of approximately 2.0-3.5 mm. Lumen 124 preferably has an inner diameter of approximately 1.0-1.8 mm. Lumen 126 preferably has an inner diameter of approximately 0.5-0.8 mm. Elongate wire 125 preferably has a diameter of approximately 0.3-0.9 mm. Manipulation wire 128 preferably has a diameter of approximately 0.1-0.3 mm.

Multi-lumen tube 122 is suitable for passage through the instrument channel 112 (FIG. 1) of a conventional endoscope and typically has an overall length of between 2 and 3 meters. Lumen 126 has openings 130 and 132 for passage therethrough of manipulation wire 128. Opening 130 is preferably located slightly forwardly of connector 120 and opening 132 is located slightly rearwardly of an inflatable/deflatable balloon assembly 134.

Balloon assembly 134 has a configuration similar to that of inflatable/deflatable balloon assembly 108 (FIG. 1) and includes first and second balloons 136 and 138 and a tip element 139. First balloon 136 preferably comprises a sleeve formed of non-substantially-stretchable nylon or polyurethane having respective rearward and forward neck portions 140 and 142 and a central portion 144, which when inflated has an approximate length of 40-80 mm and diameter of 35-45 mm. As seen in FIG. 2, rearward neck portion 140 of first balloon 136 is the rearward-most neck portion of balloon assembly 134.

Rearward neck portion 140 of first balloon 136 is sealingly mounted as by adhesive or ultrasonic welding onto a forward end of multi-lumen tube 122. Forward neck portion 142 of first balloon 136 is sealingly mounted as by adhesive or ultrasonic welding onto a rearward end of an intermediate tube 146. Intermediate tube 146 is a generally flexible tube, preferably of length between 40 and 90 mm and having an outer diameter of approximately 2.0-3.5 mm, and a central lumen 148, having a corresponding inner diameter of approximately 1.0-2.5 mm through which extends elongate wire 125, which is fixed thereto, as by an adhesive or mechanical attachment 149.

Second balloon 138 preferably comprises a sleeve formed of non-substantially-stretchable nylon or polyurethane having respective rearward and forward neck portions 150 and 152 and a central portion 154, which when inflated has an approximate length of 40-80 mm and diameter of 35-45 mm.

Rearward neck portion 150 of second balloon 138 is sealingly mounted as by adhesive or ultrasonic welding onto a forward end of intermediate tube 146. Forward neck portion 152 of second balloon 138 is sealingly mounted as by adhesive or ultrasonic welding onto a rearward end of tip element 139. Tip element 139 is generally flexible forward facing conical element, preferably of length between 5 and 40 mm and having maximum outer diameter of approximately 1.0-3.5 mm.

A forward end 162 of elongate wire 125 is fixed to tip element 139, preferably at a rearward end thereof as by adhesive.

A forward end 164 of manipulation wire 128 is preferably fixed to forward neck portion 152, or to tip element 139, preferably at an outside surface adjacent rearward end thereof as by adhesive or ultrasonic welding.

Reference is now made to FIGS. 3A, 3B, 3C, 3D, 3E, 3F, 3G, 3H, 3I, 3J, 3K, 3L, 3M, 3N and 3O, which are simplified pictorial illustrations of operation of the endoscope system of FIG. 1 and the anchoring assembly of FIG. 2 in accordance with a preferred embodiment of the present invention.

Figure 3A:
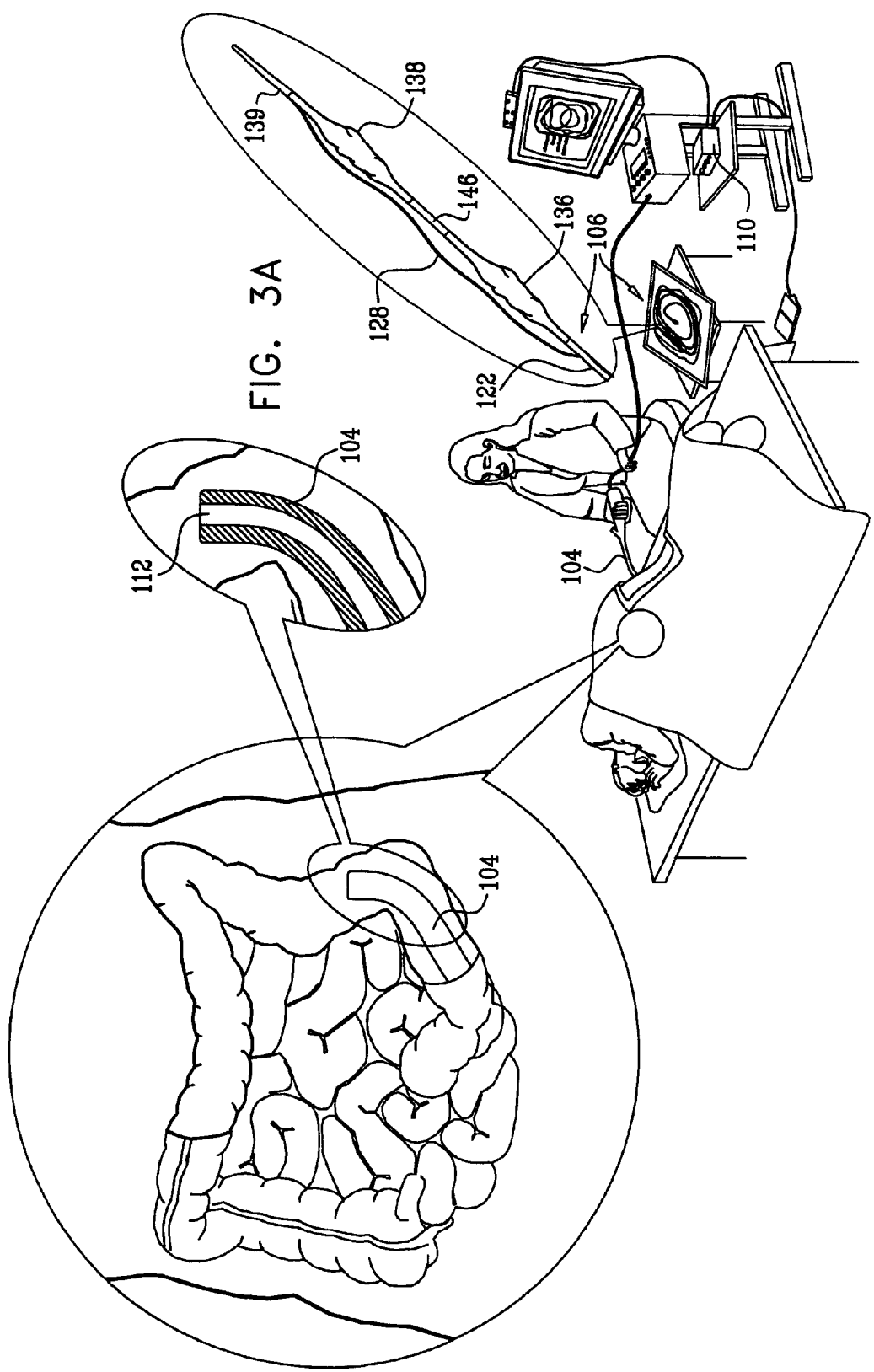

As seen in FIG. 3A, a conventional colonoscopy procedure is initiated, by insertion of a conventional endoscope 104 into operative engagement with a patient. The anchoring assembly 106 of the present invention may remain in a sealed package unless and until needed.

Figure 3B:
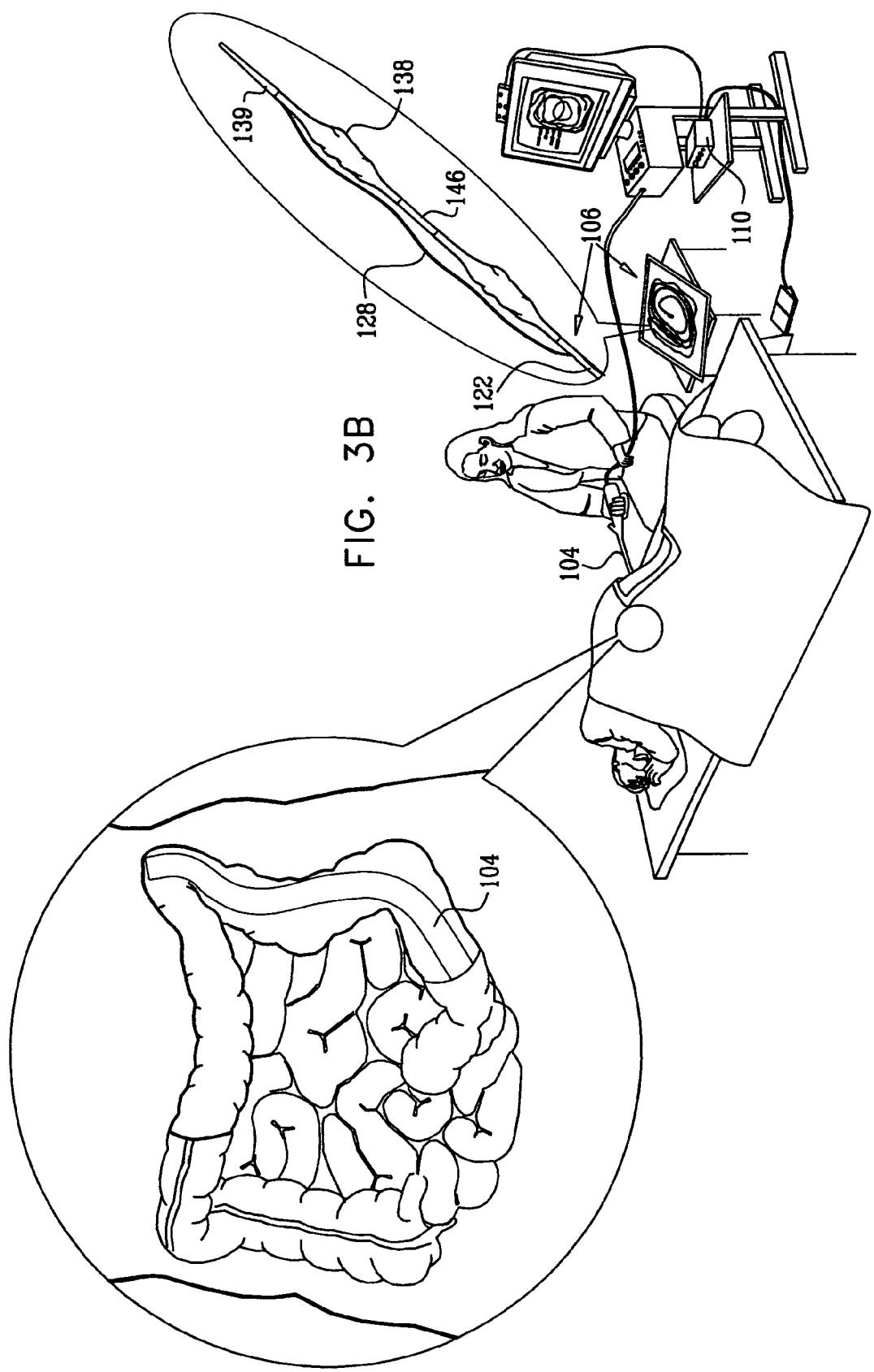

FIG. 3B illustrates a clinical difficulty in the course of the colonoscopy in which the operator is unable to successfully advance past a bend in the large intestine, typically at the splenic flexure.

Figure 3C:
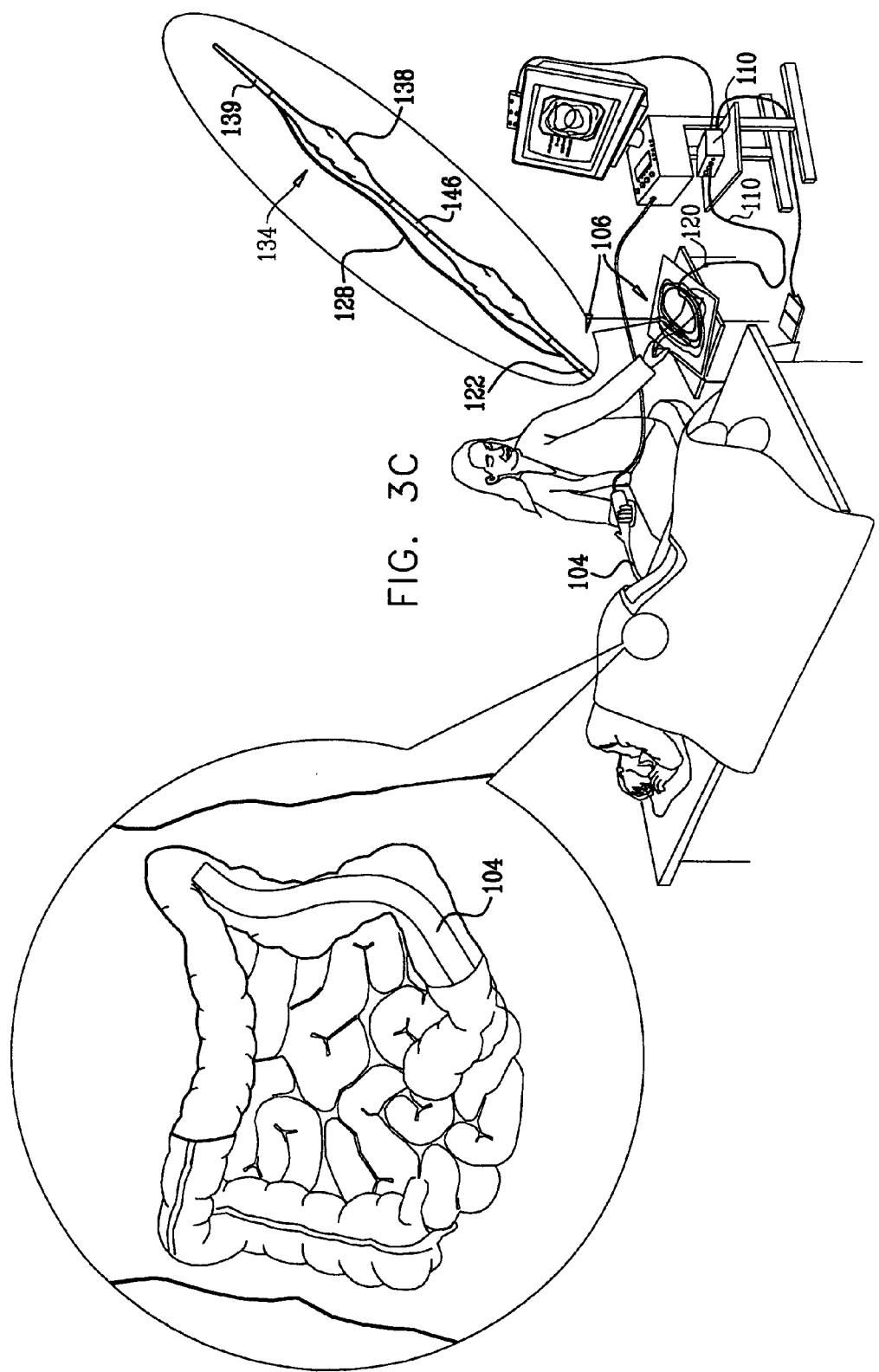

In accordance with the present invention, the operator, facing the clinical difficulty, unpacks the anchoring assembly 106 of the present invention and connects the connector 120 to the inflation/deflation control assembly 110, as shown in FIG. 3C. Preferably, the inflation/deflation control assembly 110 is operated to deflate the balloon assembly 134, forming part of the anchoring assembly 106.

Figure 3D:
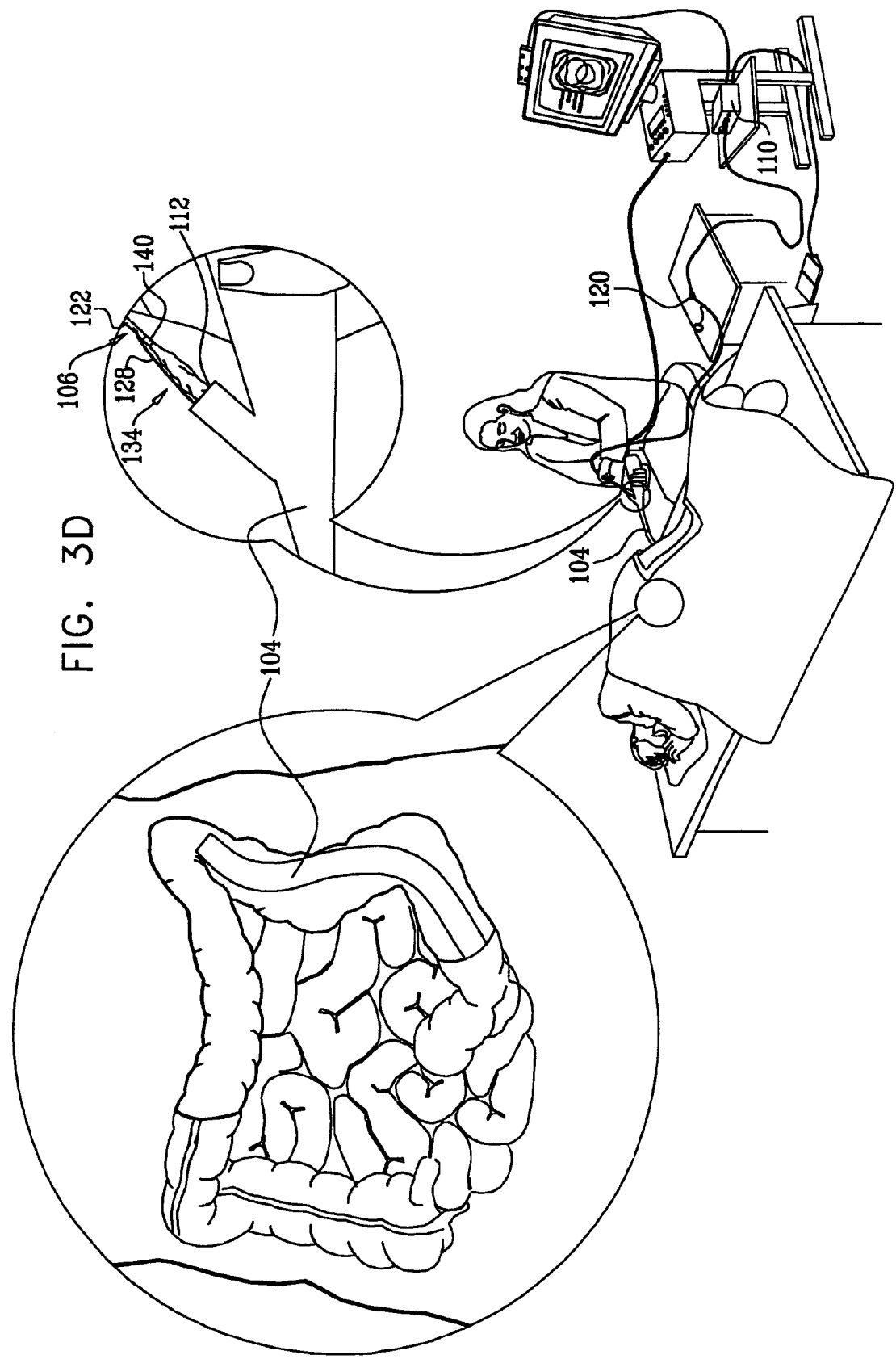

As seen in FIG. 3D, the operator then threads the anchoring assembly with the balloon assembly 134 in a deflated state, tip element 139 first, through the instrument channel 112 of endoscope 104. As noted above, it is a particular feature of the present invention that the anchoring assembly 106 is able to traverse the instrument channel 112.

FIG. 3E shows the anchoring assembly 106 partially emerged from the instrument channel 112 at the forward end of endoscope 104.

Figure 3F:
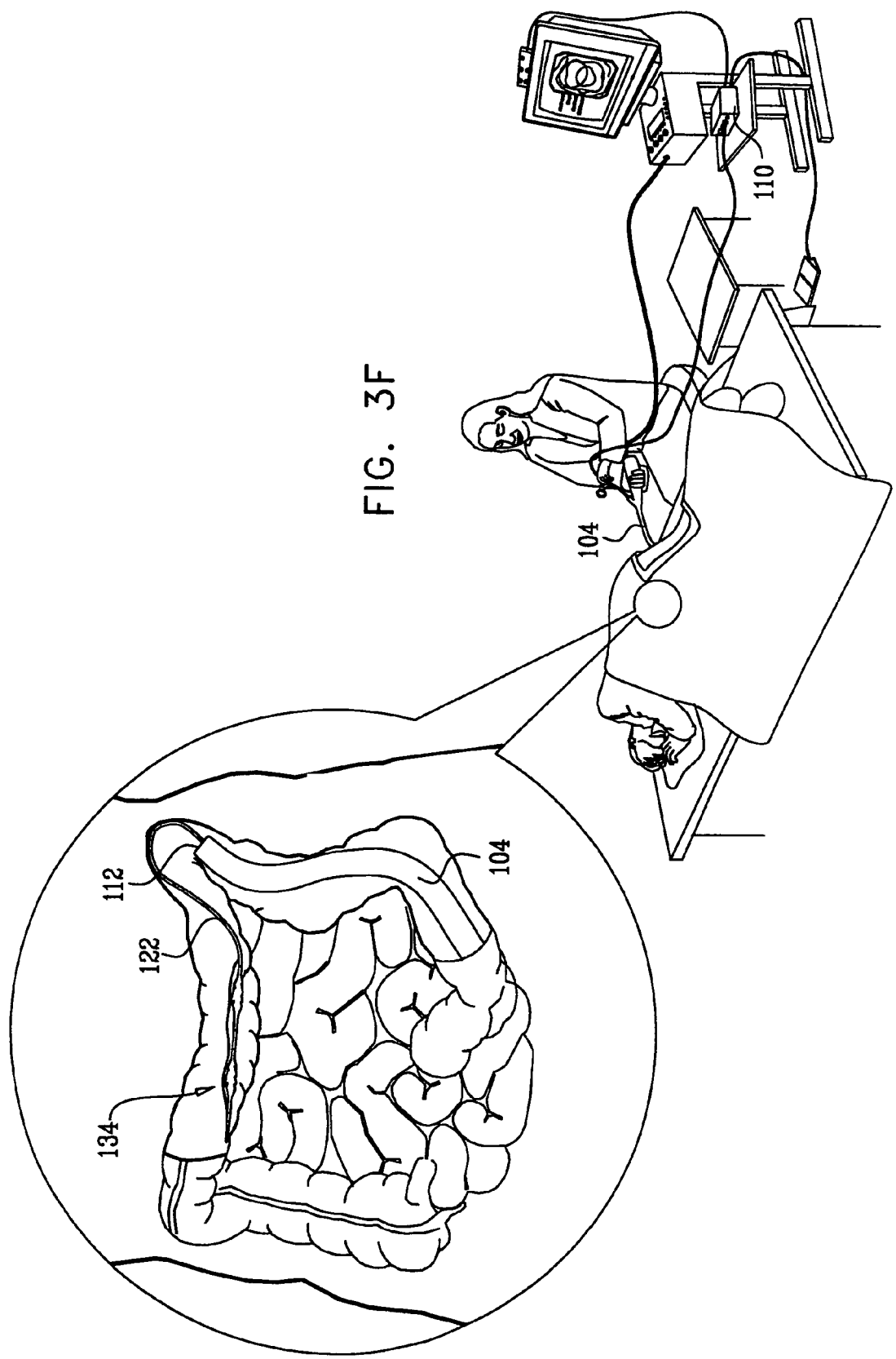

As seen in FIG. 3F, the operator advances the balloon assembly 134 until it is positioned forwardly of the bend in the intestine, preferably by pushing multi-lumen tube 122 forwardly through the instrument channel 112 of the endoscope 104.

Figure 3H:
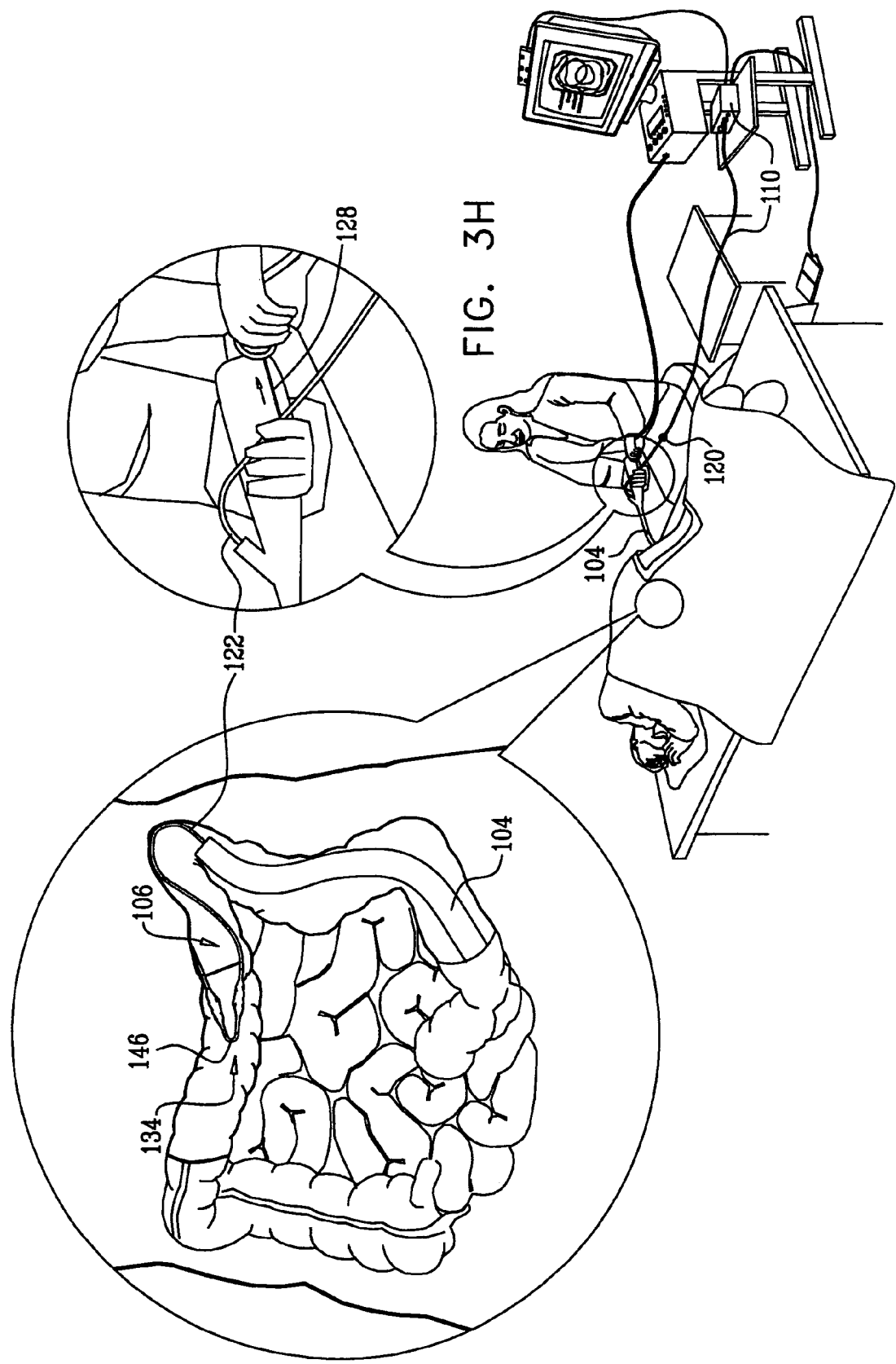
Figure 31:
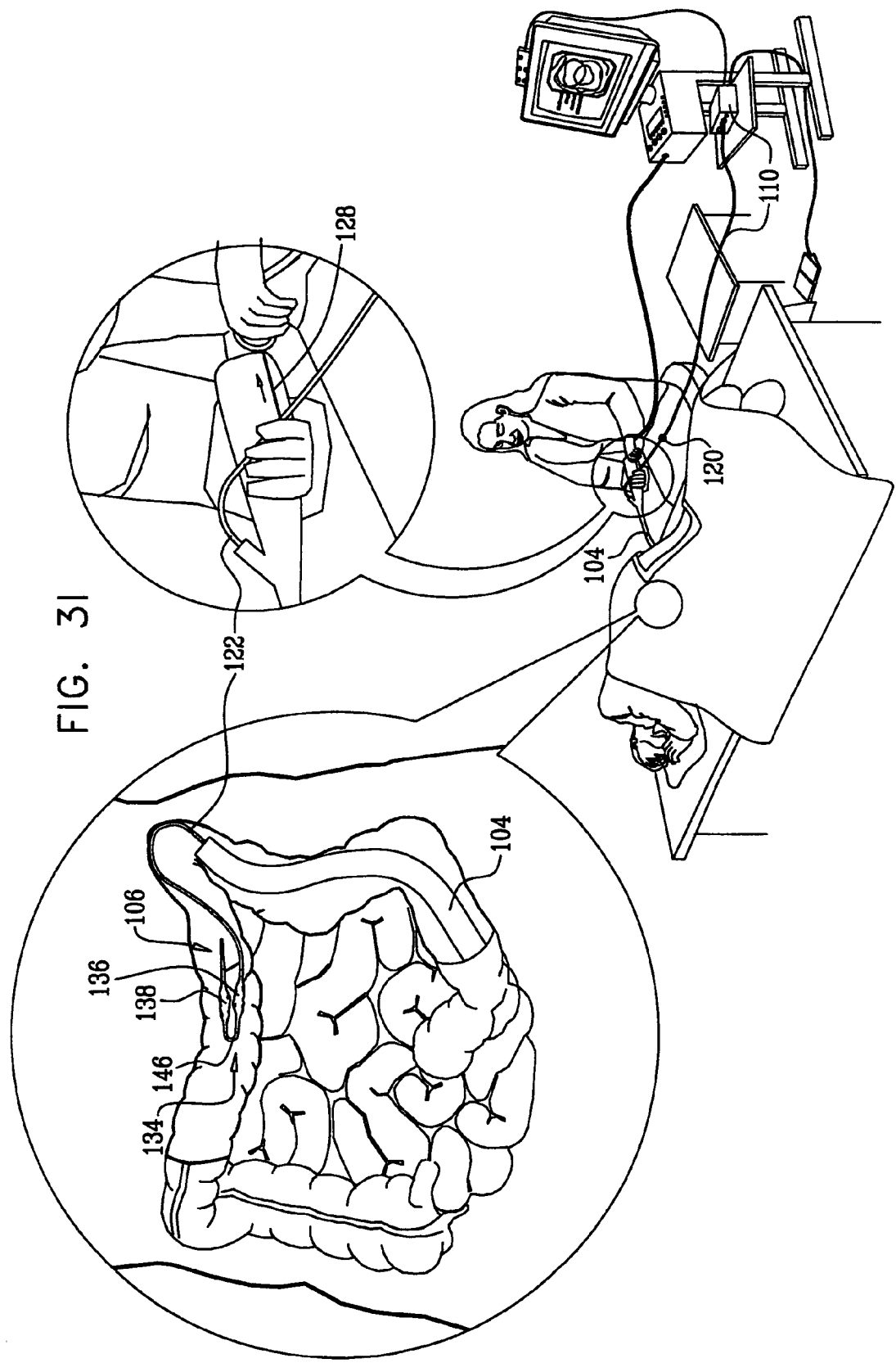

Thereafter, as seen in sequential illustrations FIGS. 3G, 3H and 3I, the operator pulls on the manipulation wire 128, thereby tensioning the manipulation wire and causing the balloon assembly 134 to fold over on itself, preferably bending intermediate tube 146, such that first and second balloons 136 and 138 lie generally alongside each other within the large intestine.

The operator preferably then inflates the first and second balloons 136 and 138 via lumens 124 and 148, using the inflation/deflation control assembly 110. The combined inflation of the first and second balloons 136 and 138 in generally side-by-side orientation in the large intestine, as seen in FIG. 3J, anchors the anchoring assembly 106 in the large intestine, such that the anchoring assembly can serve as a guide for the endoscope 104.

Following anchoring of the anchoring assembly 106 as seen in FIG. 3J, the operator pulls on the multi-lumen tube 122, thus tensioning the anchoring assembly 106, as seen in FIG. 3K.

The endoscope is then advanced over the multi-lumen tube 122 of anchoring assembly 106 past the bend in the large intestine, which had earlier presented a difficulty, to a location rearwardly adjacent the inflated balloon assembly 134, as seen in FIG. 3L.

Figure 3M:
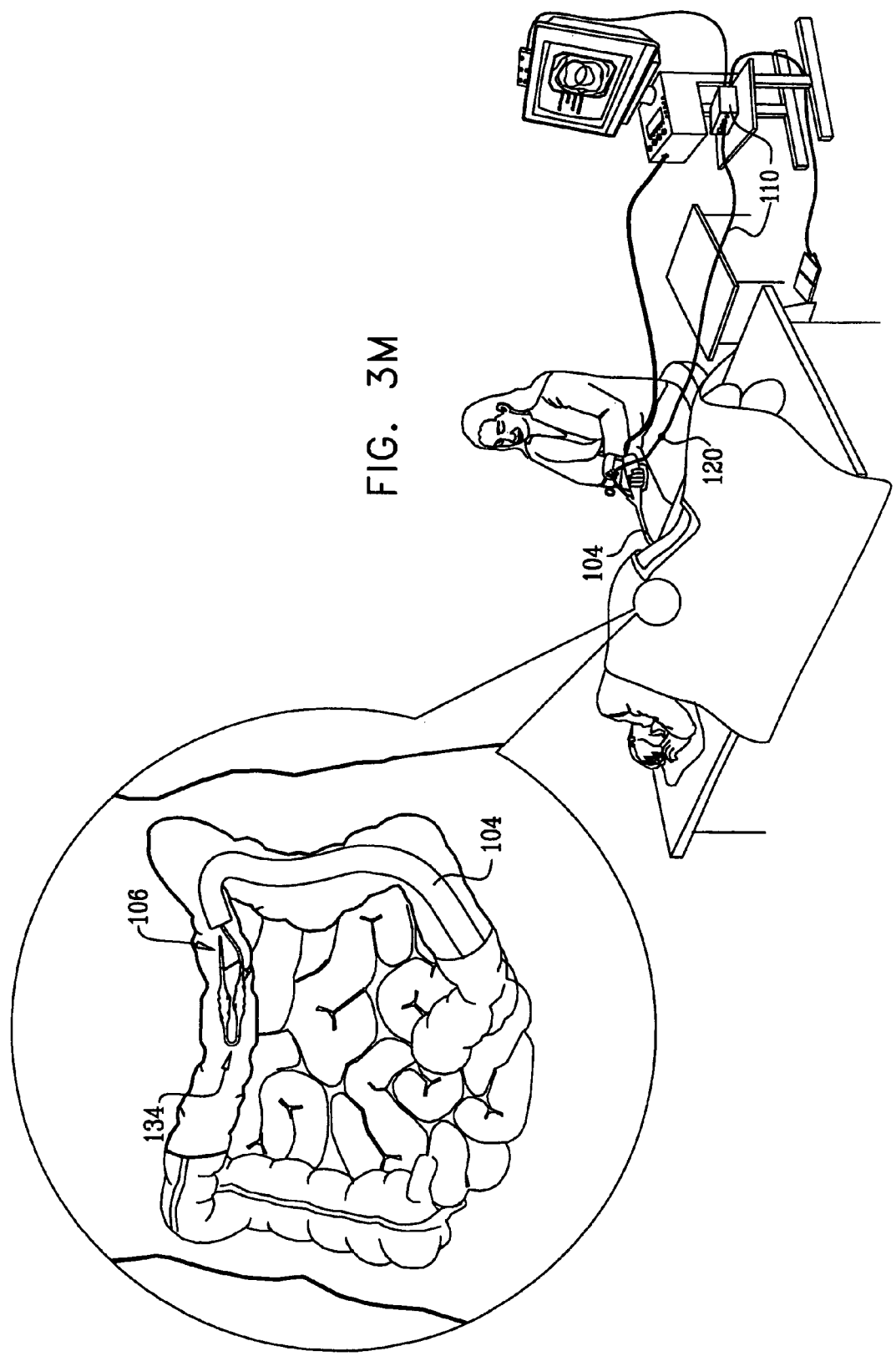

As seen in FIG. 3M, the balloon assembly 134 may then be deflated, via lumens 124 and 148, using the inflation/deflation control assembly 110.

Figure 3N:
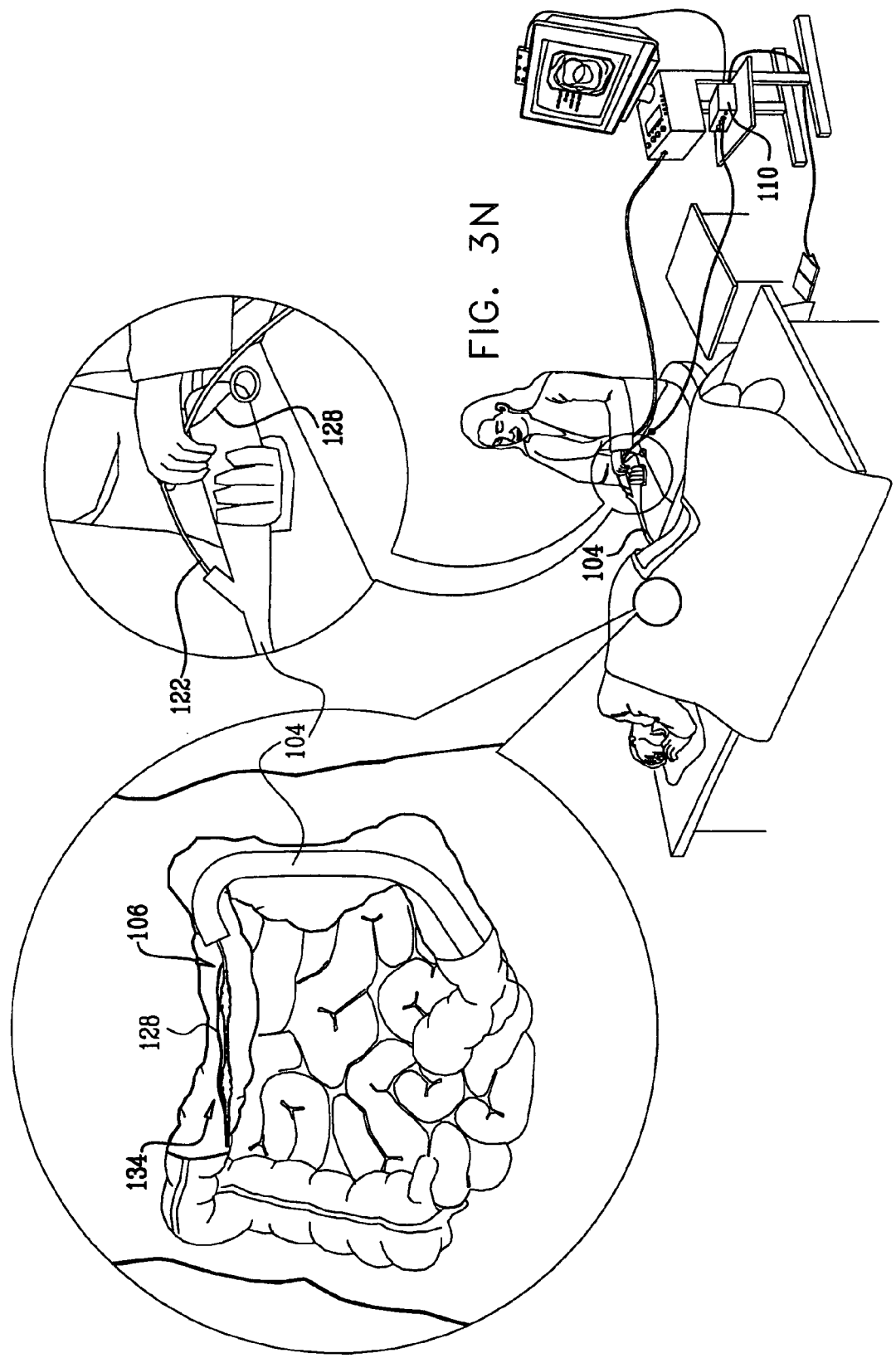

The balloon assembly 134 may then be restored to its non-bent-over orientation, as seen in FIG. 3N, preferably by the operator releasing and/or pushing the manipulation wire 128 forwardly.

Should it be desired to further advance the endoscope past additional bends which present difficulties, the procedure described hereinabove with respect to FIGS. 3F-3N may be repeated at such bends.

Once further use of the anchoring assembly is no longer needed in the colonoscopy procedure, the anchoring assembly 106 with the deflated balloon assembly 134 may be pulled back by the operator through the instrument channel 112 of the endoscope 104, as seen in FIG. 3O, and removed from the endoscope 104 and discarded. It is a particular feature of the present invention that the anchoring assembly is able to be drawn back through the instrument channel 112 following use.

Figure 4:
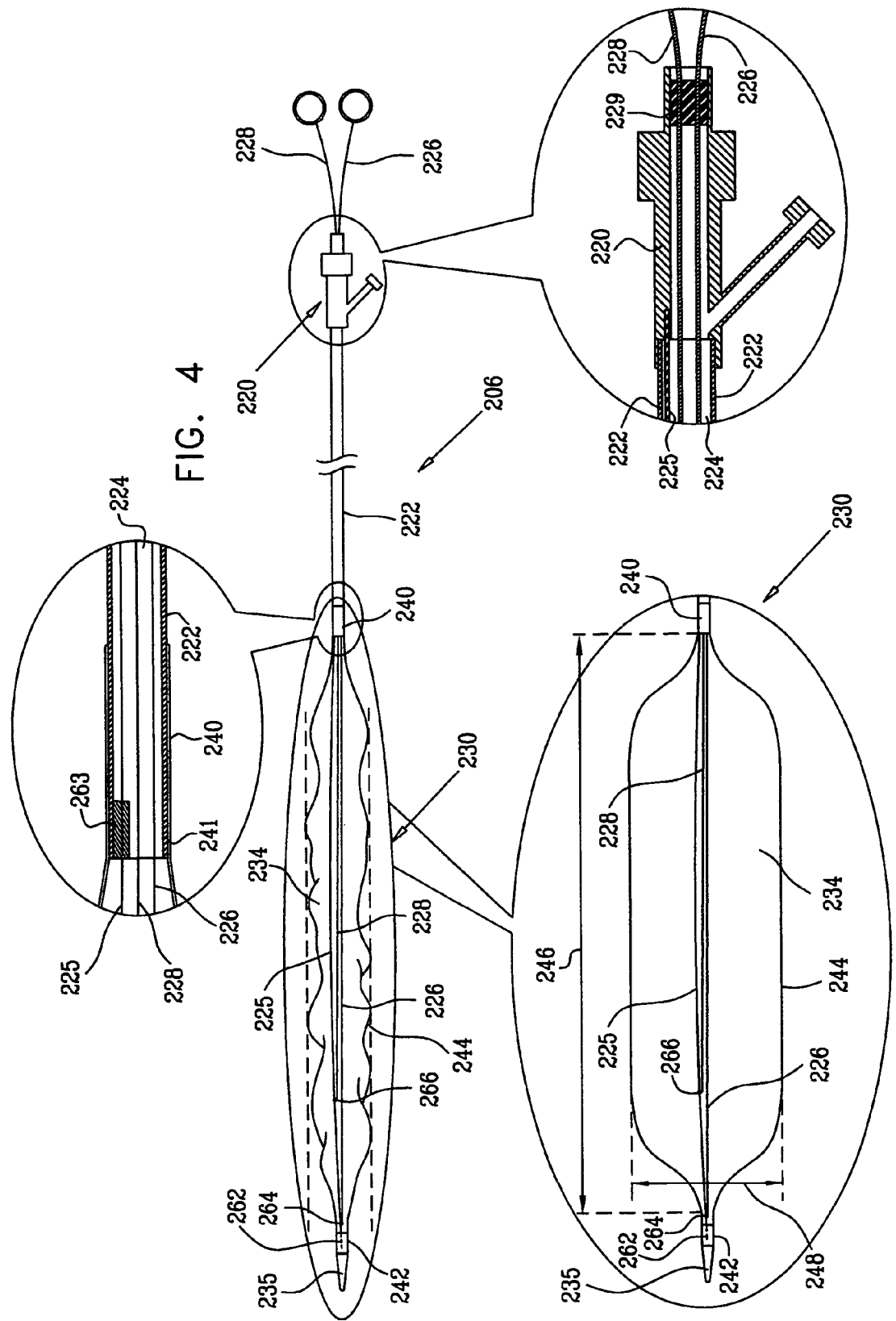
FIG. 4 is a simplified partially pictorial, partially sectional illustration of an anchoring assembly associatable with an endoscope in accordance with another preferred embodiment of the present invention.

Reference is now made to FIG. 4, which is a simplified partially pictorial, partially sectional illustration of an anchoring assembly 206 associatable with an endoscope in accordance with a preferred embodiment of the present invention.

As seen in FIG. 4, the anchoring assembly 206 preferably comprises a catheter including a connector 220 which is suitable for operative engagement with inflation/deflation control assembly 110 (FIG. 1). A single-lumen tube 222 is preferably fixedly mounted on connector 220 and includes a single lumen 224 for inflation/deflation, through which extends a flexible elongate element such as an elongate wire 225 and first and second manipulation wires 226 and 228. Elongate wire 225 is attached to connector 220 and thus is fixed with respect to single-lumen tube 222.

Connector 220 may be a conventional Y-connector, such as a Connector with 2 Female Luers and Male Slip, part number 80056, commercially available from QOSINA Medical Inc. of 150-Q Executive Drive, Edgewood, N.Y., USA, in which is formed a sealing plug 229, through which manipulation wires 226 and 228 slidably and sealingly extend. Sealing plug 229 may be realized by injecting silicon glue into the Y-connector as shown or may have any other suitable configuration.

Elongate wire 225 preferably is formed of a flexible metal, such as Nitinol or stainless steel. Manipulation wires 226 and 228 are each preferably formed of a highly flexible, non-stretchable material such as nylon. Alternatively, manipulation wires 226 and 228 may be formed of a suitable metal, such as Nitinol.

Single-lumen tube 222 preferably has an outer diameter of approximately 1.5-3.5 mm. Lumen 224 preferably has an inner diameter of approximately 1.0-3 mm. Elongate wire 225 preferably has a diameter of approximately 0.3-0.9 mm. Manipulation wires 226 and 228 preferably each have a diameter of approximately 0.1-0.3 mm.

Single-lumen tube 222 is suitable for passage through the instrument channel 112 of a conventional endoscope and typically has an overall length of between 2 and 3 meters.

An inflatable/deflatable balloon assembly 230 is provided, including a single balloon 234 and a tip element 235. Balloon 234 preferably comprises a sleeve formed of non-substantially-stretchable nylon or polyurethane having respective rearward and forward neck portions 240 and 242 and a central portion 244, which when inflated has an approximate length of 85-180 mm and diameter of 35-45 mm, denoted by respective reference numerals 246 and 248 in FIG. 4. Preferably, the length 246 of the balloon 234, between the rearward and forward neck portions 240 and 242, is at least twice the diameter 248 thereof.

Rearward neck portion 240 of balloon 234 is sealingly mounted as by adhesive or ultrasonic welding onto a forward end 241 of single-lumen tube 222. Forward neck portion 242 of balloon 234 is sealingly mounted as by adhesive or ultrasonic welding onto a rearward end of tip element 235. Tip element 235 is generally flexible forward facing conical element, preferably of length between 5 and 40 mm and having maximum outer diameter of approximately 1.0-3.5 mm.

A forward end 262 of elongate wire 225 is fixed to tip element 235, preferably at a rearward end thereof as by adhesive. The elongate wire 225 is also fixed to the forward end 241 of single-lumen tube 222, as by an adhesive or other attachment 263.

A forward end 264 of manipulation wire 226 is fixed to tip element 235 or, as shown, to elongate wire 225 just rearward of tip element 235, as by adhesive, laser welding or ultrasonic welding.

A forward end 266 of manipulation wire 228 is fixed to elongate wire 225 rearward of the junction of the forward end of manipulation wire 226, as by adhesive, laser welding or ultrasonic welding. Preferably the distance between the junction of manipulation wire 226 and that of manipulation wire 228 is equal to between approximately 15% and 20% of the length 246 of the balloon 234.

It is appreciated that any other suitable configuration of elongate manipulation elements may be used alternatively to manipulation wires 226 and 228.

Reference is now made to FIGS. 5A, 5B, 5C, 5D, 5E, 5F, 5G, 5H, 5I, 5J, 5K, 5L, 5M, 5N and 5O, which are simplified pictorial illustrations of operation of the endoscope system of FIG. 1 and the anchoring assembly of FIG. 4 in accordance with a preferred embodiment of the present invention.

Figure 5A:
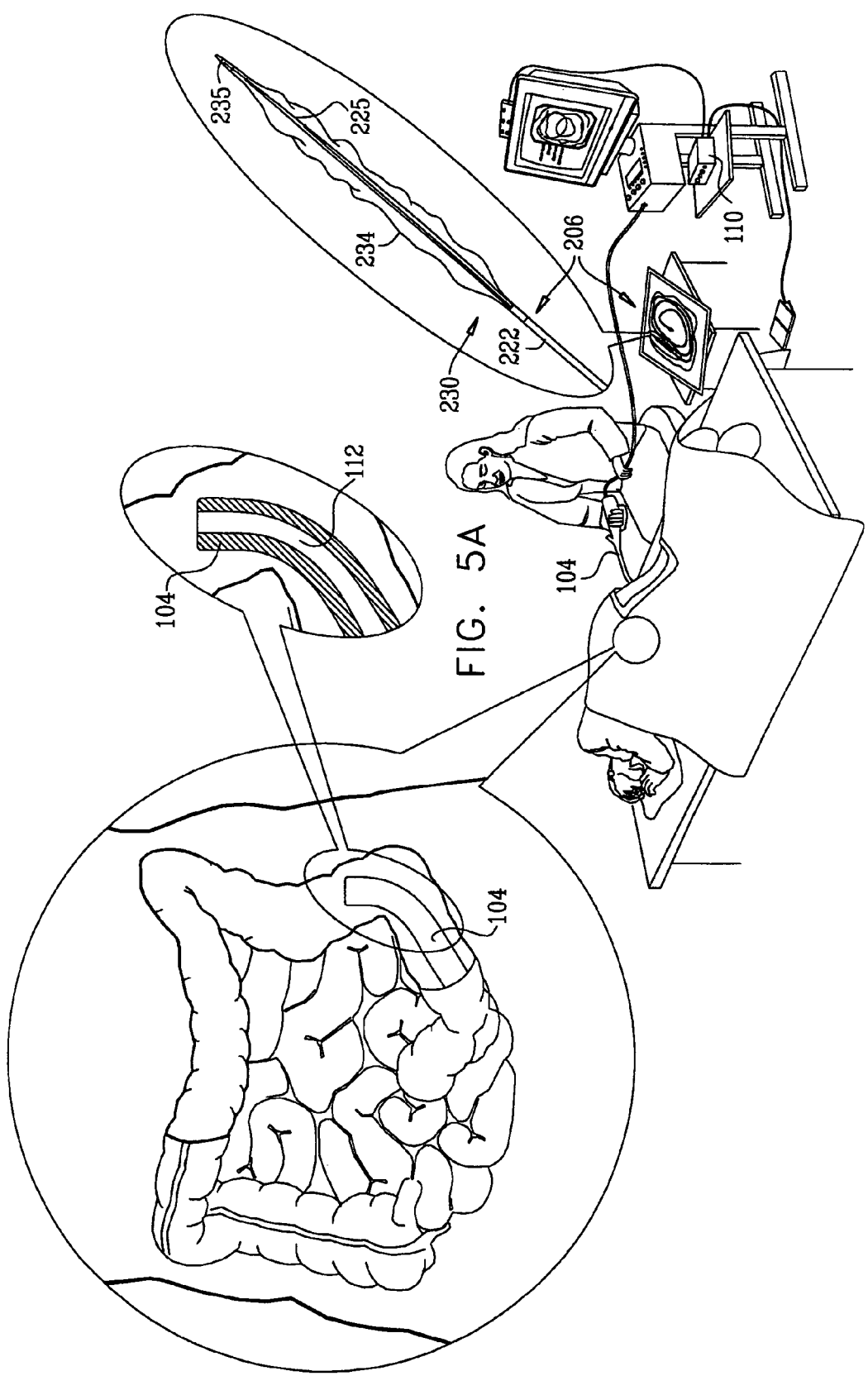

As seen in FIG. 5A, a conventional colonoscopy procedure is initiated, by insertion of a conventional endoscope 104 (FIG. 1) into operative engagement with a patient. The anchoring assembly 206 of the present invention may remain in a sealed package unless and until needed.

Figure 5B:
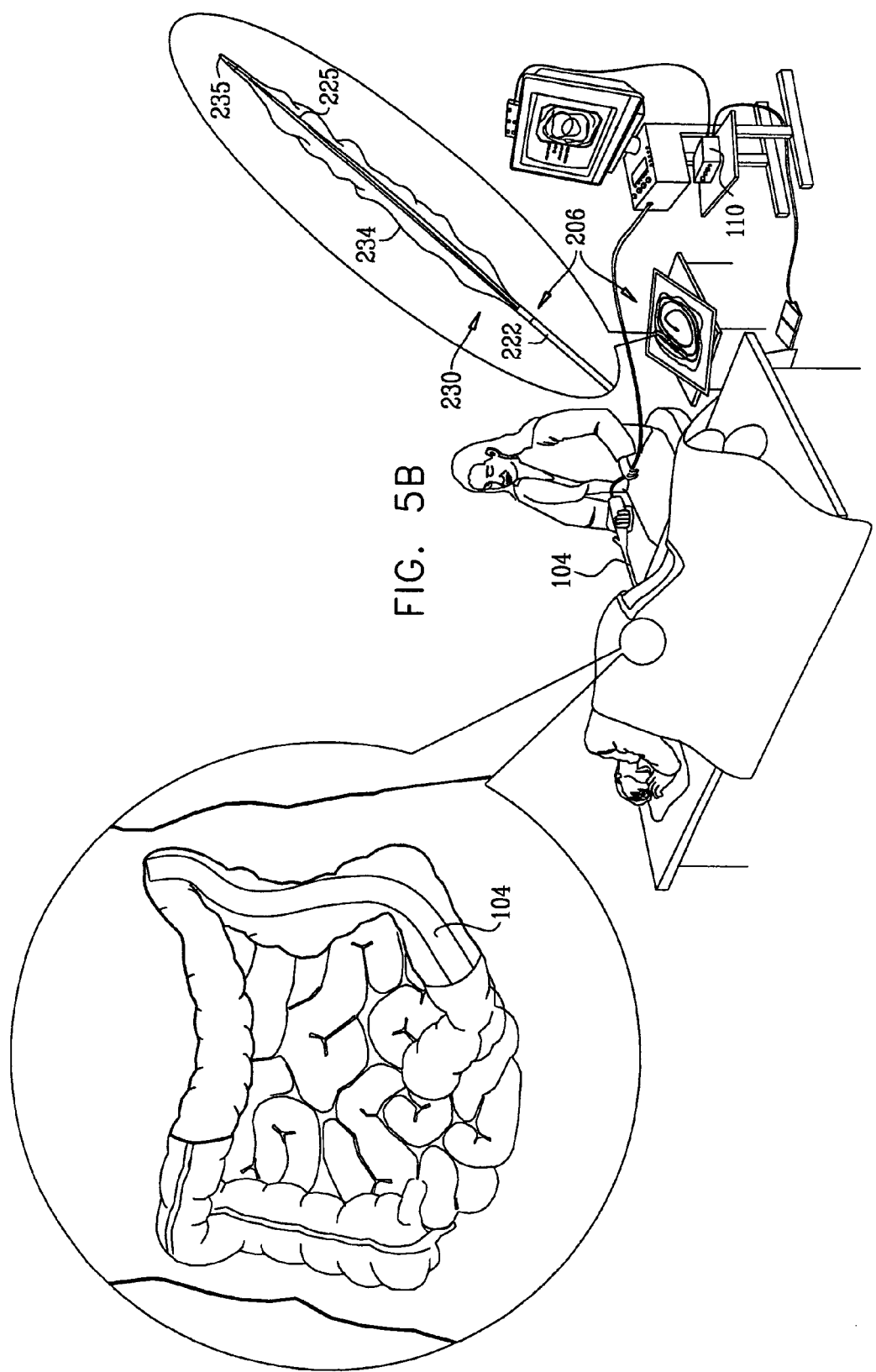

FIG. 5B illustrates a clinical difficulty in the course of the colonoscopy in which the operator is unable to successfully advance past a bend in the large intestine, typically at the splenic flexure.

Figure 5C:
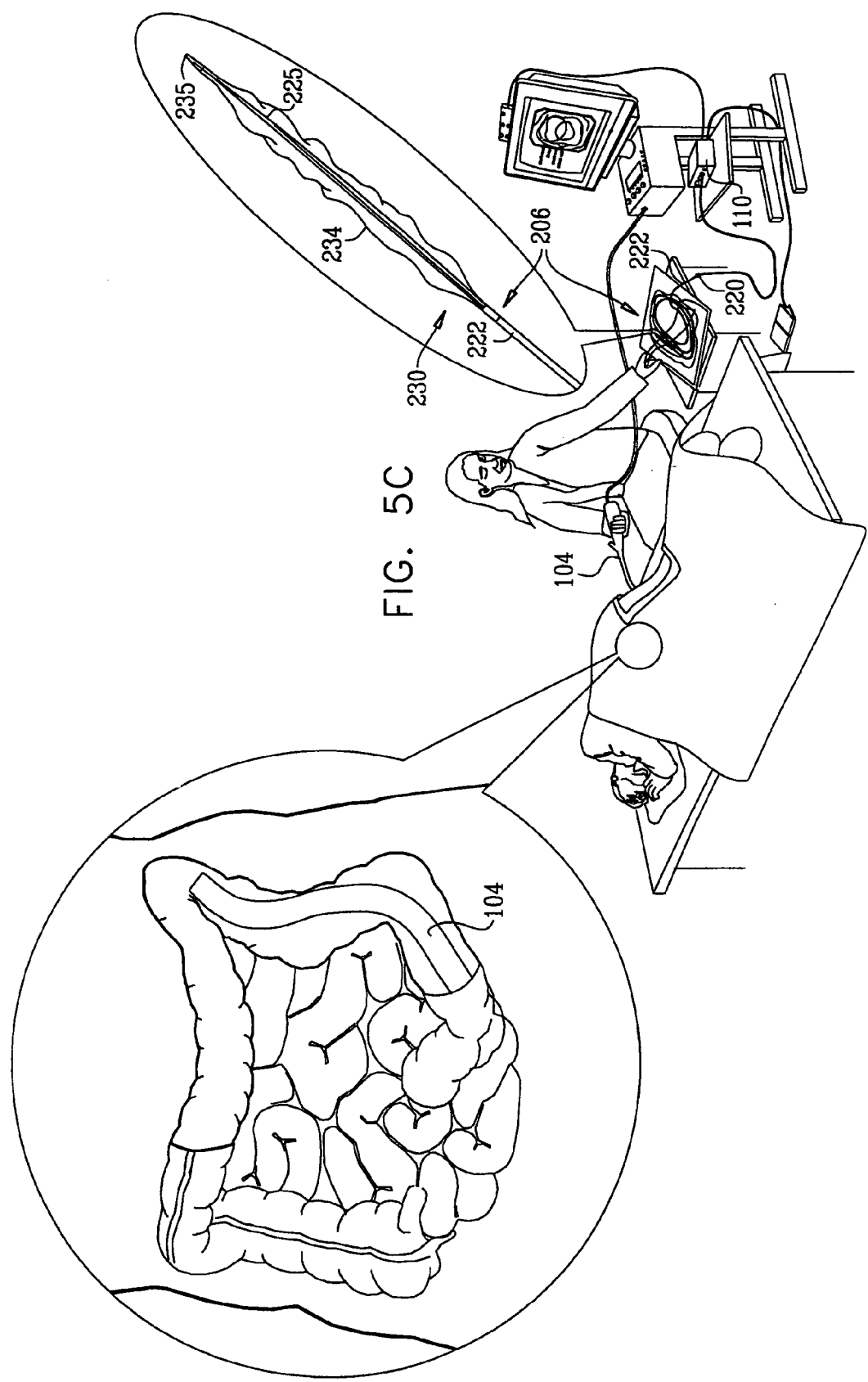

In accordance with the present invention, the operator, facing the clinical difficulty, unpacks the anchoring assembly 206 of the present invention and connects the connector 220 to the inflation/deflation control assembly 110, as shown in FIG. 5C. Preferably, the inflation/deflation control assembly 110 is operated to deflate the balloon assembly 230.

Figure 5D:
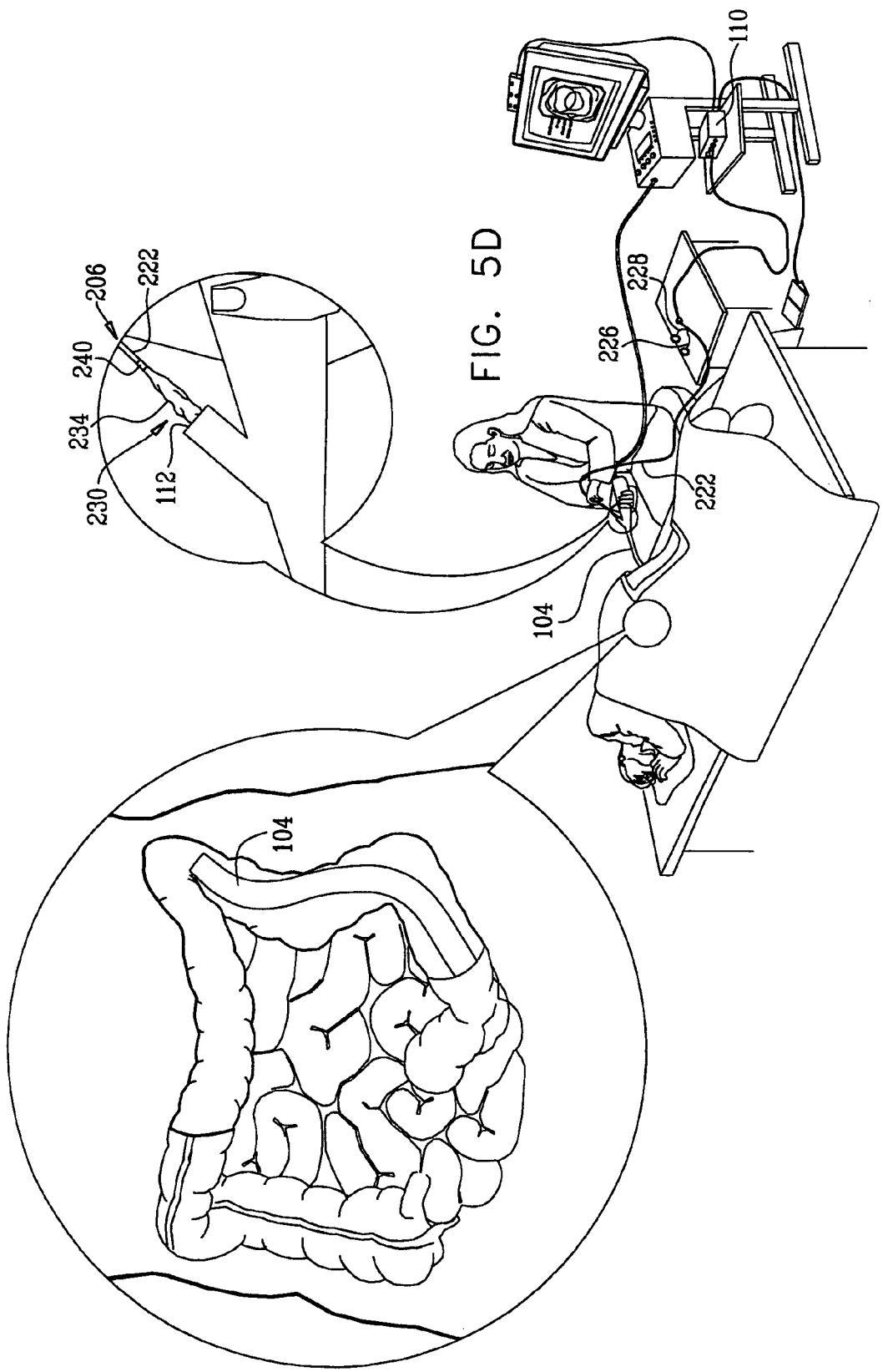

As seen in FIG. 5D, the operator then threads the anchoring assembly with the balloon assembly 230 in a deflated state, tip element 235 first, through the instrument channel 112 of endoscope 104. As noted above, it is a particular feature of the present invention that the anchoring assembly is able to traverse the instrument channel 112.

FIG. 5E shows the anchoring assembly 206 partially emerged from the instrument channel 112 at the forward end of endoscope 104.

Figure 5F:
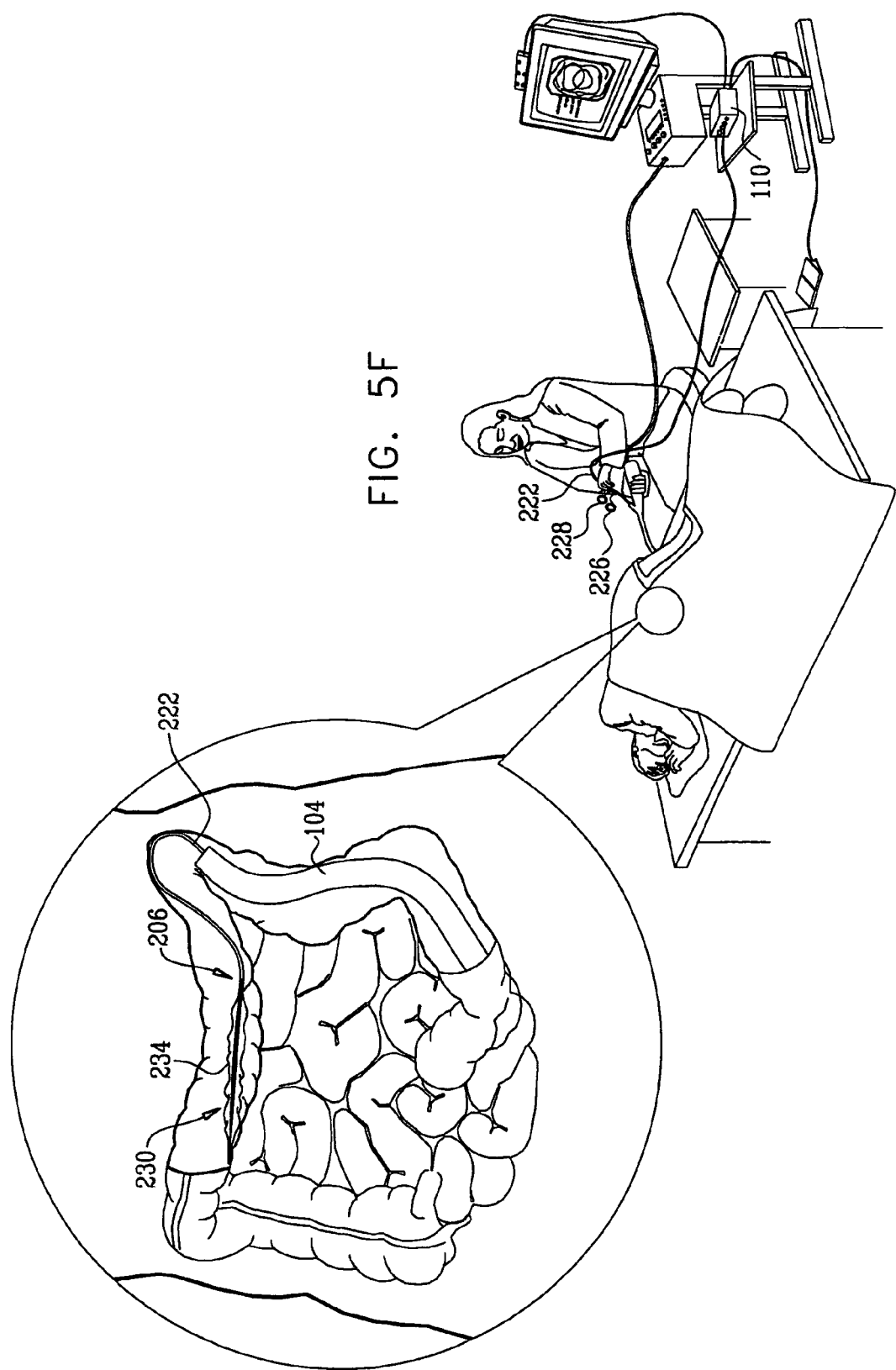

As seen in FIG. 5F, the operator advances the balloon assembly 230 until it is positioned in a first, deflated orientation, forwardly of the bend in the intestine, preferably by pushing single-lumen tube 222 forwardly through the instrument channel 112 of the endoscope 104.

Figure 5G:
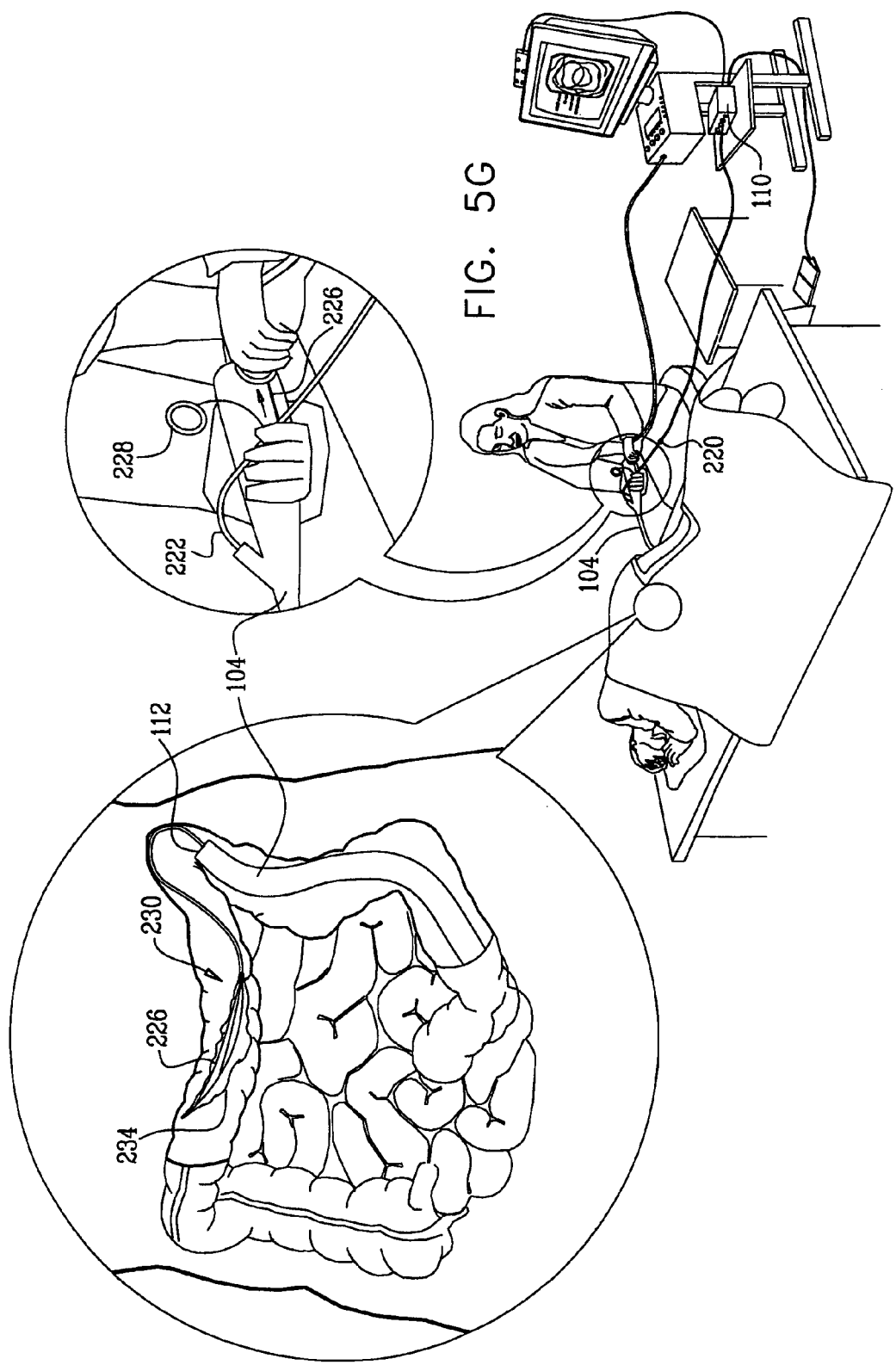
Figure 5H:
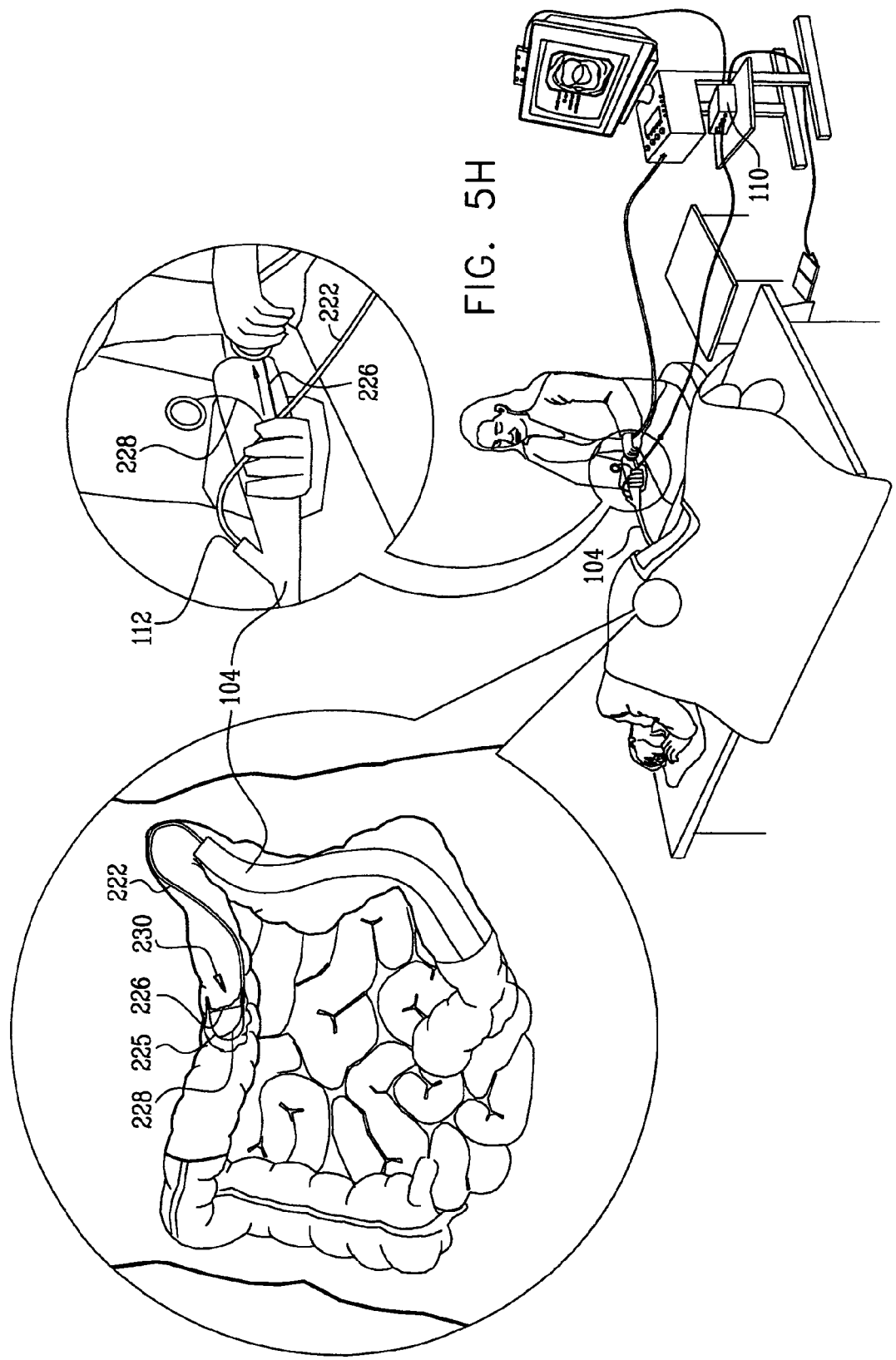

Thereafter, as seen in sequential illustrations FIGS. 5G and 5H, the operator pulls on the manipulation wire 226, thereby tensioning the manipulation wire 226, causing the balloon assembly 230 to fold over on itself within the large intestine.

Figure 5I:
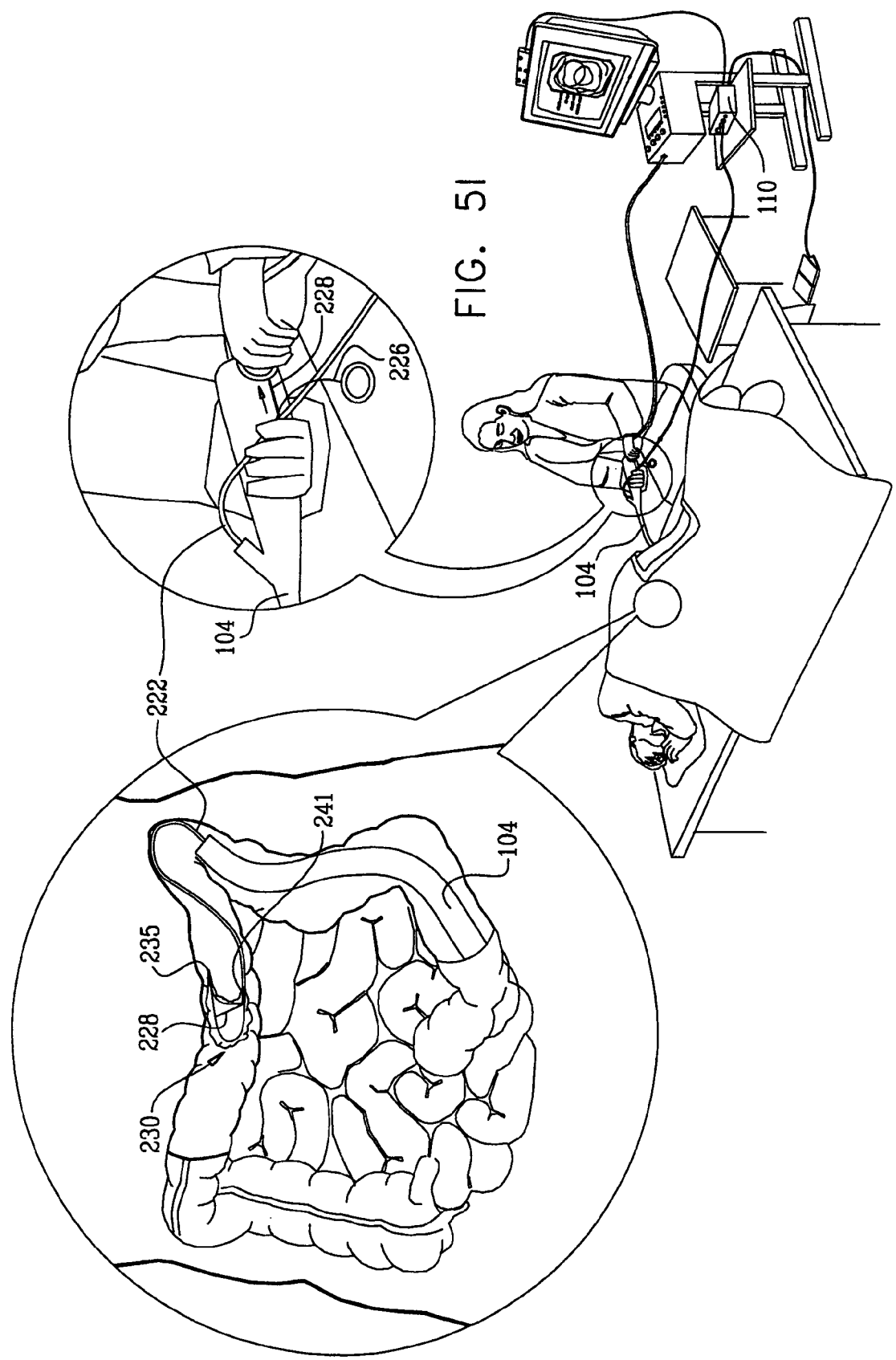

Thereafter, the operator pulls on the manipulation wire 228, thereby tensioning the manipulation wire 228, thereby causing the tip element 235 of balloon assembly 230 to be positioned rearwardly of the forward end 241 of single-lumen tube 222, as seen in FIG. 5I.

By performing the sequential steps of pulling manipulation wires 226 and 228, as illustrated in FIGS. 5G-5I, the balloon assembly 230 is being positioned in a second, folded-over orientation in the large intestine. It is appreciated that any other suitable configuration of plurality of elongate manipulation elements may be used alternatively to manipulation wires 226 and 228, for sequential orientation of the inflatable/deflatable balloon assembly 320 in the above described second orientation.

The operator preferably then inflates the balloon 234 via lumen 224, using the inflation/deflation control assembly 110. The inflation of the balloon 234 which is bent over itself in the large intestine, as seen in FIG. 5J, anchors the anchoring assembly 206 in the large intestine, such that the anchoring assembly can serve as a guide for the endoscope 104.

Figure 5J:
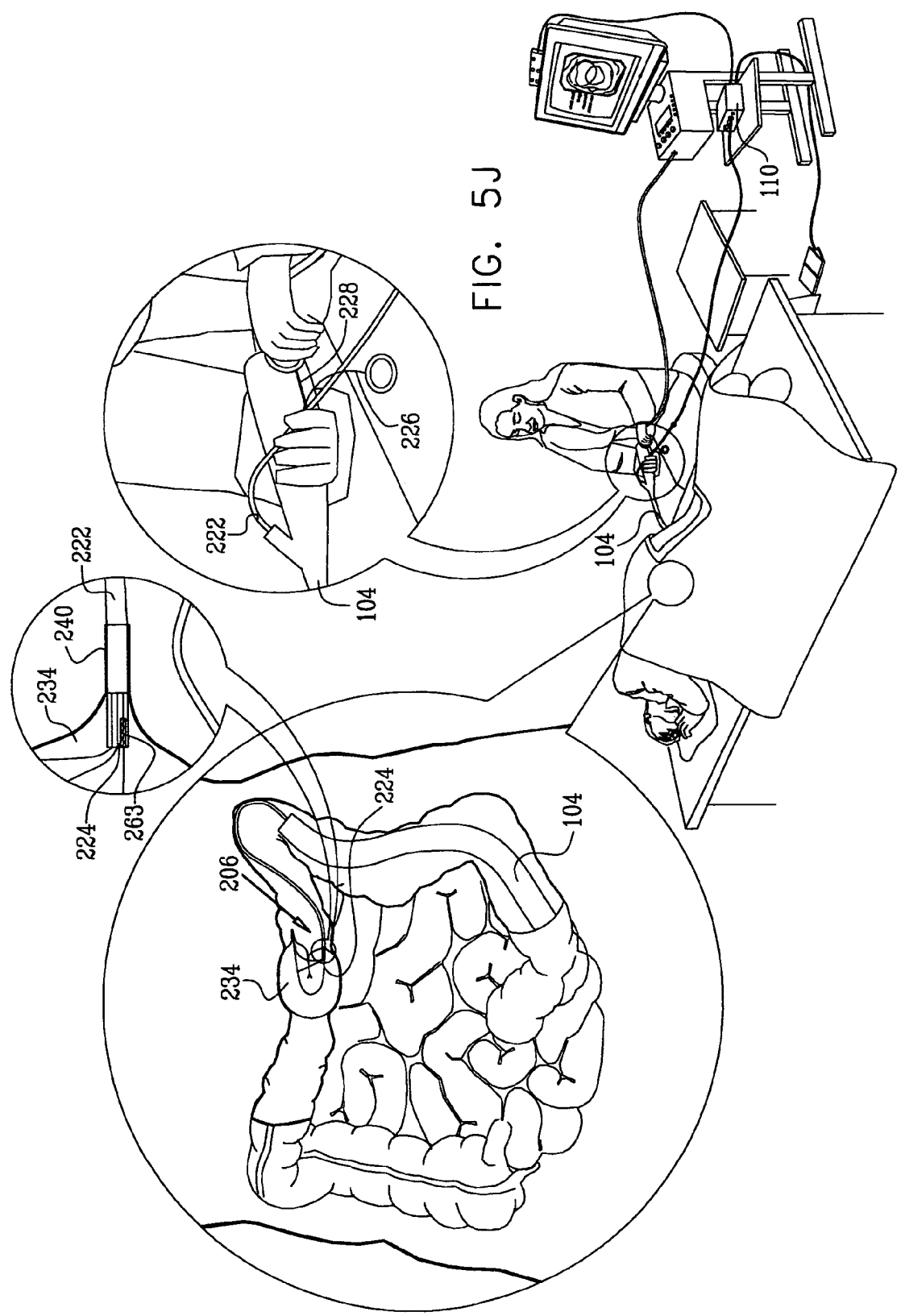

Following anchoring of the anchoring assembly 206 as seen in FIG. 5J, the operator pulls on the single-lumen tube 222, thus tensioning the anchoring assembly 206, as seen in FIG. 5K.

The endoscope 104 is then advanced over the single-lumen tube 222 of anchoring assembly 206 past the bend in the large intestine, which had earlier presented a difficulty, to a location rearwardly adjacent the inflated balloon assembly 230, as seen in FIG. 5L.

As seen in FIG. 5M, the balloon assembly 230 may then be deflated, via lumen 224, using the inflation/deflation control assembly 110.

Figure 5N:
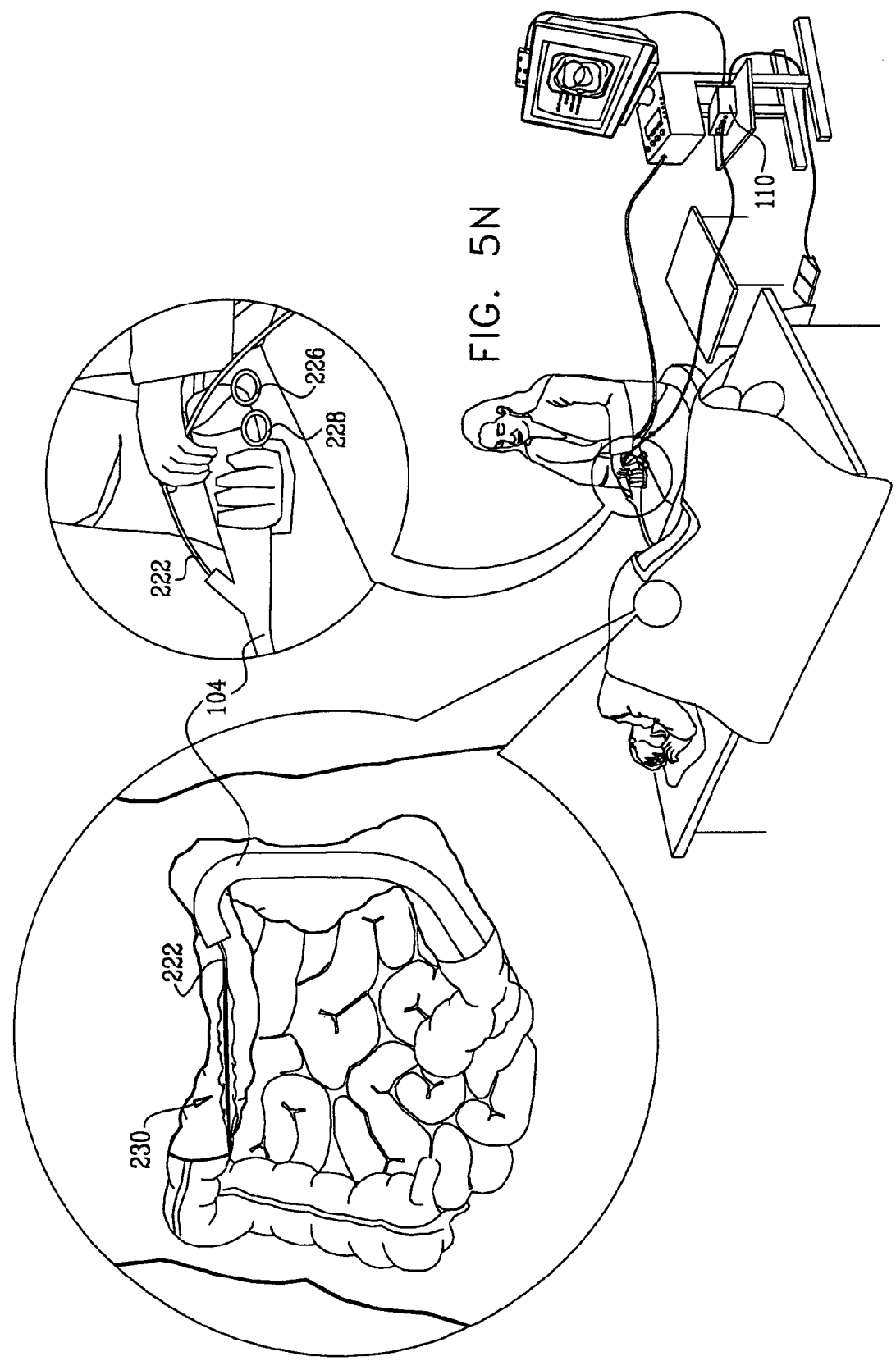
Figure 50:
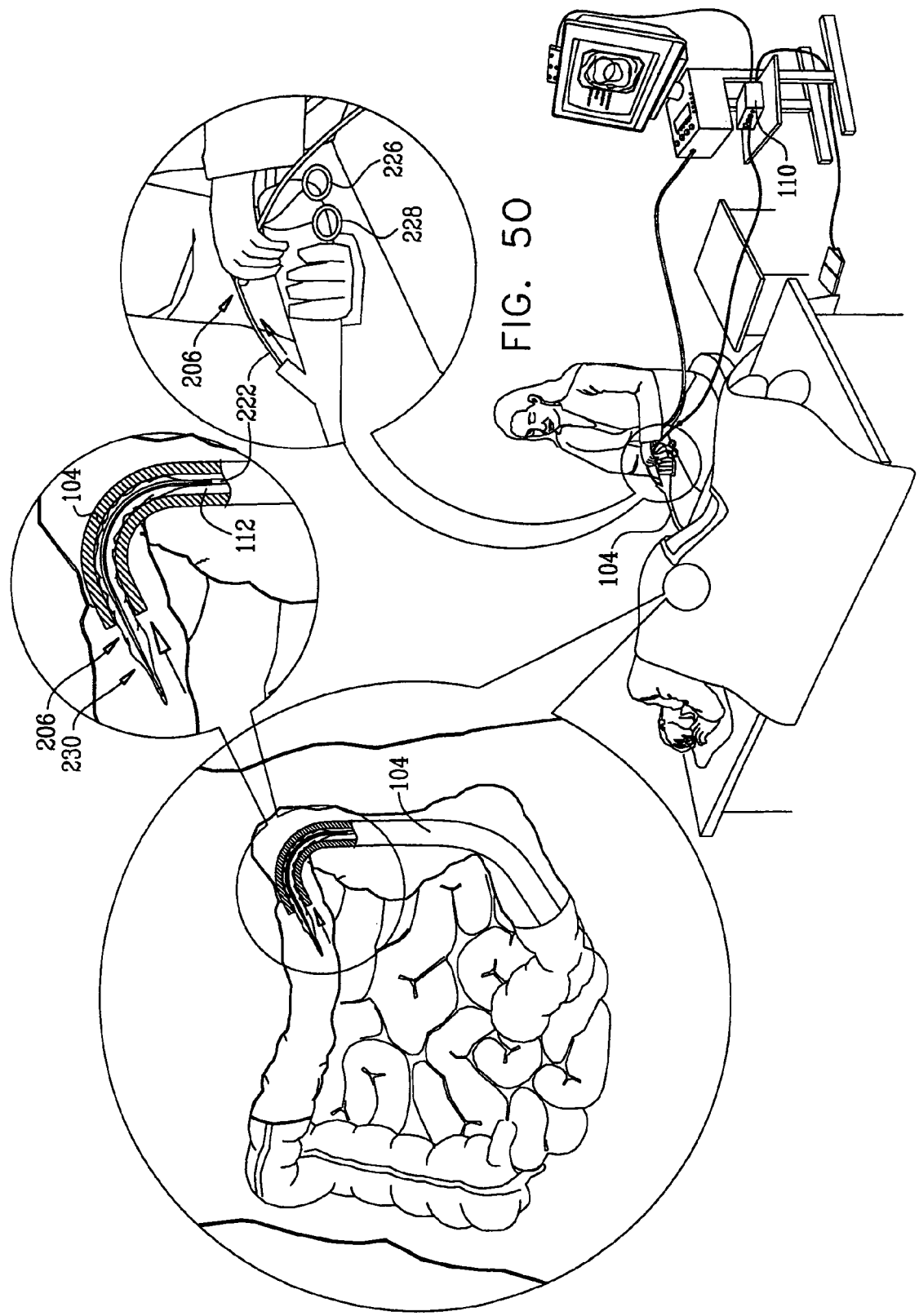

The balloon assembly 230 may then be restored to its non-bent-over orientation, as seen in FIG. 5N, preferably by the operator releasing and/or pushing the manipulation wires 226 and 228 forwardly.

Should it be desired to further advance the endoscope past additional bends which present difficulties, the procedure described hereinabove with respect to FIGS. 5F-5N may be repeated at such bends.

Once further use of the anchoring assembly is no longer needed in the colonoscopy procedure, the anchoring assembly 206 with the deflated balloon assembly 230 may be pulled back by the operator through the instrument channel 112 of the endoscope 104, as seen in FIG. 5O, and removed from the endoscope 104 and discarded. It is a particular feature of the present invention that the anchoring assembly is able to be drawn back through the instrument channel 112 following use.

Reference is now made to FIG. 6, which is a simplified partially pictorial, partially sectional illustration of an anchoring assembly 306 associatable with an endoscope in accordance with a preferred embodiment of the present invention.

As seen in FIG. 6, the anchoring assembly 306 preferably comprises a connector 320 which is suitable for operative engagement with inflation/deflation control assembly 110 (FIG. 1). A single-lumen tube 322 is preferably fixedly mounted at a rearward end thereof on connector 320 and includes a lumen 324 for inflation/deflation.

Tube 322 is preferably fixedly mounted at a forward end thereof to an elongate housing 326, extending along a longitudinal axis 328. The forward end of tube 322 is tightly received in a bore 329, extending along axis 328 which terminates forwardly in a bore 330, slightly narrower than bore 329 and communicating with lumen 324.

Bore 330 extends forwardly along axis 328 to a bore 332, which also extends along axis 328 forwardly of bore 330 and which has a larger diameter than bore 330. Bore 332 extends forwardly along axis 328 to a bore 334, which also extends along axis 328 forwardly of bore 332 and which has a larger diameter than bore 332. Housing 326 is formed with an elongate slot 336 extending along a rearward portion of bore 334 and communicating therewith.

Forwardly of elongate slot 336 and spaced therefrom along axis 328 by a cylindrical wall portion 338 are a pair of oppositely facing finger access windows 340 and 344, both of which communicate with a forward portion of bore 334. Bore 334 extends forwardly along axis 328 to a bore 354, which also extends along axis 328 forwardly of bore 334 and has a smaller diameter than bore 334.

Bore 354 terminates forwardly in a bore 356, narrower than bore 354, which extends forwardly along axis 328 and in turn terminates forwardly in a bore 358, which is slightly wider than bore 356.

A rearward end 360 of a single-lumen tube 362 is fixedly mounted in bore 358. Single lumen tube 362 is typically 2-3 meters in length and has a lumen 364 which communicates with the interior of bore 356.

An inflatable/deflatable balloon assembly 370 includes a balloon 372 and a tip element 374. Balloon 372 preferably comprises a sleeve formed of non-substantially-stretchable nylon or polyurethane having respective rearward and forward neck portions 376 and 378 and a central portion 379 which is selectably furled responsively to relative rotation of neck portions 376 and 378 about axis 328. When balloon 372 is unfurled and inflated, it has an approximate length of 60-110 mm and diameter of 55-70 mm. When balloon 372 is fully and tightly furled, it preferably has a maximum diameter of 2.5-4 mm.

Rearward neck portion 376 of balloon 372 is sealingly mounted as by adhesive or ultrasonic welding onto a forward end of single-lumen tube 362. Forward neck portion 378 of balloon 372 is sealingly mounted as by adhesive or ultrasonic welding onto a rearward end of tip element 374.

Selectable and readily monitorable furling of balloon 372 is preferably provided by a finger-actuated furling assembly 380. Furling assembly 380 preferably includes an elongate finger rotatable element 382 which is arranged for rotation about axis 328.

Elongate finger rotatable element 382 preferably includes a finger-engagable cylindrical portion 384, preferably having a knurled surface 386. Cylindrical portion 384 is located within a forward portion of bore 334 and preferably is integrally formed with a forward cylindrical portion 388, which is located within bore 354 and is sealingly and rotatably mounted for rotation therewithin by means of a ring seal 390.

Integrally formed with cylindrical portion 384 and extending rearwardly thereof is a cylindrical portion 392, which is located partially in a rearward portion of bore 334 and partially in bore 332. That part of cylindrical portion 392 which resides in the rearward portion of bore 334 is preferably formed with a cylindrical surface 393 which defines a worm gear. Cylindrical portion 392 is sealingly and rotatably mounted for rotation within bore 332 by means of a ring seal 394.

An axial bore 395 extends entirely through all of elongate finger rotatable element 382 along axis 328 and communicates with lumens 324 and 364.

An elongate wire 396 extends forwardly through axial bore 395, lumen 364 and balloon 372. A rearward end of elongate wire 396 is fixed to elongate finger rotatable element 382 at a rearward end of bore 395 by adhesive or a mechanical attachment 397 and a forward end of elongate wire 396 is fixed to tip element 374, at a rearward recess 398 thereof.

Elongate wire 396 preferably is formed of a flexible and torquable metal, such as Nitinol or stainless steel. It is appreciated that rotation of elongate finger rotatable element 382 produces corresponding rotation of tip element 374 and thus of the forward end of balloon 372 about axis 328, thereby to provide desired furling or unfurling of the balloon 372.

Single-lumen tube 362 preferably has an outer diameter of approximately 2.0-3.5 mm. Lumen 364 preferably has an inner diameter of approximately 1.0-2.5 mm. Elongate wire 396 preferably has an outer diameter of approximately 0.5-1.5 mm.

Monitoring of the extent of furling of the balloon 372 and of the concommittant stiffness of the balloon assembly 370 is preferably provided by a visually sensible indicator 399 which is mounted on a worm-gear surfacing riding nut 400 and which moves rearwardly or forwardly along slot 336 correspondingly with rotation of elongate finger rotatable element 382 and with furling/unfurling of balloon 372.

Figure 7A:
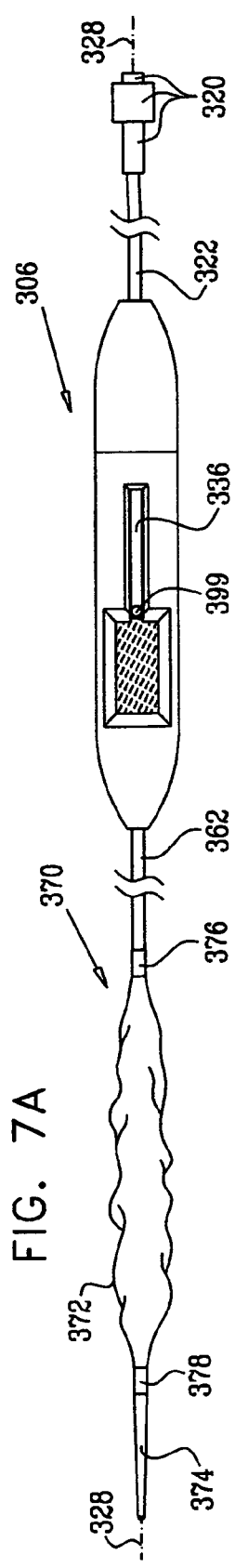
FIGS. 7A, 7B and 7C are simplified pictorial illustrations of the selectable furling and stiffening operation of an anchoring assembly associatable with an endoscope in accordance with the embodiment of FIG. 6.
Figure 7B:
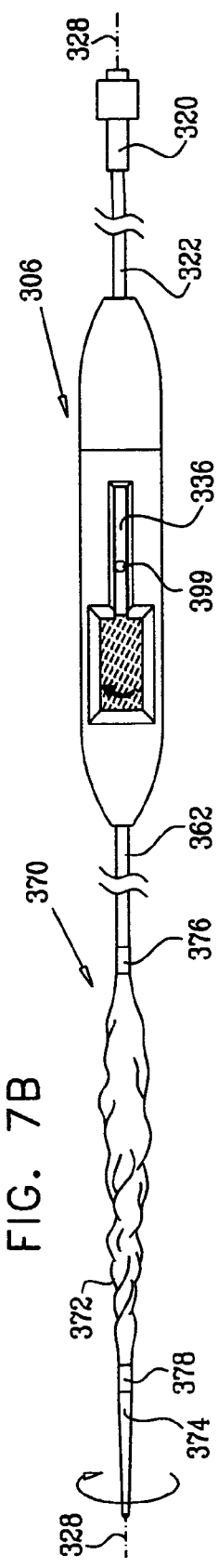
Figure 7C:
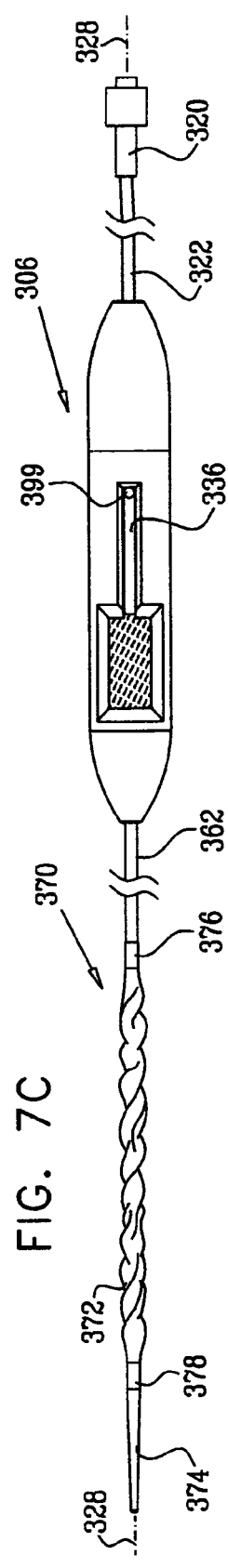

Reference is now made to FIGS. 7A, 7B and 7C, which are simplified pictorial illustrations of the selectable furling and stiffening operation of an anchoring assembly associatable with an endoscope in accordance with the embodiment of FIG. 6.

FIG. 7A illustrates balloon 372 in a fully unfurled state. This may be readily monitored by an operator, visually noting that indicator 399 is in a forwardmost position in slot 336. In this state, the balloon assembly 370 has a minimum stiffness.

FIG. 7B illustrates balloon 372 in a partly furled state. This may be readily monitored by an operator, visually noting that indicator 399 is in an intermediate position in slot 336. In this state, the balloon assembly 370 has an intermediate stiffness.

FIG. 7C illustrates balloon 372 in a full furled state. This may be readily monitored by an operator, visually noting that indicator 399 is in a rearwardmost position in slot 336. In this state, the balloon assembly 370 has a maximum stiffness.

It is appreciated that furling of balloon 372 tightly wraps, condenses and presses balloon 372 around elongate wire 396, thereby stiffening balloon assembly 370.

Reference is now made to FIGS. 8A, 8B, 8C, 8D, 8E, 8F, 8G, 8H, 8I, 8J, 8K and 8L, which are simplified pictorial illustrations of operation of the anchoring assembly and the endoscope system of FIGS. 6 and 7A-7C in accordance with a preferred embodiment of the present invention.

Figure 8A:
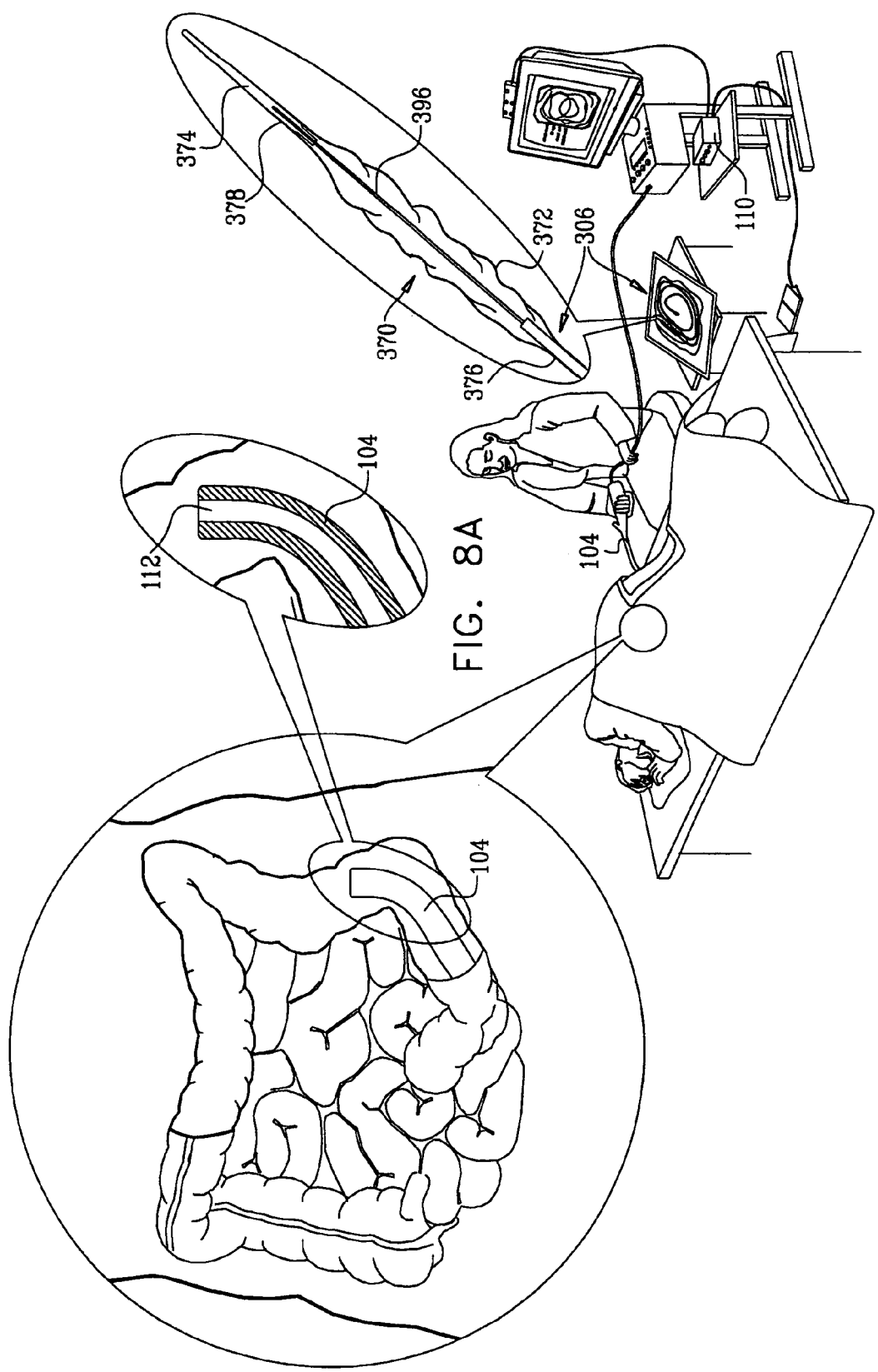

As seen in FIG. 8A, a conventional colonoscopy procedure is initiated, by insertion of a conventional endoscope 104 into operative engagement with a patient. The anchoring assembly 306 of the present invention may remain in a sealed package unless and until needed.

Figure 8B:
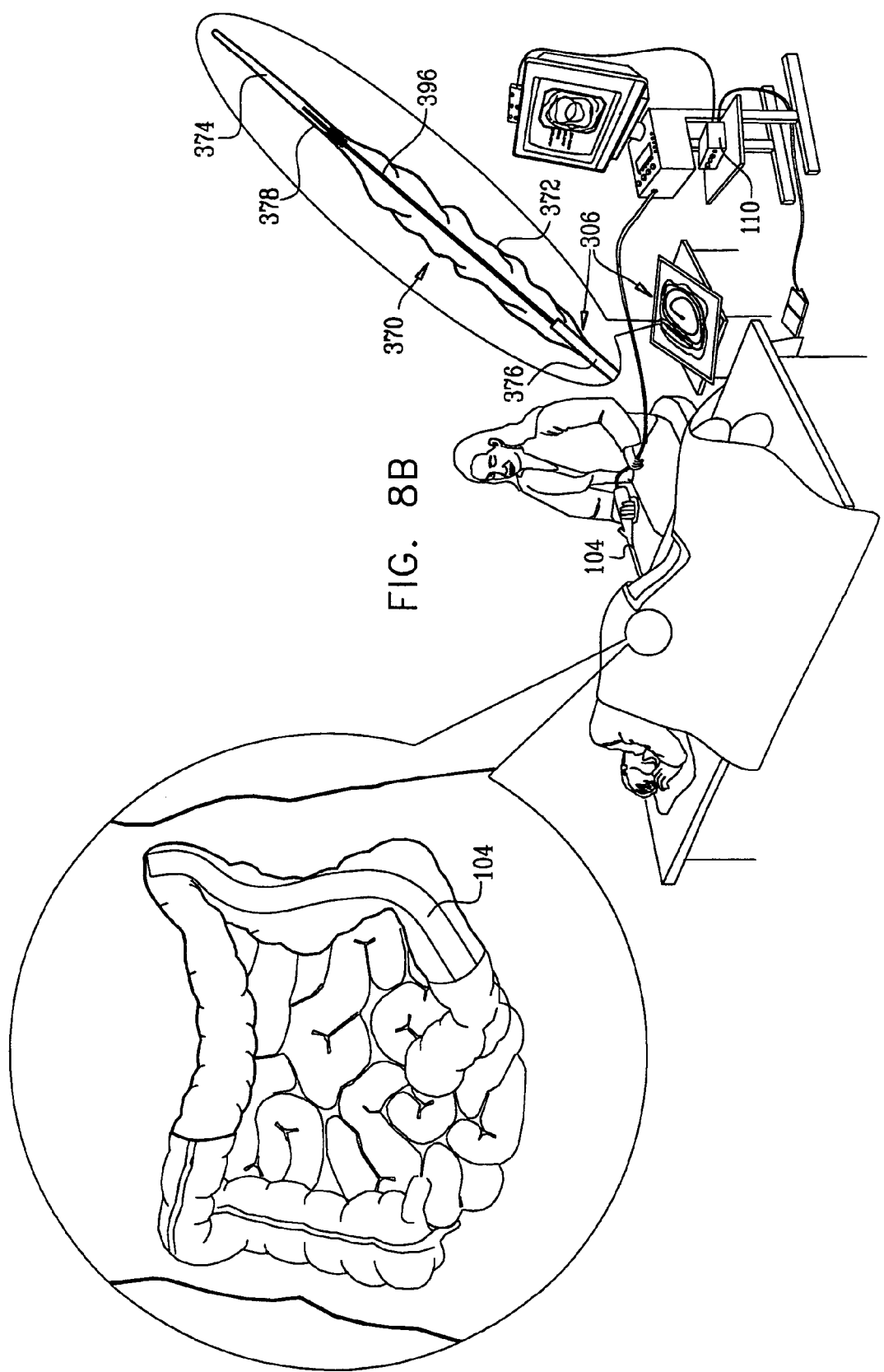

FIG. 8B illustrates a clinical difficulty in the course of the colonoscopy in which the operator is unable to successfully advance past a bend in the large intestine, typically at the splenic flexure.

Figure 8C:
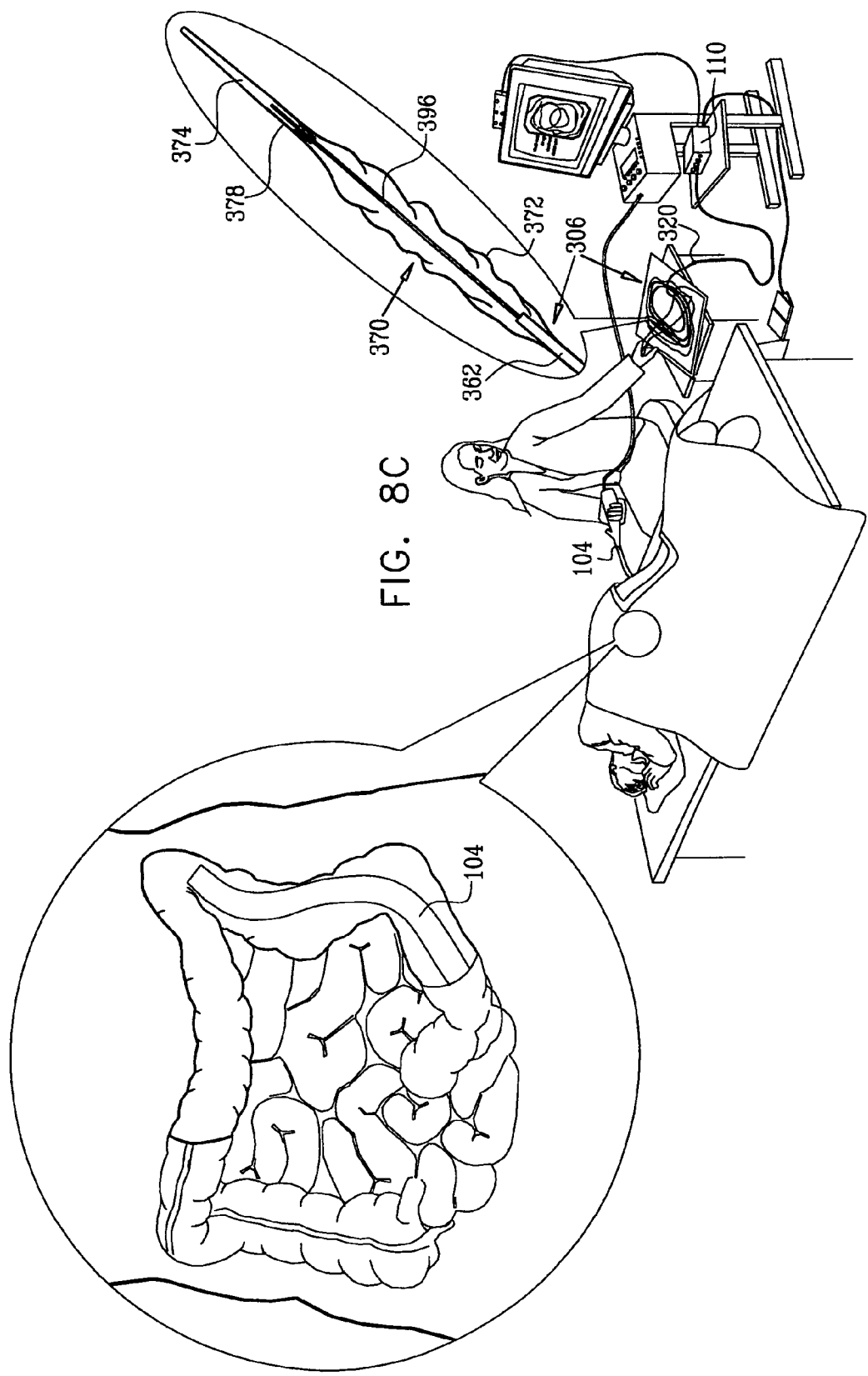

In accordance with the present invention, the operator, facing the clinical difficulty, unpacks the anchoring assembly 306 of the present invention and connects the connector 320 to the inflation/deflation control assembly 110, as shown in FIG. 8C. Preferably, the inflation/deflation control assembly 110 is operated to deflate the balloon assembly 370, forming part of the anchoring assembly 306, when the balloon assembly 370 is in a fully unfurled state (FIG. 7A).

Figure 8D:
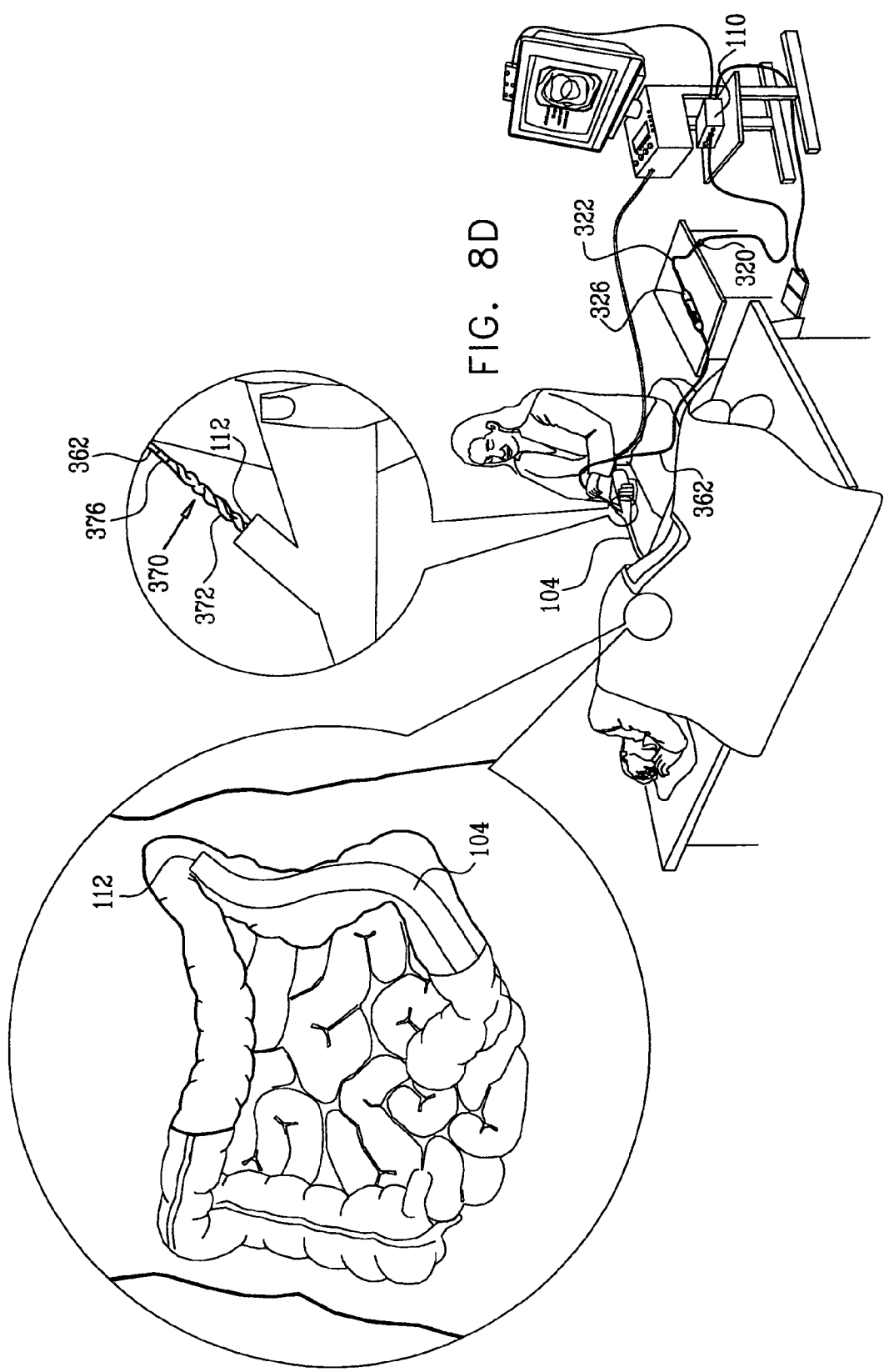

As seen in FIG. 8D, the operator then fully furls the balloon assembly 370 (FIG. 7C) and threads the anchoring assembly with the fully furled balloon assembly 370 in a deflated state, tip element 374 first, through the instrument channel 112 of endoscope 104. As noted above, it is a particular feature of the present invention that the anchoring assembly in its deflated and fully furled state is able to traverse the instrument channel 112.

Figure 8E:
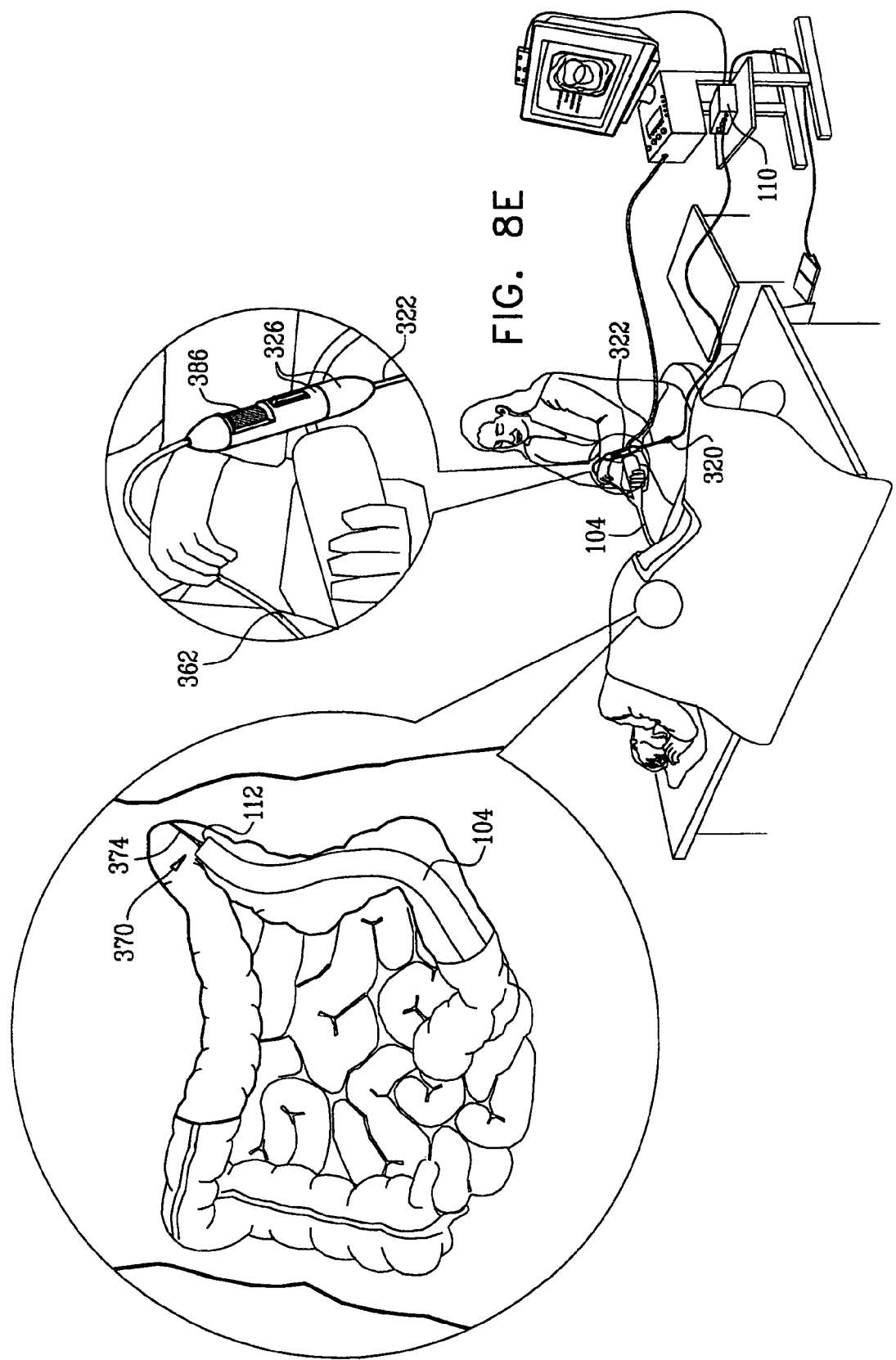

FIG. 8E shows the anchoring assembly 306 partially emerged from the instrument channel 112 at the forward end of endoscope 104.

Figure 8F:
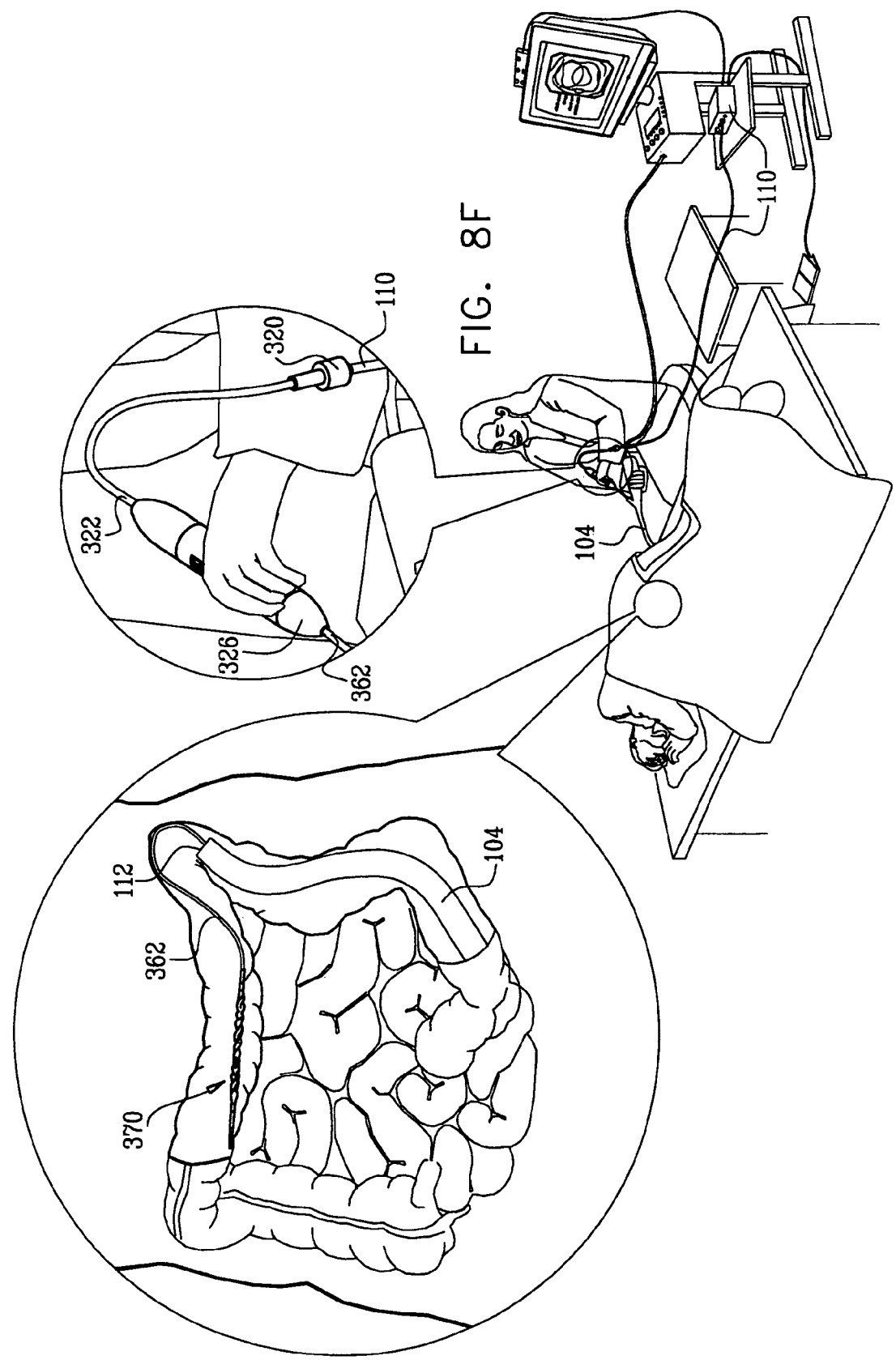

As seen in FIG. 8F, the operator advances the balloon assembly 370 until it is positioned forwardly of the bend in the intestine, preferably by pushing single-lumen tube 362 forwardly through the instrument channel 112 of the endoscope 104.

Figure 8G:
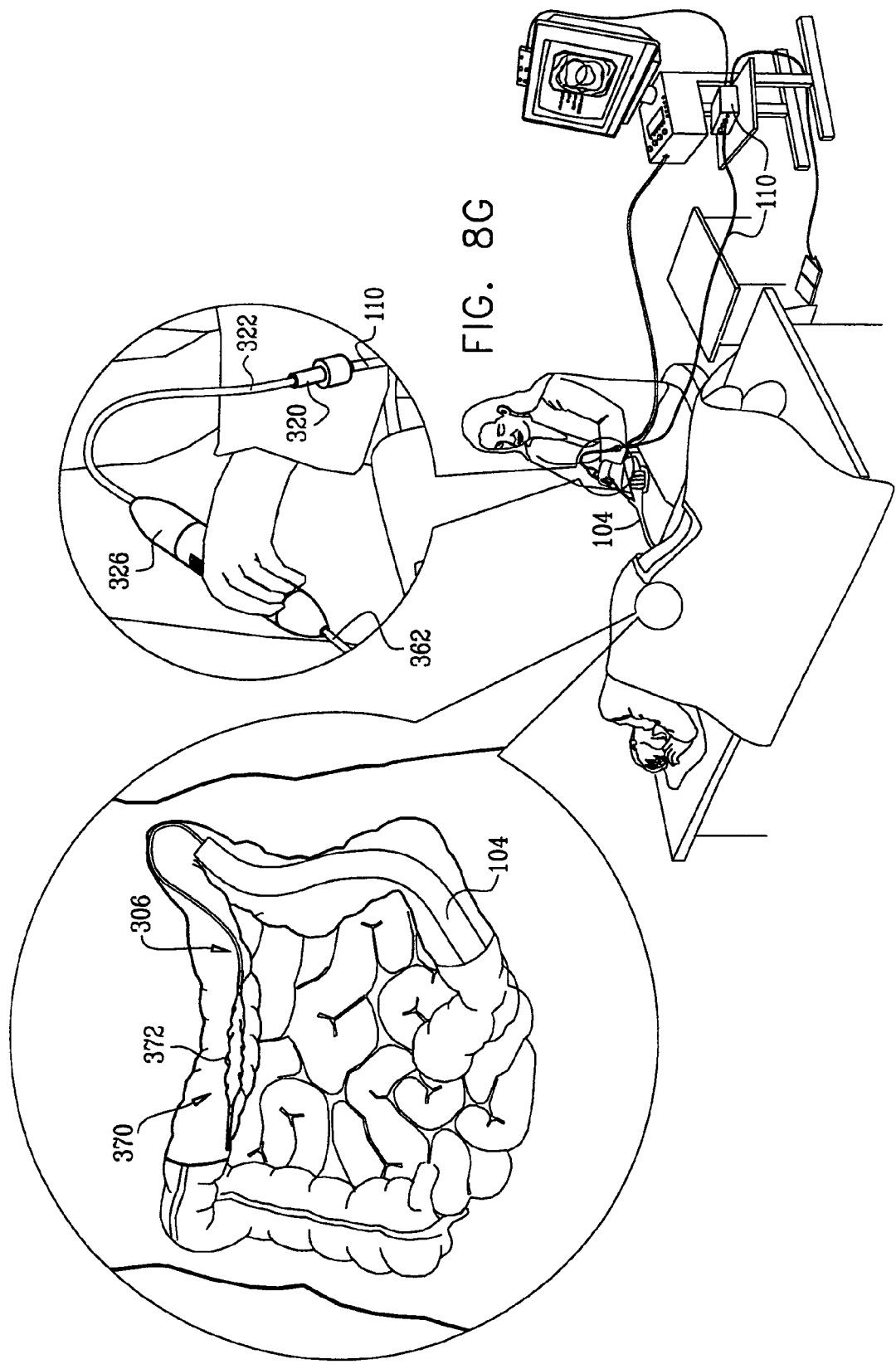
Figure 81:
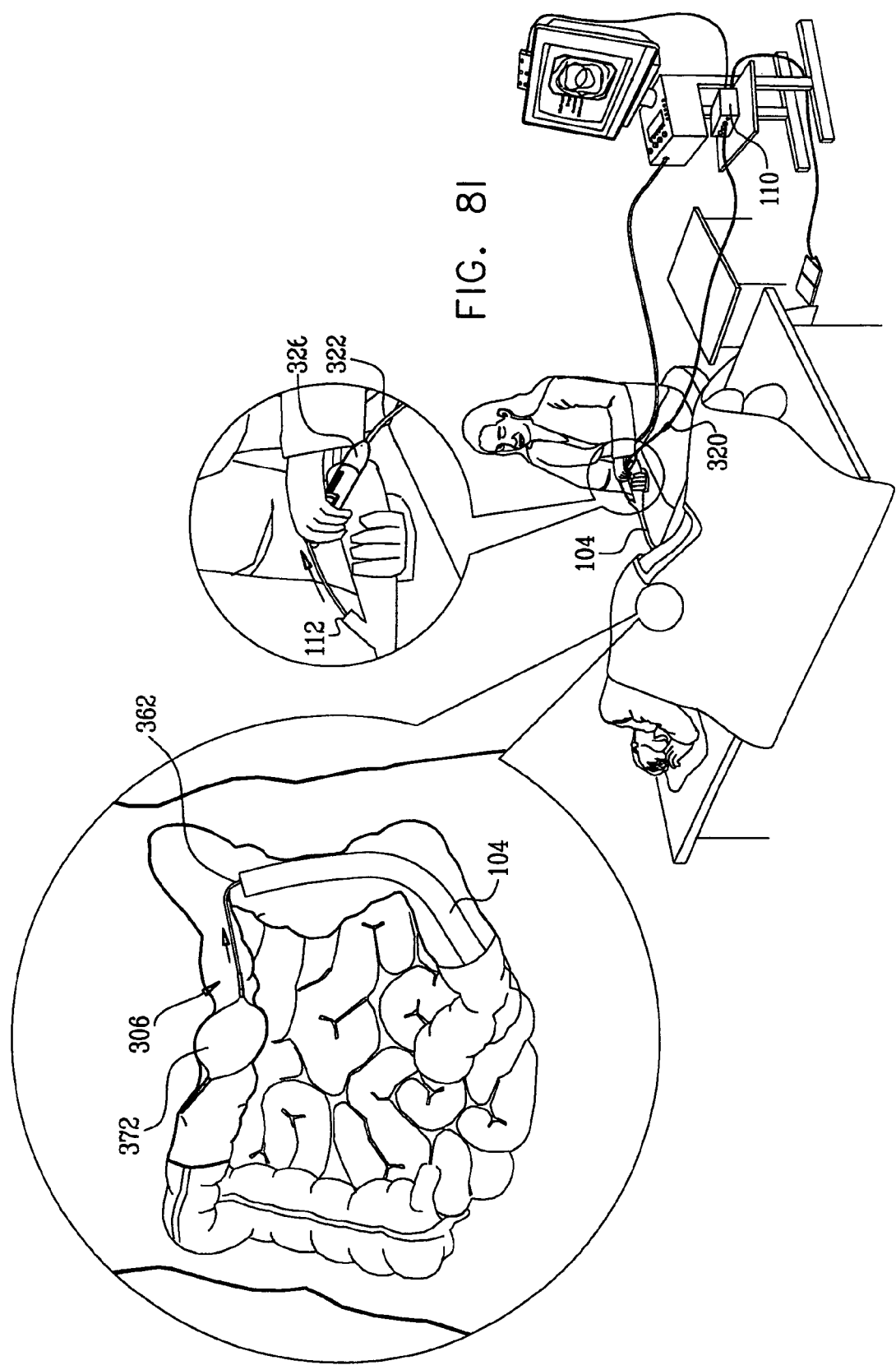

Thereafter, as seen with reference to sequential illustrations FIGS. 7C, 7B and 7A, the operator unfurls the balloon assembly 370 to a fully unfurled state, as seen in FIG. 8G.

The operator preferably then inflates the balloon 372 via lumens 324 and 364 (FIG. 6), using the inflation/deflation control assembly 110. The unfurling and subsequent inflation of balloon 372 in the large intestine, as seen in FIG. 8H, anchors the anchoring assembly 306 in the large intestine, such that the anchoring assembly can serve as a guide for the endoscope 104.

Following anchoring of the anchoring assembly 306 as seen in FIG. 8H, the operator pulls on the single-lumen tube 362, thus tensioning the anchoring assembly 306, as seen in FIG. 8I.

Figure 8J:
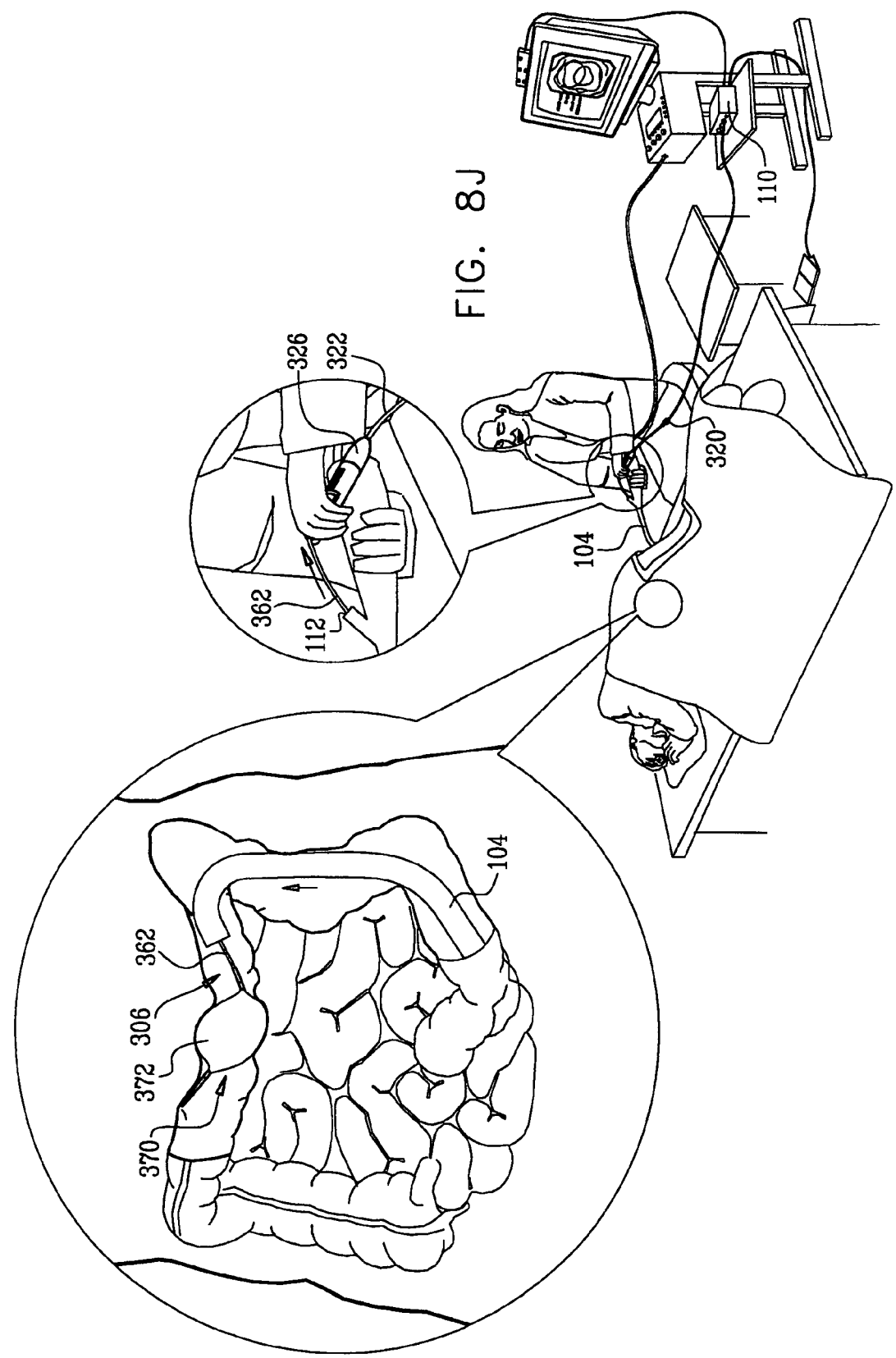

The endoscope is then advanced over the single-lumen tube 362 of anchoring assembly 306 past the bend in the large intestine, which had earlier presented a difficulty, to a location rearwardly adjacent the inflated balloon assembly 370, as seen in FIG. 8J.

Figure 8K:
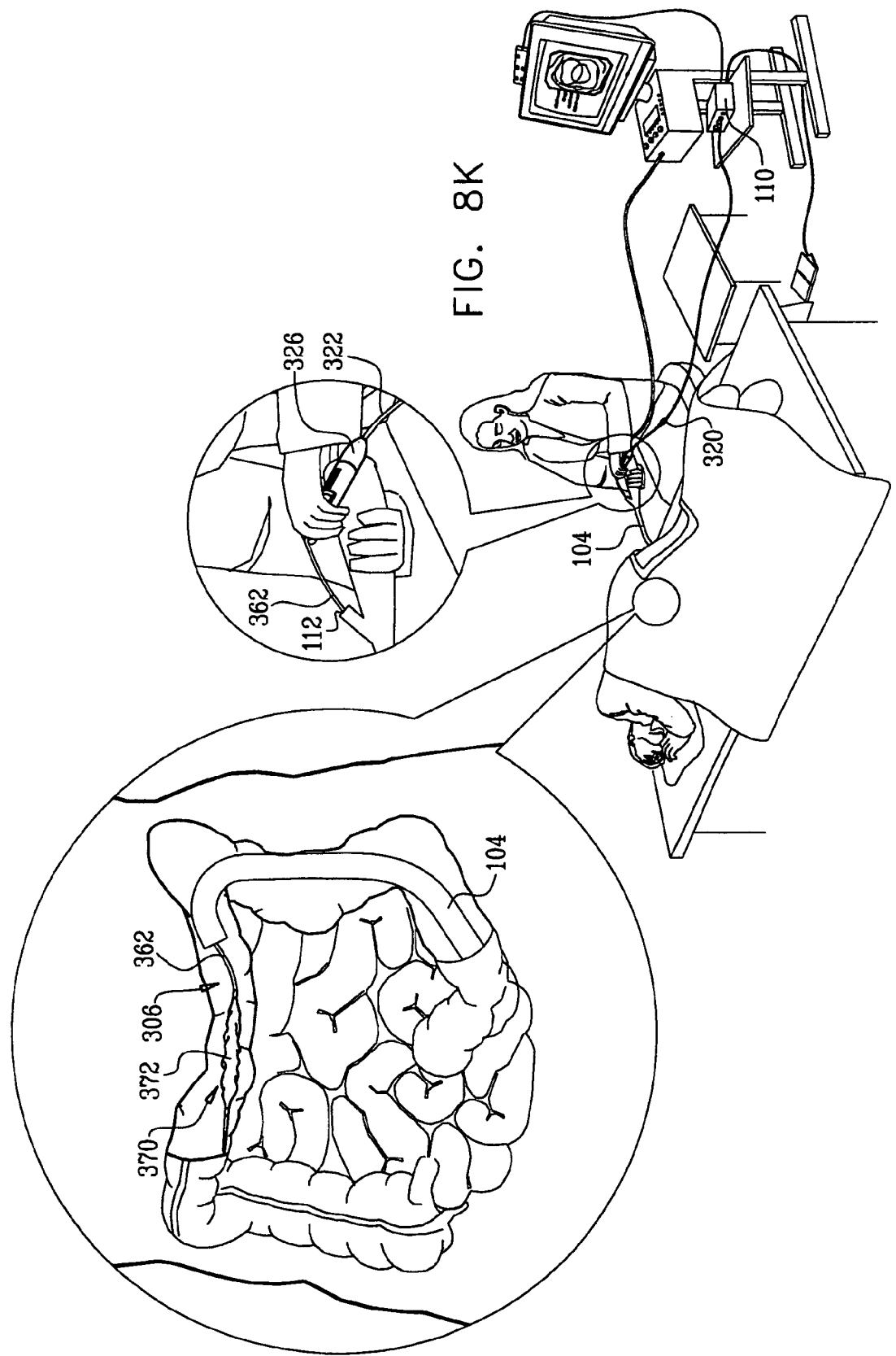

As seen in FIG. 8K, the balloon assembly 370 may then be deflated, via lumens 324 and 364 (FIG. 6), using the inflation/deflation control assembly 110.

The balloon assembly 370 may then be restored to partially or fully furled state. Should it be desired to further advance the endoscope past additional bends which present difficulties, the procedure described hereinabove with respect to FIGS. 8F-8K may be repeated at such bends.

It is appreciated that the operator may selectably vary the stiffness of balloon assembly 370 by selectable furling of balloon assembly 370 as shown in FIGS. 7A-7C, according to specific patient's anatomy, as to ease the advancement of balloon assembly 370 past bends which present difficulties in the large intestine.

Once further use of the anchoring assembly is no longer needed in the colonoscopy procedure, the anchoring assembly 306 with the deflated balloon assembly 370 in a fully furled state (FIG. 7C), may be pulled back by the operator through the instrument channel 112 of the endoscope 104, as seen in FIG. 8L, and removed from the endoscope 104 and discarded. It is a particular feature of the present invention that the anchoring assembly 306 is able to be drawn back through the instrument channel 112 following use.

Reference is now made to FIG. 9, which is a simplified partially pictorial, partially sectional illustration of an anchoring assembly 406 associatable with an endoscope in accordance with a preferred embodiment of the present invention.

As seen in FIG. 9, the anchoring assembly 406 preferably comprises a connector 420 which is suitable for operative engagement with inflation/deflation control assembly 110 (FIG. 1). A single-lumen tube 422 is preferably fixedly mounted on connector 420 and includes a single lumen 424 for inflation/deflation, through which extends an elongate wire 425. Elongate wire 425 is attached to connector 420 and thus is fixed with respect to single-lumen tube 422.

Elongate wire 425 preferably is formed of a flexible metal, such as Nitinol or stainless steel.

Single-lumen tube 422 preferably has an outer diameter of approximately 2.0-3.5 mm. Lumen 424 preferably has an inner diameter of approximately 1.0-3 mm. Elongate wire 425 preferably has a diameter of approximately 0.3-0.9 mm. Single-lumen tube 422 is suitable for passage through the instrument channel 112 of a conventional endoscope and typically has an overall length of between 2 and 3 meters.

An inflatable/deflatable balloon assembly 430 is provided, preferably including a single balloon 434 and a tip element 435. Balloon 434 preferably comprises a non-rotationally-symmetric inflatable/deflatable element, formed of non-substantially-stretchable nylon or polyurethane and having respective rearward and forward neck portions 440 and 442 and a central portion 444, which when inflated has an approximate length of 85-180 mm and a maximum diameter of 55-75 mm in a plane 445 perpendicular to an axis 446 joining rearward and forward neck portions 440 and 442 when the balloon is in a deflated state.

Preferably, central portion 444 comprises an upper surface including an upper rearward facing portion 448 and an upper forward facing portion 450, separated by an upper central portion 452. It is a particular feature of the present invention that both the upper rearward facing portion 448 and the upper forward facing portion 450 are tapered when inflated, as seen in FIG. 9. It is a further particular feature of the present invention that the slope of the upper forward facing portion 450 is different than, greater than and opposite to that of upper rearward facing portion 450.

Preferably, central portion 444 further comprises a lower surface including a lower rearward facing portion 454 and a lower forward facing portion 456, separated by a lower central portion 458. It is a particular feature of the present invention that both the lower rearward facing portion 454 and the lower forward facing portion 456 are tapered when inflated, as seen in FIG. 9. It is a further particular feature of the present invention that the slope of the lower rearward facing portion 454 is different than, greater than and opposite to that of lower forward facing portion 456.

According to a preferred embodiment of the present invention, the slopes of upper forward facing portion 450 and lower rearward facing portion 454, when inflated, are greater than 45 degrees and more preferably greater than 60 degrees, and the slopes of upper rearward facing portion 448 and lower forward facing portion 456, when inflated, are less than 60 degrees and more preferably less than 45 degrees.

It is appreciated that when balloon 434 is inflated, elongate wire 425 is bent, thereby generally aligning central portions 452 and 458 to longitudinally oppose each at plane 445 as shown in FIG. 9, thereby orienting inflated balloon 434 to have a dimension sufficiently large to enable it to anchor in the large intestine without substantial stretching. As seen in FIG. 9, the inflated balloon 434 assumes, by virtue of its being inflated, an asymmetrically shaped orientation along an axis connecting rearward and forward neck portions 440 and 442 of inflated balloon 434, which is tilted with respect to axis 446 connecting neck portions 440 and 442 of the balloon 434 when it is being deflated.

It is further appreciated that when balloon 434 is in a deflated state, upper portion 448 is opposing and generally longitudinally aligned with lower portions 454 and 458, and lower portion 456 is opposing and generally longitudinally aligned with upper portions 450 and 452, thereby to provide reduced cross-sectional diameter of balloon 434 in a deflated state, as to enable balloon 434 to traverse through the instrument channel 112 of a conventional endoscope.

Alternatively to the configuration of non-rotationally-symetric described hereinabove with reference to FIG. 9, the non-rotationally-symmetric inflatable/deflatable element may be realized by employing plural balloons, one or more of which is non-rotationally-symmetric or, as a further alternative, none of which is non-rotationally-symmetric.

Rearward neck portion 440 of balloon 434 is sealingly mounted as by adhesive or ultrasonic welding onto a forward end 460 of single-lumen tube 422. Forward neck portion 442 of balloon 434 is sealingly mounted as by adhesive or ultrasonic welding onto a rearward end of tip element 435. Tip element 435 is generally flexible forward facing conical element, preferably of length between 5 and 40 mm and having maximum outer diameter of approximately 1.0-3.5 mm.

A forward end 462 of elongate wire 425 is fixed to tip element 435, preferably at a rearward end thereof as by adhesive. The elongate wire 425 is also fixed to the forward end 460 of single-lumen tube 422, as by an adhesive or other attachment 463.

Reference is now made to FIGS. 10A, 10B, 10C, 10D, 10E, 10F, 10G, 10H, 10I, 10J and 10K, which are simplified pictorial illustrations of operation of the endoscope system of FIG. 1 and the anchoring assembly of FIG. 9 in accordance with a preferred embodiment of the present invention.

Figure 10A:
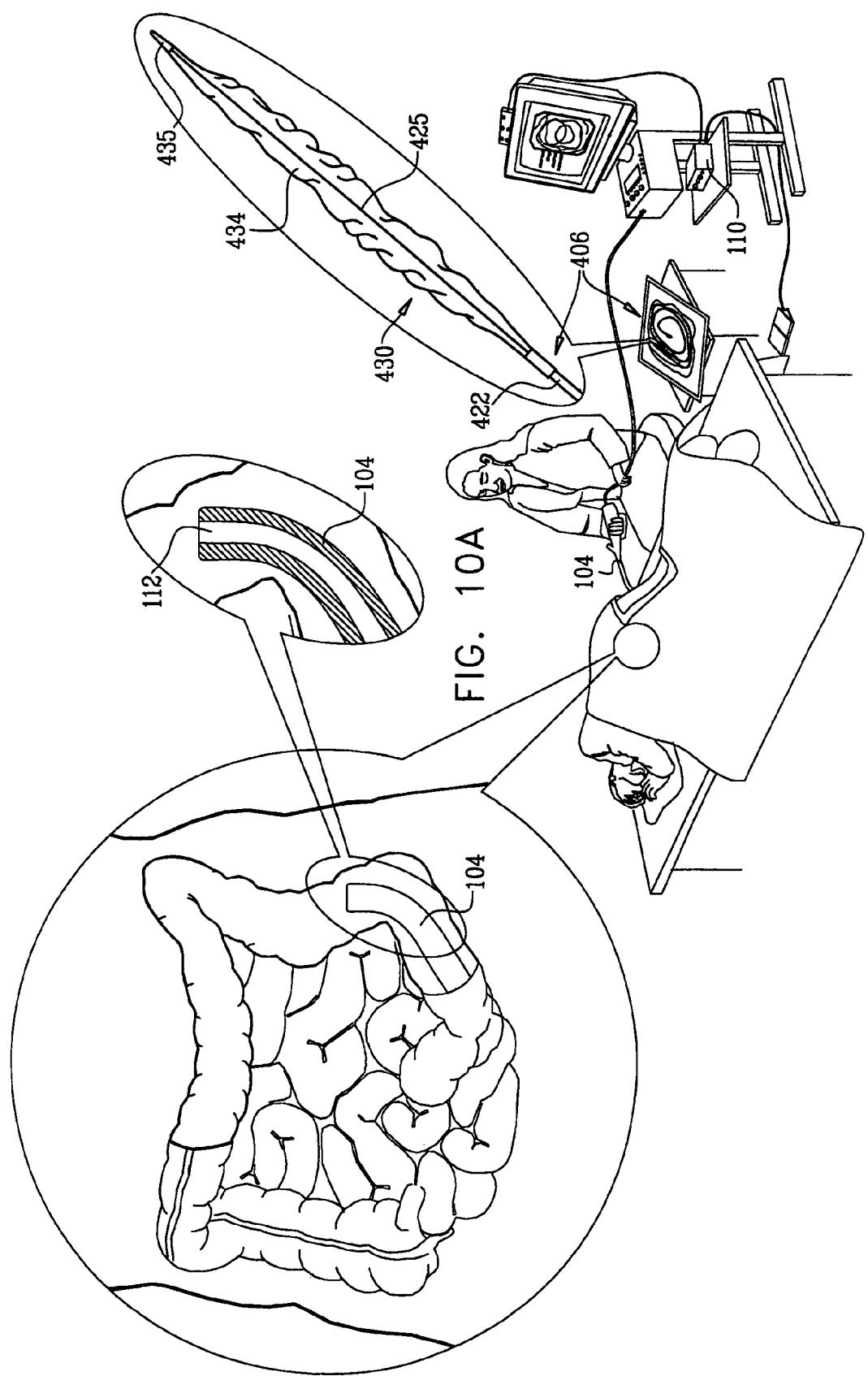

As seen in FIG. 10A, a conventional colonoscopy procedure is initiated, by insertion of a conventional endoscope 104 into operative engagement with a patient. The anchoring assembly 406 of the present invention may remain in a sealed package unless and until needed.

Figure 10B:
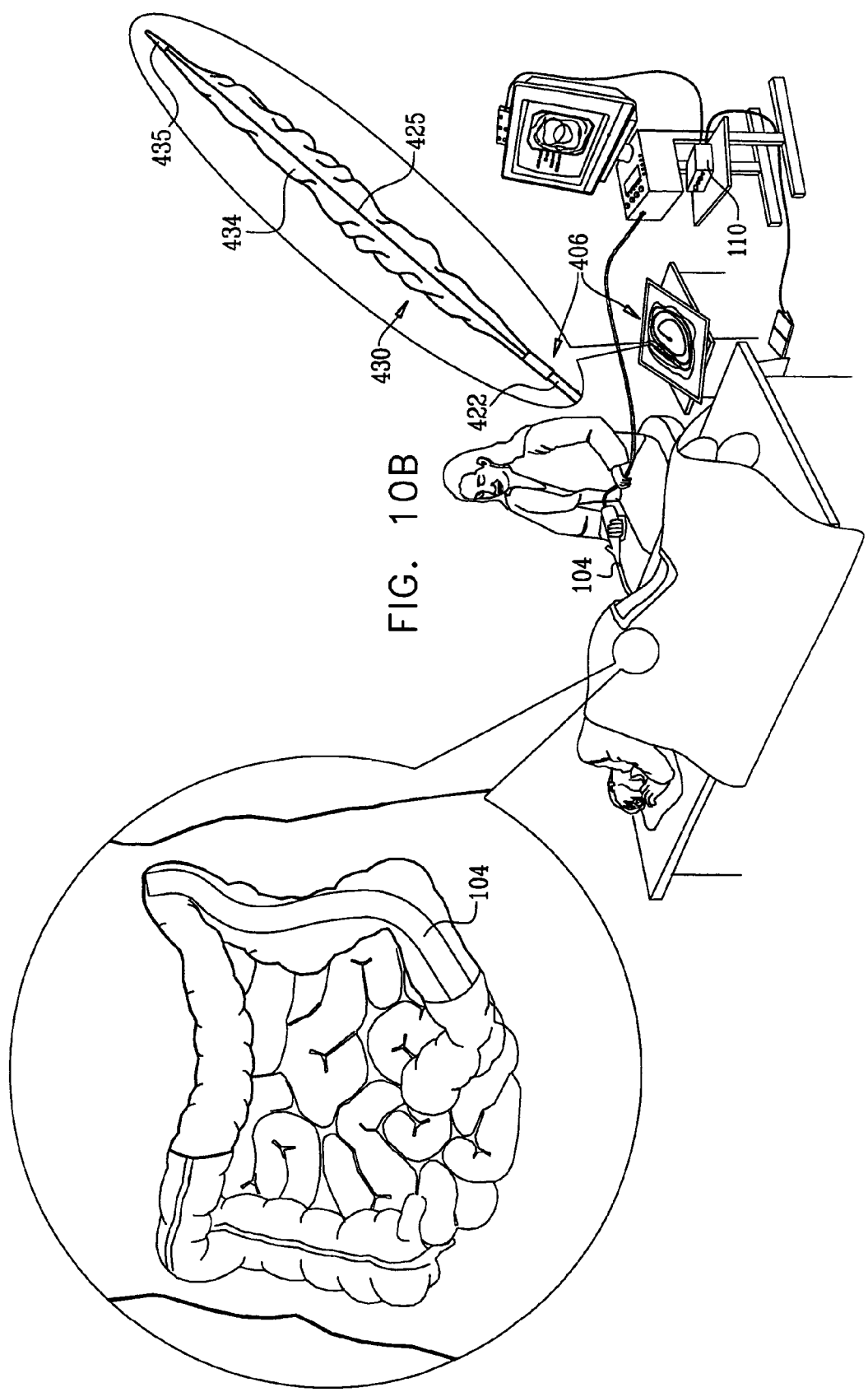

FIG. 10B illustrates a clinical difficulty in the course of the colonoscopy in which the operator is unable to successfully advance past a bend in the large intestine, typically at the splenic flexure.

Figure 10C:
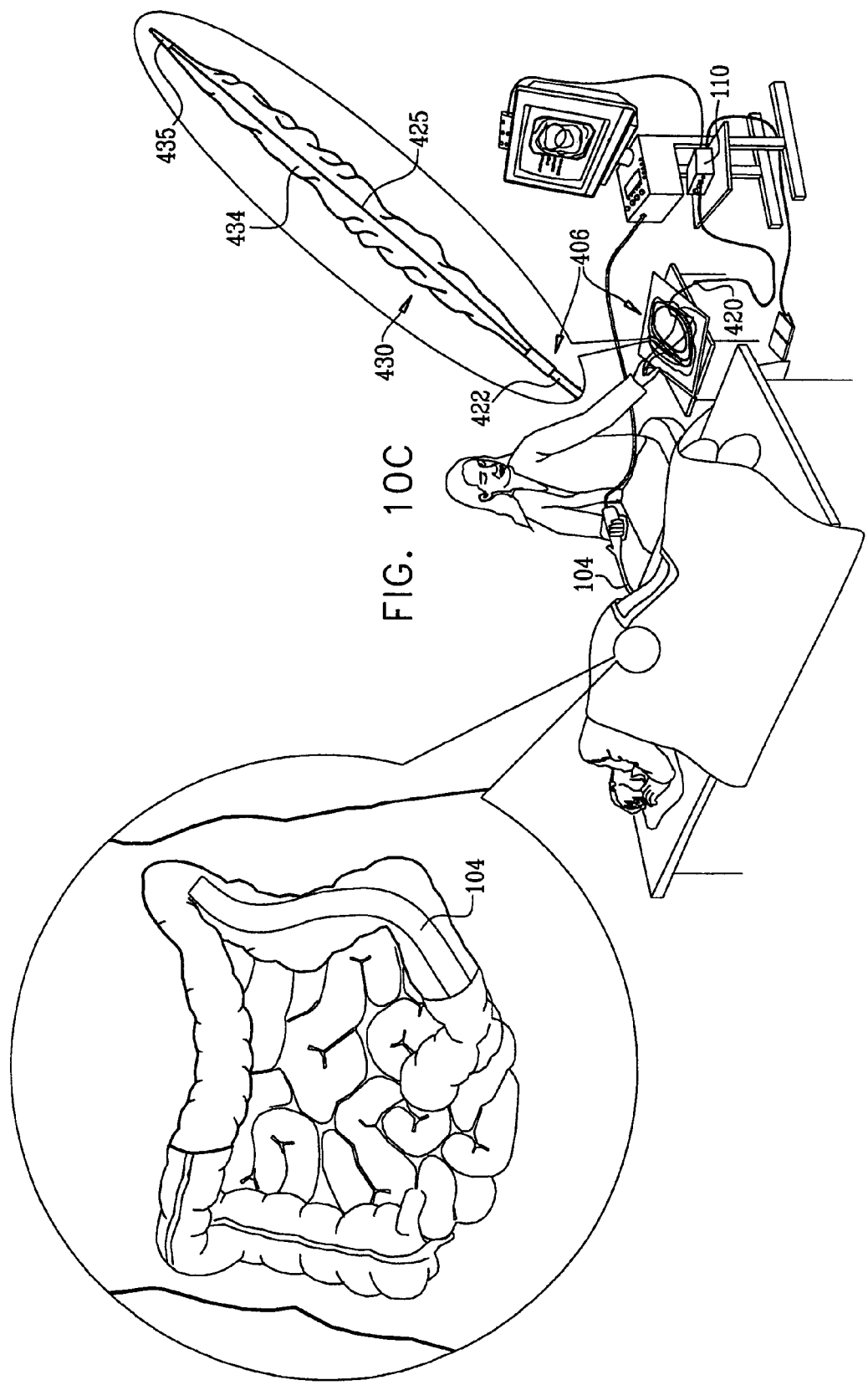

In accordance with the present invention, the operator, facing the clinical difficulty, unpacks the anchoring assembly 406 of the present invention and connects the connector 420 to the inflation/deflation control assembly 110, as shown in FIG. 10C. Preferably, the inflation/deflation control assembly 110 is operated to deflate the balloon assembly 430.

Figure 10D:
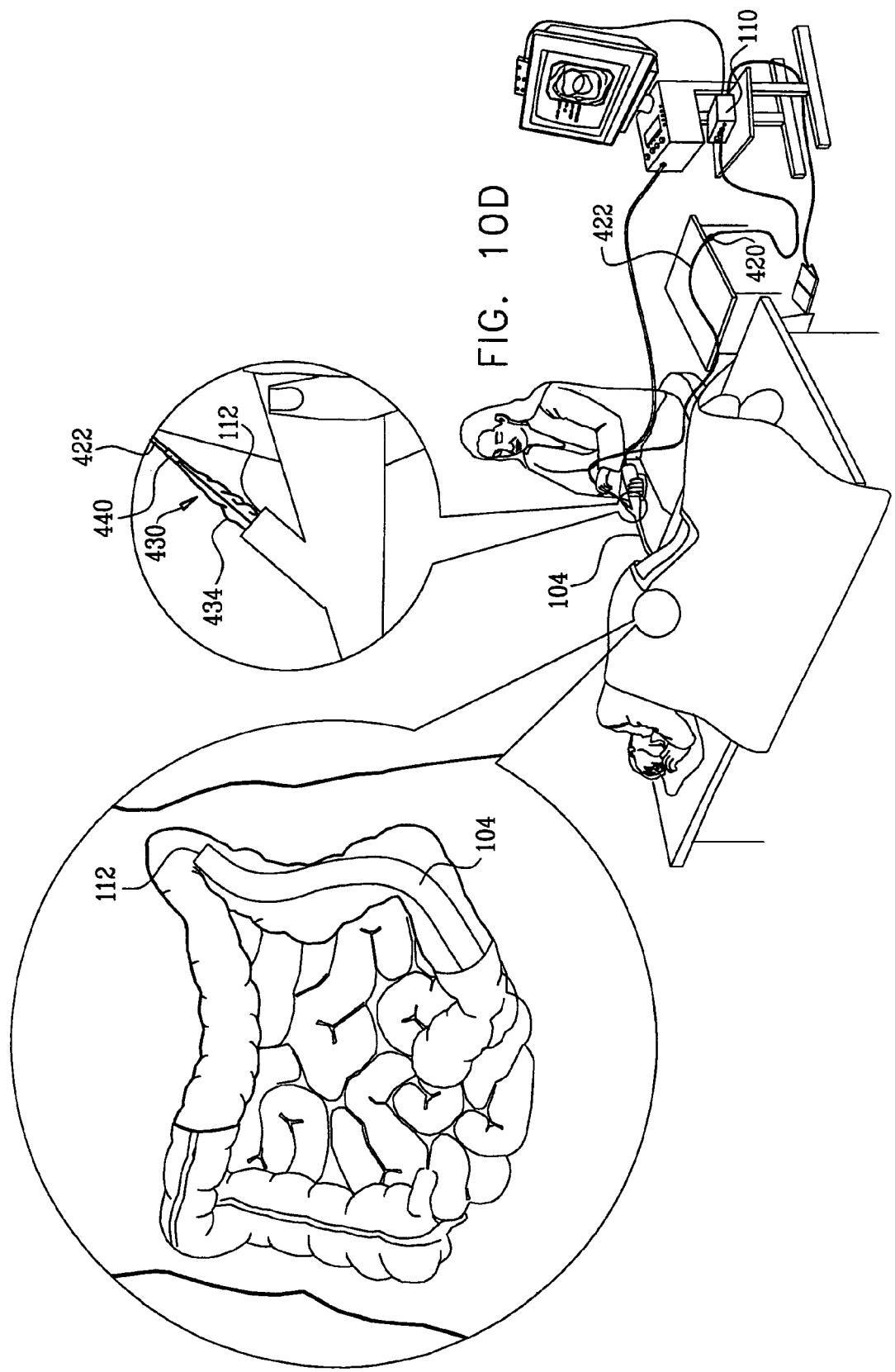

As seen in FIG. 10D, the operator then threads the anchoring assembly with the balloon assembly 430 in a deflated state, tip element 435 first, through the instrument channel 112 of endoscope 104. As noted above, it is a particular feature of the present invention that the anchoring assembly is able to traverse the instrument channel 112.

Figure 10E:
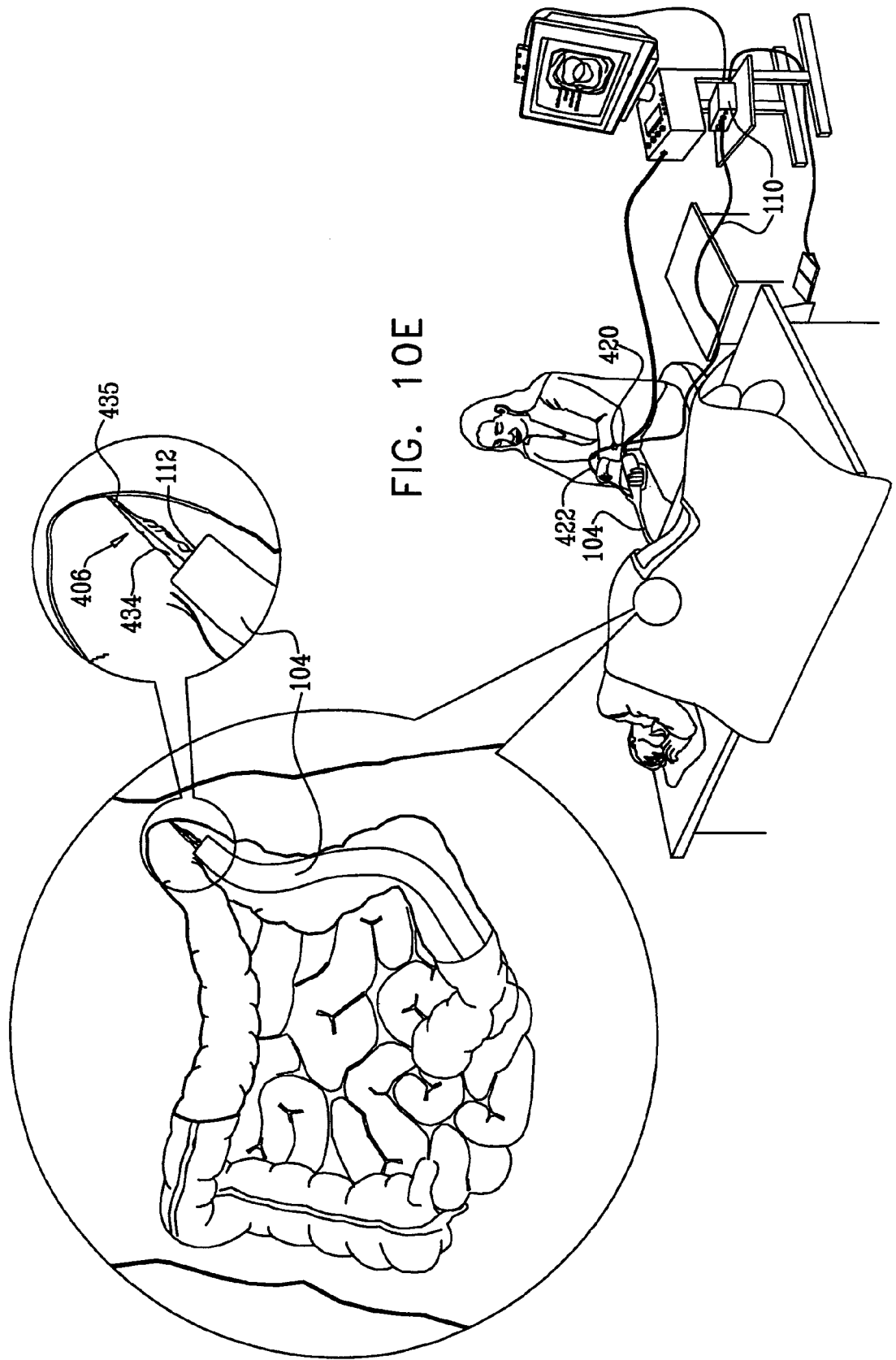

FIG. 10E shows the anchoring assembly 406 partially emerged from the instrument channel 112 at the forward end of endoscope 104.

Figure 10F:
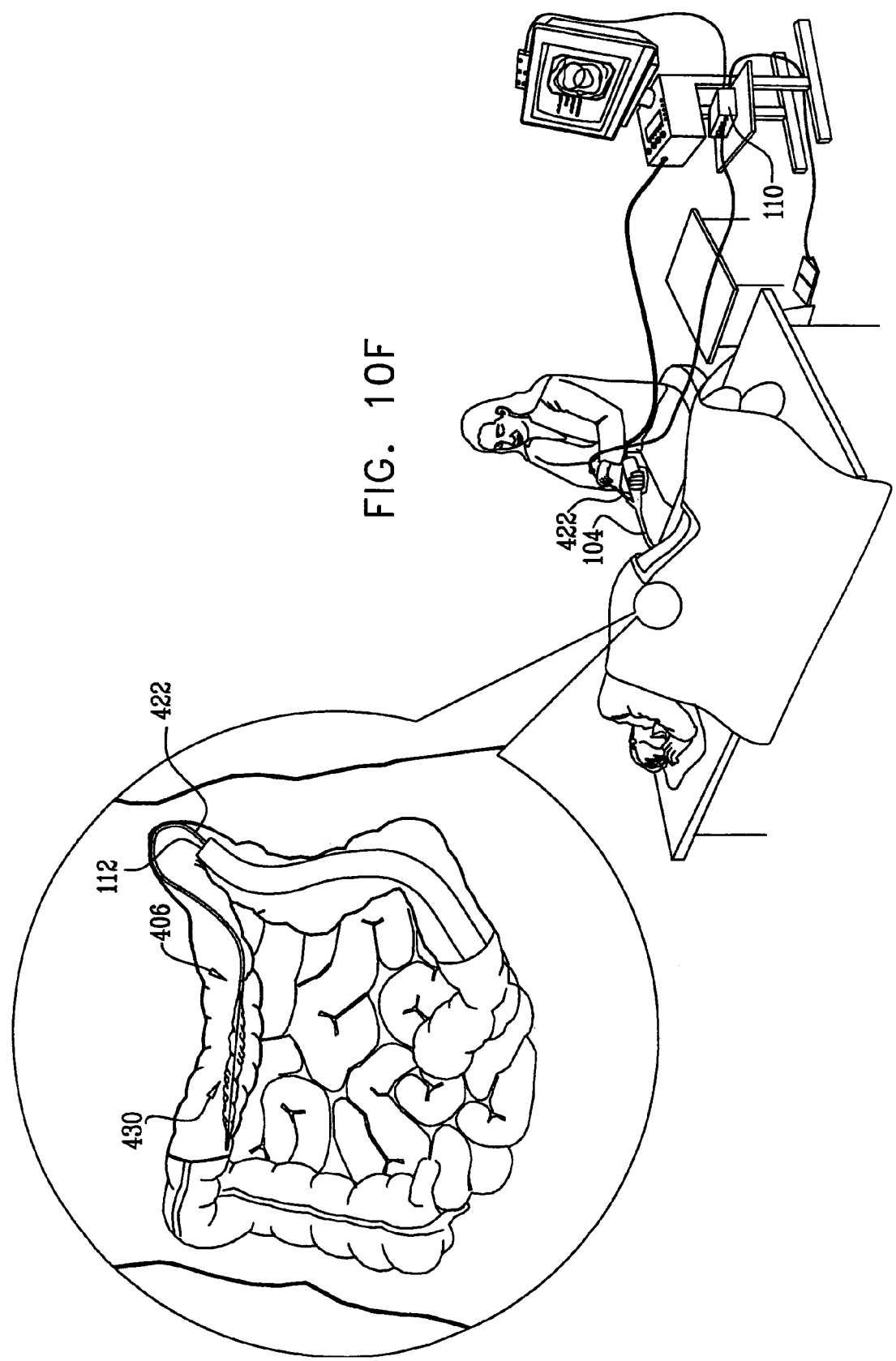

As seen in FIG. 10F, the operator advances the balloon assembly 430 until it is positioned forwardly of the bend in the intestine, preferably by pushing single-lumen tube 422 forwardly through the instrument channel 112 of the endoscope 104.

Figure 10G:
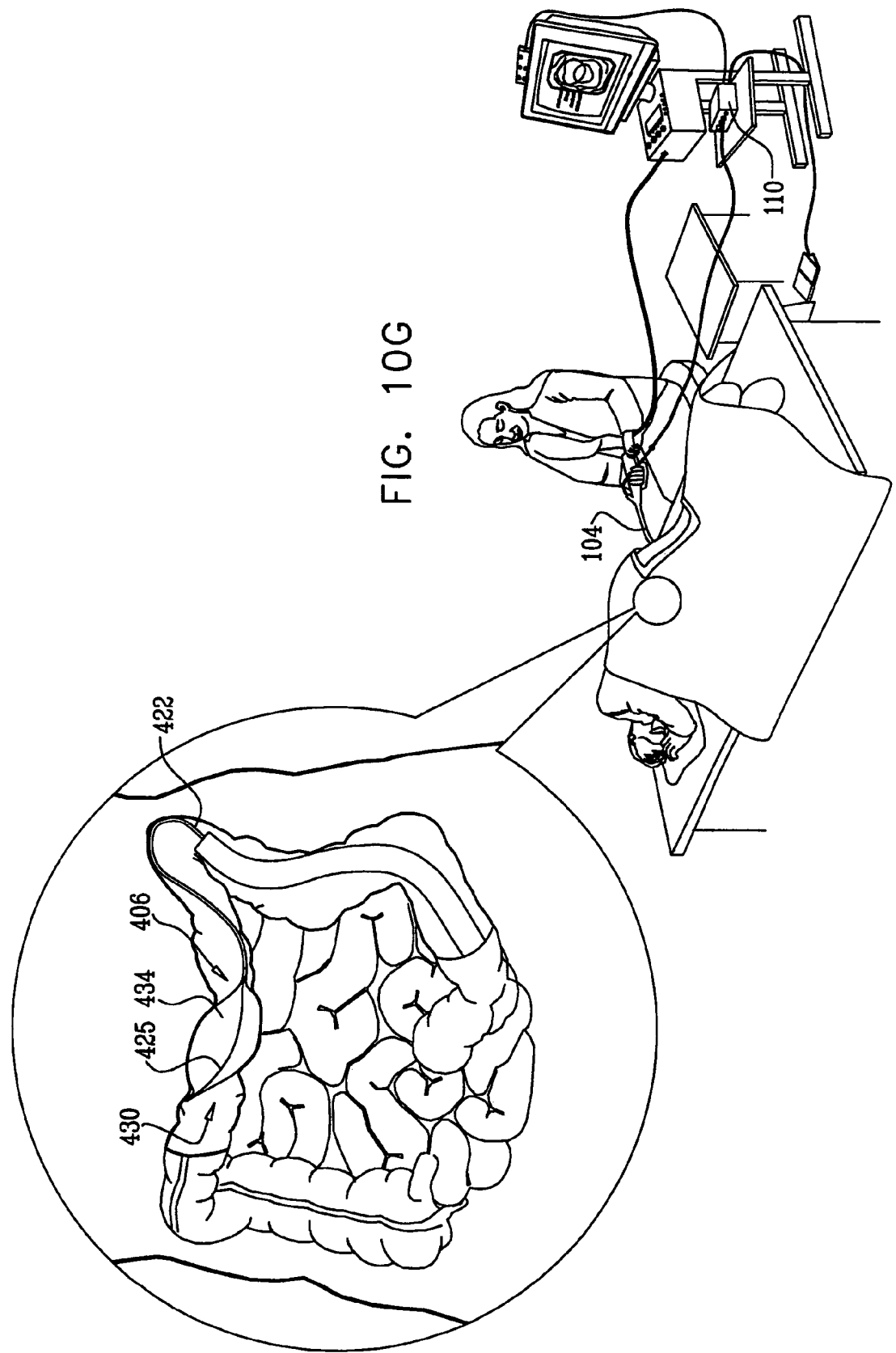
Figure 101:
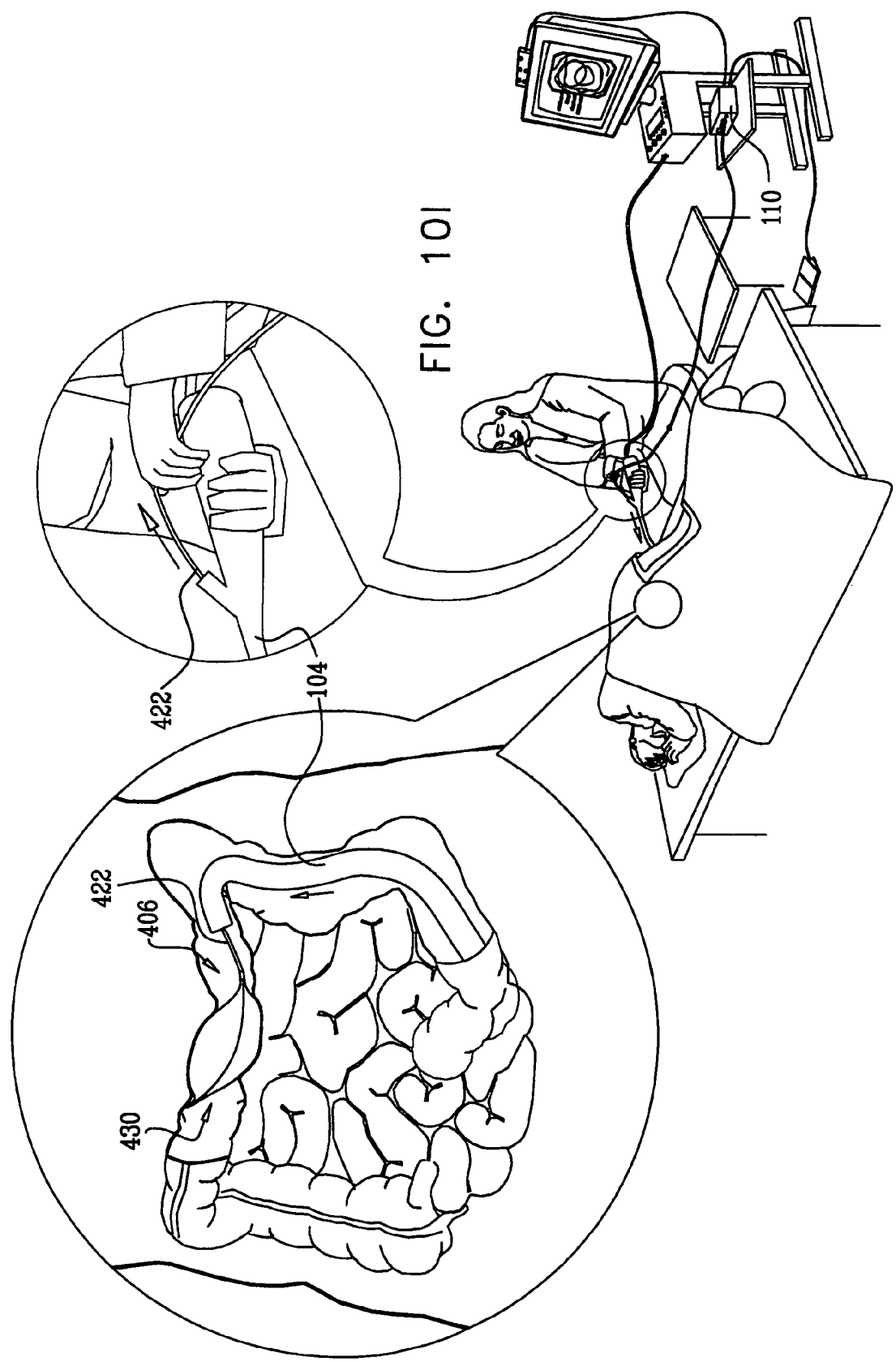

Thereafter, the operator preferably then inflates the balloon 434 via lumen 424, using the inflation/deflation control assembly 110. The inflation of the balloon 434 causes tilting of the balloon 434 in the large intestine, as seen in FIG. 10G, which anchors the balloon 434 in the large intestine by pressure engagement of the balloon generally at plane 445 (FIG. 9) with the inner wall of the intestine. As noted above, plane 445 is perpendicular to axis 446, which is generally parallel to the longitudinal axis of the large intestine at plane 445.

Following anchoring of the anchoring assembly 406 as seen in FIG. 10G, the operator pulls on the single-lumen tube 422, thus tensioning the anchoring assembly 406, as seen in FIG. 10H.

The endoscope 104 is then advanced over the single-lumen tube 422 of anchoring assembly 406 past the bend in the large intestine, which had earlier presented a difficulty, to a location rearwardly adjacent the inflated balloon assembly 430, as seen in FIG. 10I.

Figure 10J:
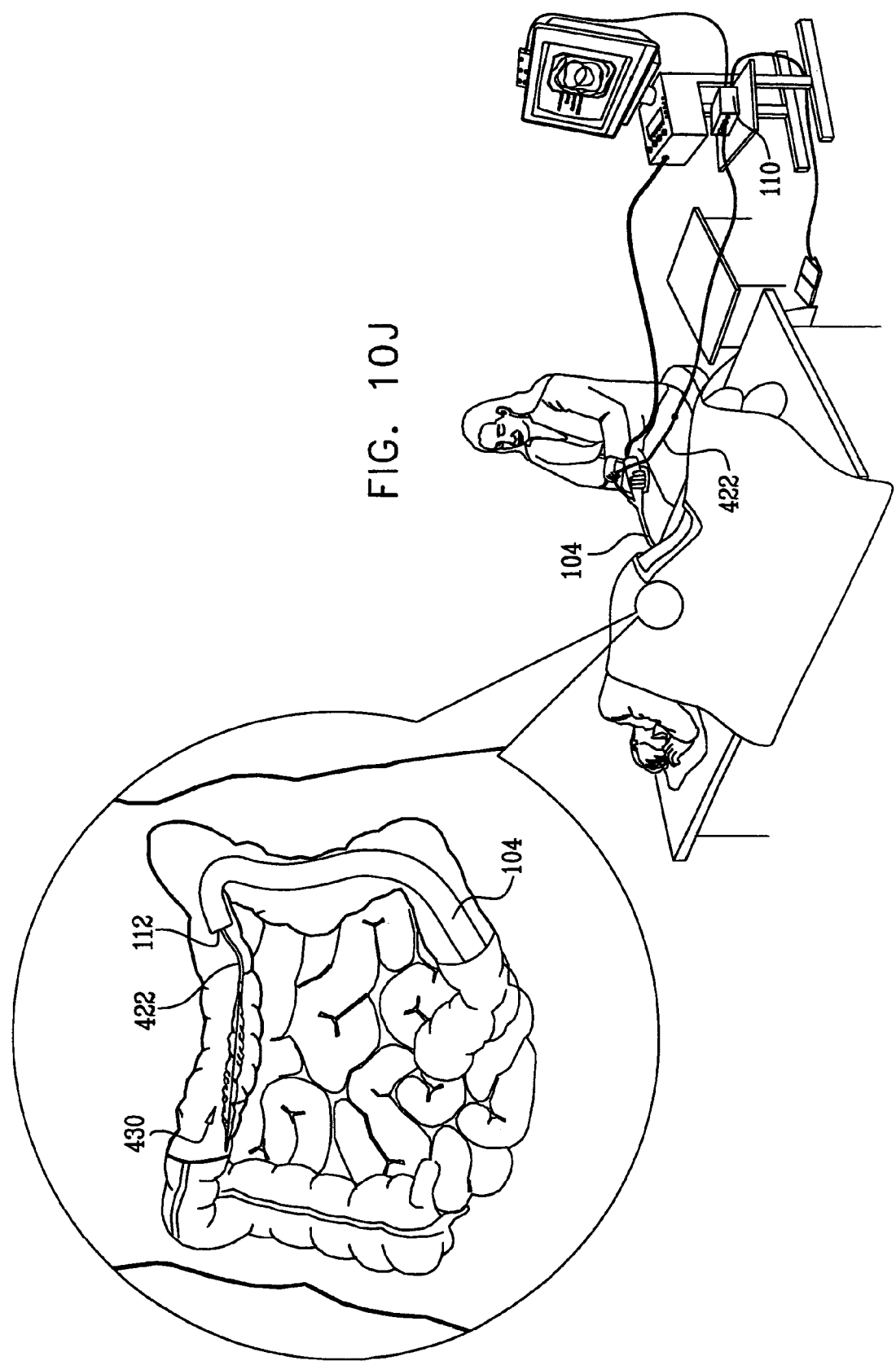

As seen in FIG. 10J, the balloon assembly 430 may then be deflated, via lumen 424, using the inflation/deflation control assembly 110.

Should it be desired to further advance the endoscope past additional bends which present difficulties, the procedure described hereinabove with respect to FIGS. 10F-10J may be repeated at such bends.

Figure 10K:
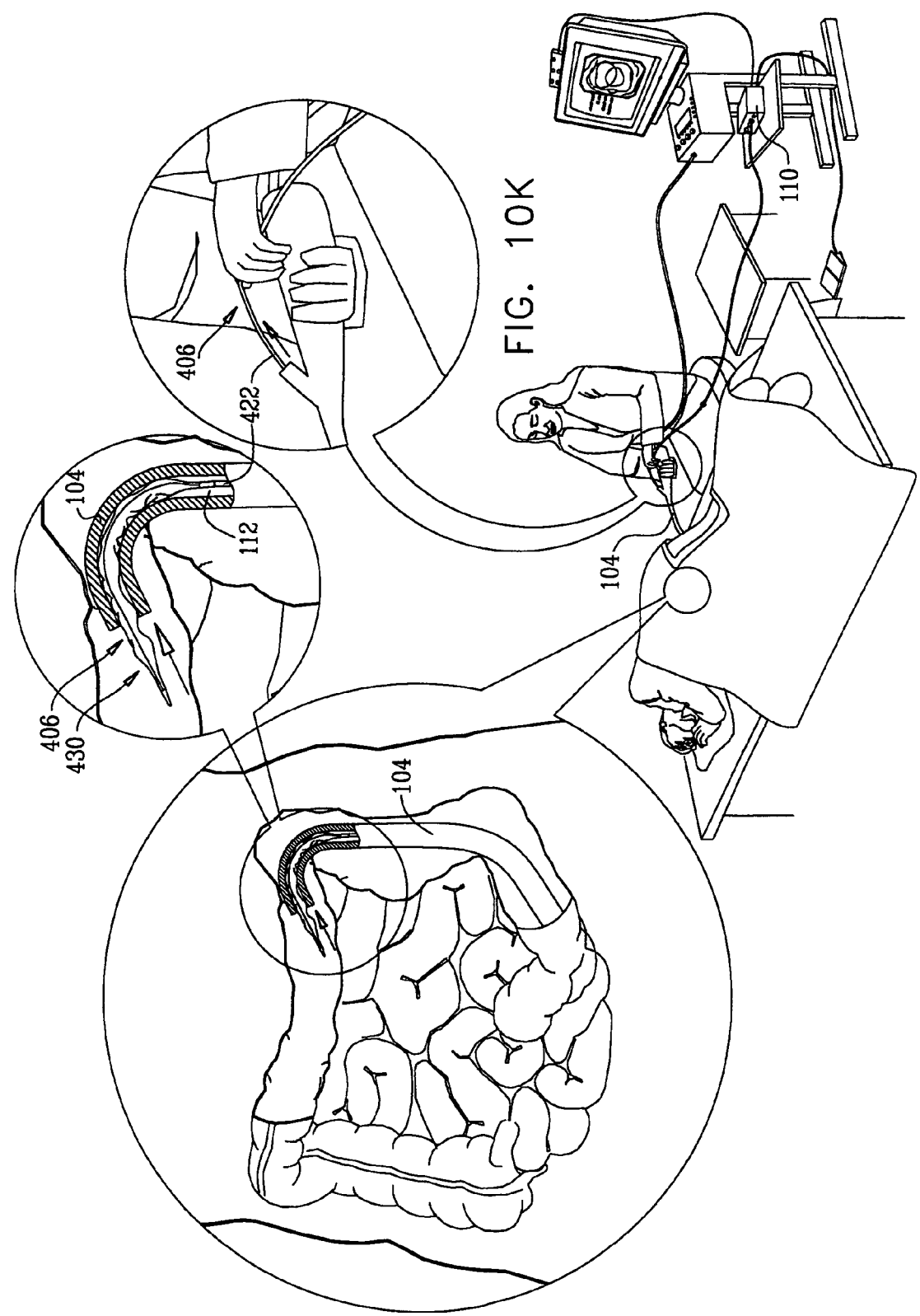

Once further use of the anchoring assembly is no longer needed in the colonoscopy procedure, the anchoring assembly 406 with the deflated balloon assembly 430 may be pulled back by the operator through the instrument channel 112 of the endoscope 104, as seen in FIG. 10K, and removed from the endoscope 104 and discarded. It is a particular feature of the present invention that the anchoring assembly is able to be drawn back through the instrument channel 112 following use.

It will be appreciated by persons skilled in the art that the present invention is not limited by what has been particularly shown and described herein above. Rather the scope of the present invention includes both combinations and sub-combinations of the various features described hereinabove as well as variations and modifications which would occur to persons skilled in the art upon reading the specifications and which are not in the prior art.

The invention claimed is:

1. An endoscope system comprising:
    an endoscope having an instrument channel having an inner diameter; and
    an anchoring assembly including:
        an inflatable/deflatable balloon assembly comprising:
            a catheter; and
            at least one balloon at a forward portion of said catheter; and
        an operator controllable balloon assembly manipulator connected to said catheter at a rearward portion of said catheter, said operator controllable balloon assembly manipulator enabling selectable furling and unfurling of said at least one balloon, whereby said at least one balloon may be furled to a cross sectional size sufficiently small to enable it to pass through said instrument channel to a forward location forwardly of said endoscope within a patient's body portion, and said balloon may be unfurled and inflated when in said forward location, for anchoring thereat, and subsequently deflated and furled when in said forward location within said patient's body portion,
    said operator controllable balloon assembly manipulator comprising a visually sensible indicator for monitoring a furling level of said balloon, said visually sensible indicator providing at least a fully furled balloon indication and a fully unfurled balloon indication.

2. An endoscope system according to claim 1 and wherein said instrument channel has an inner diameter which does not exceed 55 mm.

3. An endoscope system according to claim 1 and wherein said inflatable/deflatable balloon assembly is inflatable to a cross sectional dimension of at least 50 mm.

4. An endoscope system according to claim 1 and wherein said operator controllable balloon assembly manipulator is operative for manipulating said inflatable/deflatable balloon assembly to assume a selectable stiffness.

5. An endoscope system according to claim 1 and wherein said inflatable/deflatable balloon assembly, when in unfurled and inflated state, is deflatable and furlable to a cross sectional size sufficiently small to enable it to pass through said instrument channel.

6. An endoscope system according to claim 1 and wherein said inflatable/deflatable balloon assembly is positionable by orientation thereof within the large intestine so as to realize an overall dimension which is sufficient for anchoring in the large intestine.

7. An endoscope system according to claim 1 and wherein said at least one balloon is arrangeable, when deflated, in a first orientation along a deflated balloon axis and arrangeable by virtue of its being inflated, in a second asymmetrically shaped orientation along an inflated balloon axis, tilted with respect to said deflated balloon axis.

8. An endoscope system according to claim 1 and wherein said at least one balloon, when unfurled, is inflatable without substantial stretching to have a dimension sufficiently large to enable it to anchor in a location within a patient's body portion having a diameter at least 13 times greater than the inner diameter of said instrument channel.

9. For use with an endoscope system including an endoscope having an instrument channel having an inner diameter,
    an anchoring assembly comprising:
        an inflatable/deflatable balloon assembly comprising:
            a catheter; and
            at least one balloon at a forward portion of said catheter; and
        an operator controllable balloon assembly manipulator connected to said catheter at a rearward portion of said catheter, said operator controllable balloon assembly manipulator enabling selectable furling and unfurling of said at least one balloon, whereby said at least one balloon may be furled to a cross sectional size sufficiently small to enable it to pass through said instrument channel to a forward location forwardly of said endoscope within a patient's body portion, and said balloon may be unfurled and inflated when in said forward location, for anchoring thereat, and subsequently deflated and furled when in said forward location within said patient's body portion,
    said operator controllable balloon assembly manipulator comprising a visually sensible indicator for monitoring a furling level of said balloon, said visually sensible indicator providing at least a fully furled balloon indication and a fully unfurled balloon indication.

10. An anchoring assembly according to claim 9 and wherein said instrument channel has an inner diameter which does not exceed 5.5 mm.

11. An anchoring assembly according to claim 9 and wherein said inflatable/deflatable balloon assembly is inflatable to a cross sectional dimension of at least 50 mm.

12. An anchoring assembly according to claim 9 and wherein said operator controllable balloon assembly manipulator is operative for manipulating said inflatable/deflatable balloon assembly to assume a selectable stiffness.

13. An anchoring assembly according to claim 9 and wherein said inflatable/deflatable balloon assembly, when in unfurled and inflated state, is deflatable and furlable to a cross sectional size sufficiently small to enable it to pass through said instrument channel.

14. An anchoring assembly according to claim 9 and wherein said inflatable/deflatable balloon assembly is positionable by orientation thereof within the large intestine so as to realize an overall dimension which is sufficient for anchoring in the large intestine.

15. An anchoring assembly according to claim 9 and wherein said at least one balloon is arrangeable, when deflated, in a first orientation along a deflated balloon axis and arrangeable by virtue of its being inflated, in a second asymmetrically shaped orientation along an inflated balloon axis, tilted with respect to said deflated balloon axis.

16. An anchoring assembly according to claim 9 and wherein said at least one balloon, when unfurled, is inflatable without substantial stretching to have a dimension sufficiently large to enable it to anchor in a location within a patient's body portion having a diameter at least 13 times greater than the inner diameter of said instrument channel.

\* \* \* \* \*